United States Patent
Frank et al.

(10) Patent No.: US 11,304,980 B2
(45) Date of Patent: *Apr. 19, 2022

(54) RESTIMULATION OF CRYOPRESERVED TUMOR INFILTRATING LYMPHOCYTES

(71) Applicant: Iovance Biotherapeutics Inc., San Carlos, CA (US)

(72) Inventors: Ian Frank, Tampa, FL (US); Michael T. Lotze, Pittsburgh, PA (US)

(73) Assignee: Iovance Biotherapeutics, Inc., San Carlos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/459,988

(22) Filed: Aug. 27, 2021

(65) Prior Publication Data

US 2021/0401889 A1    Dec. 30, 2021

Related U.S. Application Data

(63) Continuation of application No. 17/233,290, filed on Apr. 16, 2021, now Pat. No. 11,179,419, which is a continuation of application No. 15/751,440, filed as application No. PCT/US2017/058610 on Oct. 26, 2017, now Pat. No. 11,026,974.

(60) Provisional application No. 62/415,452, filed on Oct. 31, 2016, provisional application No. 62/413,387, filed on Oct. 26, 2016, provisional application No. 62/413,283, filed on Oct. 26, 2016.

(51) Int. Cl.

| A61K 35/17 | (2015.01) |
|---|---|
| A01N 1/02 | (2006.01) |
| A61P 35/00 | (2006.01) |
| C07K 14/725 | (2006.01) |
| C07K 16/00 | (2006.01) |
| C12N 15/85 | (2006.01) |
| C12N 5/0783 | (2010.01) |
| G01N 33/50 | (2006.01) |

(52) U.S. Cl.
CPC ............ *A61K 35/17* (2013.01); *A01N 1/0284* (2013.01); *A61P 35/00* (2018.01); *C07K 14/7051* (2013.01); *C07K 16/00* (2013.01); *C12N 5/0636* (2013.01); *C12N 15/85* (2013.01); *G01N 33/5005* (2013.01); *C07K 2317/24* (2013.01); *C07K 2319/03* (2013.01); *C07K 2319/33* (2013.01); *C12N 2501/04* (2013.01); *C12N 2501/2302* (2013.01); *C12N 2502/11* (2013.01); *C12N 2502/1121* (2013.01); *C12N 2502/99* (2013.01)

(58) Field of Classification Search
None
See application file for complete search history.

(56) References Cited

U.S. PATENT DOCUMENTS

| 4,766,106 | A | 8/1988 | Katre et al. |
|---|---|---|---|
| 4,902,502 | A | 2/1990 | Nitecki et al. |
| 5,089,261 | A | 2/1992 | Nitecki et al. |
| 5,206,344 | A | 4/1993 | Katre et al. |
| 6,706,289 | B2 | 3/2004 | Lewis et al. |
| 7,943,743 | B2 | 5/2011 | Korman et al. |
| 8,008,449 | B2 | 8/2011 | Korman et al. |
| 8,034,334 | B2 | 10/2011 | Dudley et al. |
| 8,287,857 | B2 | 10/2012 | Dudley et al. |
| 8,383,099 | B2 | 2/2013 | Dudley et al. |
| 8,809,050 | B2 | 8/2014 | Vera et al. |
| 8,956,860 | B2 | 2/2015 | Vera et al. |
| 9,074,185 | B2 | 7/2015 | Dudley et al. |
| 9,844,569 | B2 | 12/2017 | Gros et al. |
| 9,914,783 | B1 | 3/2018 | Afar et al. |
| 11,026,974 | B2 * | 6/2021 | Frank ............... C07K 16/00 |
| 11,179,419 | B2 * | 11/2021 | Frank ............. G01N 33/5005 |
| 2005/0106717 | A1 | 5/2005 | Wilson et al. |
| 2011/0052530 | A1 | 3/2011 | Dudley et al. |
| 2011/0136228 | A1 | 6/2011 | Vera et al. |
| 2012/0244133 | A1 | 9/2012 | Rosenberg et al. |
| 2013/0102075 | A1 | 4/2013 | Vera et al. |
| 2013/0115617 | A1 | 5/2013 | Wilson |
| 2014/0328791 | A1 | 11/2014 | Bossard et al. |
| 2014/0377739 | A1 | 12/2014 | Welch et al. |
| 2015/0175966 | A1 | 5/2015 | Vera et al. |
| 2016/0010058 | A1 | 1/2016 | Gros et al. |
| 2016/0208216 | A1 | 7/2016 | Vera et al. |
| 2016/0215262 | A1 | 7/2016 | Powell |
| 2017/0044496 | A1 | 2/2017 | Samaik et al. |

(Continued)

FOREIGN PATENT DOCUMENTS

| WO | WO 2004/031370 A1 | 4/2004 |
|---|---|---|
| WO | WO 2009/040789 A1 | 4/2009 |

(Continued)

OTHER PUBLICATIONS

Garaud, et al. (2014) "A Simple and Rapid Protocol to Non-enzymatically Dissociate Fresh Human Tissues for the Analysis of Infiltrating Lymphocytes" Journal of Visualized Experiments (94): article 52392, 9 pages long. (Year: 2014).*

(Continued)

*Primary Examiner* — Robert M Kelly

(74) *Attorney, Agent, or Firm* — Morgan, Lewis & Bockius LLP

(57) ABSTRACT

The present disclosure provides methods for re-stimulating TIL populations that lead to improved phenotype and increased metabolic health of the TILs and provides methods of assaying for TIL populations to determine suitability for more efficacious infusion after re-stimulation.

20 Claims, 17 Drawing Sheets

Specification includes a Sequence Listing.

(56) References Cited

U.S. PATENT DOCUMENTS

| | | | |
|---|---|---|---|
| 2017/0081635 | A1 | 3/2017 | Samaik et al. |
| 2017/0107490 | A1 | 4/2017 | Maeurer |
| 2017/0152478 | A1 | 6/2017 | Rosenberg et al. |
| 2018/0127715 | A1 | 5/2018 | Veerapathran et al. |
| 2018/0187150 | A1 | 7/2018 | De Larichaudy |
| 2018/0207201 | A1 | 7/2018 | Wardell et al. |
| 2018/0228841 | A1 | 8/2018 | Frank et al. |

FOREIGN PATENT DOCUMENTS

| | | | |
|---|---|---|---|
| WO | 2011072088 | A2 | 6/2011 |
| WO | 2012065086 | A1 | 5/2012 |
| WO | 2012129201 | A1 | 9/2012 |
| WO | 2013057500 | A1 | 4/2013 |
| WO | 2013088147 | A1 | 6/2013 |
| WO | 2013173835 | A1 | 11/2013 |
| WO | 2013188427 | A1 | 12/2013 |
| WO | 2014210036 | A1 | 12/2014 |
| WO | WO 2015/009604 | A1 | 1/2015 |
| WO | 2015157636 | A1 | 10/2015 |
| WO | 2015188839 | A1 | 12/2015 |
| WO | 2015189356 | A1 | 12/2015 |
| WO | 2015189357 | A1 | 12/2015 |
| WO | 2016053338 | A1 | 4/2016 |
| WO | 2016096903 | A1 | 6/2016 |
| WO | 2018081473 | A1 | 5/2018 |
| WO | WO 2018/129332 | A1 | 7/2018 |
| WO | WO 2018/182817 | A1 | 10/2018 |
| WO | WO 2018/209115 | A1 | 11/2018 |
| WO | WO 2018/226714 | A1 | 12/2018 |

OTHER PUBLICATIONS

Glassman, et al. (1979) "Cryopreservation of Human Lymphocytes: A Brief Review and Evaluation of an Automated Liquid Nitrogen Freezer", Transfusion, 19(2): 178-81. (Year: 1979).*

Gladstone, et al. (2014) "Infusion of cryopreserved autologous lymphocytes using a standard peripheral i.v., catheter" Bone Marrow Transplant, 49(8): 1119-20. (Year: 2014).*

International Search Report and Written Opinion for International Patent Application No. PCT/US2017/058610, dated Mar. 8, 2018, 13 pages.

Axelsson et al., "Cryopreserved peripheral blood mononuclear cells are suitable for the assessment of immunological markers in type 1 diabetic children", Cryobiology, Aug. 2008, 57, 201-208.

Chang et al., "Emerging concepts in immunotherapt T-cell metabolism as a therapeutic target", Nat. Immunol., Apr. 2016, 17(4), 364-368.

Dudley, et al.,"Cancer Regression and Autoimmunity in Patients After Clonal Repopulation with Antitumor Lymphocytes", Science, Oct. 2002, 298, 850-54.

Dudley et al., "Generation of Tumor-Infiltrating Lymphocyte Cultures for Use in Adoptive Transfer Therapy for Melanoma Patients," J Immunother., 2003: 26(4): 332-342.

Dudley, et at., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Dudley, et al., "Adoptive Cell Therapy for Patients with Metastatic Melanoma: Evaluation of Intensive Myeloablative Chemoradiation Preparative Regimens", J. Clin. Oncol., Nov. 2008, 26(32), 5233-39.

Gassner, et al., "Fludarabine modulates composition and function of the T Cell pool in patients with chronic lymphocytic leukaemia", Cancer. Immunol. Immunother., 2011, 60, 75-85.

Gattinoni, et al., "Adoptive immunotherapy for cancer: building on success", Nat. Rev. Immunol. May 2006, 6(5), 383-393.

Goff et al., "Tumor Infiltrating Lymphocyte Therapy for Metastatic Melanoma: Analysis of Tumors Resected for TIL", J. Immunother, Oct. 2010, 33(8), 840-847.

Goff SL, et al., Prospective Evaluation Comparing Intensity of Lymphodepletion Before Adoptive Transfer of Tumor-Infiltrating Lymphocytes for Patients With Metastatic Melanoma. J Clin Oncol. Jul. 10, 2016;34(20):2389-79.

Jia He et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.

Jin et al., "Simplified method of the growth of human tumor infiltrating lymphocytes in gas-permiable flasks to numbers needed for patient treatment", J. Immunotherapy, 2012, 35:283-292.

Muranski, et al., "Increased intensity lymphodepletion and adoptive immunotherapy—how far can we go?", Nat. Clin. Pract. Oncol., Dec. 2006, 3, 668-681.

Riddell, et al., "Restoration of Viral Immunity in Immunodeficient Humans by the Adoptive Transfer of T Cell Clones", Science, Jul. 1992, 257, 238-41.

Rosenberg, "IL-2: The First Effective Immunotherapy for Human Cancer," The Journal of Immunology, col. 192, No. 12, Jun. 6, 2014.

Sadeghi, et al., "Rapid expansion of T cells: Effects of culture and cryopreservation and improtance of short-term cell recovery", Acta Oncologica 2013, 52, 978-986.

Tran et al., "Minimally Cultured tumor-infiltrating lymphocytes display optimal characteristics for adoptive cell therapy", 2008, J. Immunother., Oct. 2008 31(8), 742-751.

Tsoukas et al., "Activation of resting T lymphocytes by anti-CD3 (T3) antibodies in the absence of monocytes", J. Immunol. 1985, 135, 1719.

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Besser, et al., "Adoptive Transfer of Tumor-Infiltrating Lymphocytes inPatients with Metastatic Melanoma: Intent-to-Treat Analysis and Efficacy after Failure to Prior Immunotherapies"; Clin Cancer Res, 19(17):0F1-0F9 (2013).

Donia M, et al.. Simplified protocol for clinical-grade tumor-infiltrating lymphocyte manufacturing with use of the Wave bioreactor. Cytotherapy. Aug. 2014;16(8):1117-20. doi: 10.1016/j.jcyt.2014.02.004; PubMed PMID: 2483184.

Donia, et al., "Characterization and Comparison of 'Standard' and 'Young' Tumour-Infiltrating Lymphocytes for Adoptive Cell Therapy at a Danish Translational Research Institution"; Scandinavian Journal of Immunology, 75, 157-157 (2012).

Dudley et al., "CD8+ Enriched "Young" Tumor Infiltrating Lymphocytes Can Mediate Regression of Metastatic Melanoma" Clin Cancer Res, 16:6122-6131 (2010).

Henning AL, et al.. Measurement of T-Cell Telomere Length Using Amplified-Signal FISH Staining and Flow Cytometry. Curr Protoc Cytom. Jan. 5, 2017;79:7.47.1-7.47.10. doi: 10.1002/cpcy.11. PubMed PMID 28055115.

Hinrichs CS, Rosenberg SA. Exploiting the curative potential of adoptive T-cell therapy for cancer. Immunol Rev. Jan. 2014;257(1):56-71. doi:10.1111/imr.12132. Review. PubMed PMID: 24329789; PubMed Central PMCID: PMC3920180.

Huang et al., "Survival, Persistence, and Progressive Differentiation of Adoptively Transferred Tumor-Reactive T Cells Associated with Tumor Regression"; J. Immunother, 28(3), 258-267 (2005).

Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.

Rosenberg SA, Dudley ME. Adoptive cell therapy for the treatment of patients with metastatic melanoma. Curr Opin Immunol. Apr. 2009;21(2):233-40.

Rufer N, et al.. Telomere length dynamics in human lymphocyte subpopulations measured by flow cytometry. Nat Biotechnol. Aug. 1998;16(8):743-7. PubMed PMID: 970277.

Shen X,et al.. Persistence of tumor infiltrating lymphocytes in adoptive immunotherapy correlates with telomere length. J Immunother. Jan. 2007;30(1):123-9. PubMed PMID:17198091; PubMed Central PMCID: PMC2151201.

(56) References Cited

OTHER PUBLICATIONS

Somerville RP, et al.. Clinical scale rapid expansion of lymphocytes for adoptive cell transfer therapy in the WAVE® bioreactor. J Transl Med. Apr. 4, 2012;10:69.
Zhou J, et al.. Telomere length of transferred lymphocytes correlates with in vivo persistence and tumor regression in melanoma patients receiving cell transfer therapy. J Immunol. Nov. 15, 2005;175(10):7046-52. PubMed PMID: 16272366; PubMed Central PMCID: PMC135131.
Zhou, et al., "Persistence of Multiple Tumor-Specific T-Cell Clones Is Associated with Complete Tumor Regression in a Melanoma Patient Receiving Adoptive Cell Transfer Therapy"; J. Immunother, 28, 53-62 (2005).
Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65. doi: 10.4049/jimmunol.0901101. Epub Nov. 30, 2009. PubMed PMID: 19949105.
Chang et al., "Metabolic competition in the tumor microenvironment is a driver of cancer progression", Cell. Sep. 10, 2015; 162(6): pp. 1229-1241.
Ye et al., "Engineered artificial antigen presenting cells facilitate direct and efficient expansion of tumor infiltrating lymphocytes", Journal of Translational Medicine 2011, 9:131, pp. 1-13.
Frank et al., "Remarkably Stable Tumor-Infiltrating Lymphocytes (TIL) for Infusion Phenotype Following Cryopreservation", Nov. 6, 2016, Retrieved from the Internet: http://www.iovance.com/wp-content/uploads/2017/05/LION16701_Frank_POSTER3_final-0005.
Hasan et al., "Artificial Antigen Presenting Cells: An Off the Shelf Approach for Generation of Desirable T-Cell Populations for Broad Application of Adoptive Immunotherapy", Adv Genet Eng, 2015, 4:3.
Wang & Riviere, "Manufacture of tumor- and virus-specific T lymphocytes for adoptive cell therapies", Cancer Gene Therapy, 2015, 22: 85-94.
U.S. Appl. No. 17/459,988, filed Aug. 27, 2021.
U.S. Appl. No. 17/148,475, filed Jan. 13, 2021, now allowed.
U.S. Appl. No. 17/148,508, filed Jan. 13, 2021, now allowed.
Andersen, R. et al.Long-Lasting Complete Responses in Patients with Metastatic Melanoma after Adoptive Cell Therapy with Tumor-Infiltrating Lymphocytes and an Attenuated I L2 Regimen; Published OnlineFirst Mar. 22, 2016; 12 pages.
Goff, Stephanie L. et al.; Tumor Infiltrating Lymphocyte Therapy for Metastatic Melanoma: Analysis of Tumors Resected for TIL; J. Immunother; vol. 33, No. 8, Oct. 2010, 8 pages.
U.S. Appl. No. 15/863,634, filed Jan. 5, 2018, now U.S. Pat. No. 10,894,063.
U.S. Appl. No. 15/874,718, filed Jan. 18, 2018, now U.S. Pat. No. 10,166,257.
U.S. Appl. No. 15/892,311, filed Feb. 8, 2018, now U.S. Pat. No. 10,130,659.
U.S. Appl. No. 16/136,147, filed Sep. 19, 2018, now U.S. Pat. No. 10,272,113.
U.S. Appl. No. 16/136,157, filed Sep. 19, 2018, now U.S. Pat. No. 10,420,799.
U.S. Appl. No. 16/201,957, filed Nov. 27, 2018, now U.S. Pat. No. 10,398,734.
U.S. Appl. No. 16/192,707, filed Nov. 15, 2018, now U.S. Pat. No. 10,537,595.
U.S. Appl. No. 16/425,746, filed May 29, 2019, now U.S. Pat. No. 10,639,330.
U.S. Appl. No. 16/203,467, filed Nov. 28, 2018, now U.S. Pat. No. 10,463,697.
U.S. Appl. No. 16/203,478, filed Nov. 28, 2018, now U.S. Pat. No. 10,363,273.
U.S. Appl. No. 16/425,767, filed May 29, 2019, now U.S. Pat. No. 10,695,372.
U.S. Appl. No. 16/425,778, filed May 29, 2019, now U.S. Pat. No. 10,646,517.
U.S. Appl. No. 16/746,416, filed Jan. 17, 2020, now U.S. Pat. No. 10,653,723.
U.S. Appl. No. 16/848,361, filed Apr. 14, 2020, now U.S. Pat. No. 10,905,718.
U.S. Appl. No. 16/848,386, filed Apr. 14, 2020, now U.S. Pat. No. 10,953,046.
U.S. Appl. No. 16/848,454, filed Apr. 14, 2020, now U.S. Pat. No. 10,946,044.
U.S. Appl. No. 16/848,426, filed Apr. 14, 2020, now U.S. Pat. No. 10,953,047.
U.S. Appl. No. 16/848,442, filed Apr. 14, 2020, now U.S. Pat. No. 10,933,094.
U.S. Appl. No. 16/848,474, filed Apr. 14, 2020, now U.S. Pat. No. 10,946,045.
U.S. Appl. No. 16/879,711, filed May 20, 2020, now U.S. Pat. No. 10,925,900.
U.S. Appl. No. 17/110,207, filed Dec. 2, 2020, now U.S. Pat. No. 11,083,752.
U.S. Appl. No. 17/127,768, filed Dec. 18, 2020, now U.S. Pat. No. 11,007,225.
U.S. Appl. No. 17/127,840, filed Dec. 18, 2020, now U.S. Pat. No. 11,052,116.
U.S. Appl. No. 17/127,790, filed Dec. 18, 2020, now U.S. Pat. No. 11,007,226.
U.S. Appl. No. 17/127,795, filed Dec. 18, 2020, now U.S. Pat. No. 11,052,115.
U.S. Appl. No. 17/147,073, filed Jan. 12, 2021, now U.S. Pat. No. 11,013,770.
U.S. Appl. No. 17/147,080, filed Jan. 12, 2021.
U.S. Appl. No. 17/147,090, filed Jan. 12, 2021, now U.S. Pat. No. 11,040,070.
U.S. Appl. No. 17/147,096, filed Jan. 12, 2021.
U.S. Appl. No. 17/326,088, filed May 20, 2021, now U.S. Pat. No. 11,202,803.
U.S. Appl. No. 17/382,831, filed Jul. 22, 2021.
U.S. Appl. No. 17/383,272, filed Jul. 22, 2021, now U.S. Pat. No. 11,202,804.
U.S. Appl. No. 17/383,276, filed Jul. 22, 2021.
U.S. Appl. No. 17/383,280, filed Jul. 22, 2021.
U.S. Appl. No. 17/480,525, filed Sep. 21, 2021.
U.S. Appl. No. 17/480,534, filed Sep. 21, 2021.
U.S. Appl. No. 17/480,587, filed Sep. 21, 2021.
U.S. Appl. No. 17/480,596, filed Sep. 21, 2021.
U.S. Appl. No. 15/751,440, filed Feb. 8, 2018, now U.S. Pat. No. 11,026,974.
U.S. Appl. No. 15/892,331, filed Feb. 8, 2018, now U.S. Pat. No. 10,517,894.
U.S. Appl. No. 17/225,993, filed Apr. 8, 2021, now U.S. Pat. No. 11,058,728.
U.S. Appl. No. 17/233,290, filed Apr. 16, 2021, now allowed.
U.S. Appl. No. 17/233,295, filed Apr. 16, 2021, now U.S. Pat. No. 11,123,371.
U.S. Appl. No. 17/233,299, filed Apr. 16, 2021, now U.S. Pat. No. 11,141,438.
U.S. Appl. No. 17/480,900, filed Sep. 21, 2021.
U.S. Appl. No. 17/480,916, filed Sep. 21, 2021.
U.S. Appl. No. 17/480,919, filed Sep. 21, 2021.
U.S. Appl. No. 17/480,935, filed Sep. 21, 2021.
U.S. Appl. No. 17/480,941, filed Sep. 21, 2021.
U.S. Appl. No. 17/548,502, filed Dec. 11, 2021.
U.S. Appl. No. 17/548,504, filed Dec. 11, 2021.
U.S. Appl. No. 17/547,190, filed Dec. 9, 2021.
U.S. Appl. No. 17/547,192, filed Dec. 9, 2021.
U.S. Appl. No. 15/940,901, filed Mar. 29, 2018, now U.S. Pat. No. 10,918,666.
U.S. Appl. No. 17/041,305, filed Sep. 24, 2020.
U.S. Appl. No. 17/110,179, filed Dec. 2, 2020.
U.S. Appl. No. 17/147,412, filed Jan. 12, 2021.
U.S. Appl. No. 17/148,475, filed Jan. 13, 2021, now U.S. Pat. No. 11,168,303.
U.S. Appl. No. 17/148,508, filed Jan. 13, 2021, now U.S. Pat. No. 11,168,304.
U.S. Appl. No. 17/353,430, filed Jun. 21, 2021.
U.S. Appl. No. 16/618,039, filed Nov. 27, 2019.
U.S. Appl. No. 16/211,159, filed Dec. 5, 2018.

(56) References Cited

OTHER PUBLICATIONS

Besser, Michal J et al. "Clinical responses in a phase II study using adoptive transfer of short-term cultured tumor infiltration lymphocytes in metastatic melanoma patients." Clinical cancer research : an official journal of the American Association for Cancer Research vol. 16,9 (2010): 2646-55.
Bajgain, P. et al., "Optimizing the production of suspension cells using the G-Rex "M" series", Molecular Therapy—Methods and Clinical Development, vol. 1, Jan. 1, 2014.
Ikarashi, H et al., "Solid-phase anti-CD3 antibody activation and cryopreservation of human tumor-infiltrating lymphocytes derived from epithelial ovarian cancer", Japanese Journal of Cancer Research, vol. 83, No. 12, Dec. 1, 1992.
Forget, Marie-Andrée et al. "The beneficial effects of a gas-permeable flask for expansion of Tumor-Infiltrating lymphocytes as reflected in their mitochondrial function and respiration capacity." Oncoimmunology vol. 5,2 e1057386. Jun. 5, 2015.
Itzhaki, Orit et al. "Establishment and large-scale expansion of minimally cultured "young" tumor infiltrating lymphocytes for adoptive transfer therapy." Journal of immunotherapy (Hagerstown, Md. : 1997) vol. 34,2 (2011): 212-20.
Junker, Niels et al. "Bimodal ex vivo expansion of T cells from patients with head and neck squamous cell carcinoma: a prerequisite for adoptive cell transfer." Cytotherapy vol. 13,7 (2011): 822-34.
Lee et al., "Tumor-Infiltrating Lymphocytes in Melanoma", Curr Oncol Rep. Aug. 2012, 14, 468-474.
Nguyen, Linh T et al. "Expansion and characterization of human melanoma tumor-infiltrating lymphocytes (TILs)." PloS one vol. 5,11 e13940. Nov. 10, 2010.
Rosenberg, S A et al. "A new approach to the adoptive immunotherapy of cancer with tumor-infiltrating lymphocytes." Science (New York, N.Y.) vol. 233,4770 (1986): 1318-21.
Rosenberg, S A et al. "Treatment of patients with metastatic melanoma with autologous tumor-infiltrating lymphocytes and interleukin 2." Journal of the National Cancer Institute vol. 86,15 (1994): 1159-66.
Rosenberg, S A et al. "Use of tumor-infiltrating lymphocytes and interleukin-2 in the immunotherapy of patients with metastatic melanoma. A preliminary report." The New England journal of medicine vol. 319,25 (1988): 1676-80.
Wilson Wolf—Superior Cell Culture Devices, G-Rex, Oct. 31, 2016.
Ye, et al., "Engineered Artificial antigen presenting cells facilitate direct and efficient expansion of tumor infiltrating lymphocytes", J. Translat. Med. 2011, 9(131), 13 pages.
Akkök, C. A. et al. "Use of different DMSO concentrations for cryopreservation of autologous peripheral blood stem cell grafts does not have any major impact on levels of leukocyte- and platelet-derived soluble mediators." Cytotherapy vol. 11,6 (2009): 749-60.
Baruch et al., "Adoptive T cell therapy: An overview of obstacles and opportunities : ACT Obstacles and Opportunities", Cancer, vol. 123, No. S11, May 19, 2017, pp. 2154-2162.
Chacon et al., "Co-stimulation through 4-1BB/CD137 Improves the Expansion and Fundtion of CD8+ Melanoma Tumor-Infiltrating Lymphocytes for Adoptive T-Cell Therapy", PLOS One, vol. 8, No. 4, Apr. 1, 2013, 25 pages.
Forget et al., "Activation and propagation of tumor infiltrating lymphocytes on clinical-grade designer artificial antigen presenting cells for adoptive immunotherapy of melanoma", Journal of Immunotherapy, vol. 37 No. 9, Nov. 1, 2014, pp. 448-460.
Hall et al., "Expansion of tumor-infiltrating lymphocytes (TIL) from human pancreatic tumors", Journal for ImmunoTherapy of Cancer, vol. 4, No. 1, pp. 1-12.
Hernandez-Chacon et al., "Costimulation through the CD137/4-1BB Pathway Protects Human Melanoma Tumor-infiltrating Lymphocytes from Activation-induced Cell Death and Enhances Antitumor Effector Function", Journal of ImmunoTherapy, vol. 34, No. 3, Apr. 1, 2011, pp. 236-250.
International Search Report and Written Opinion for International Patent Application No. PCT/US2018/012633 dated May 25, 2018, 14 pages.
International Search Report and Written Opinion for International Patent Application No. PCT/US2018/040474 dated Nov. 14, 2018, 17 pages.
Iyer, R.K. et al., "Industrializing Autologous Adoptive Immunotherapies: Manufacturing Advances and Challenges", Frontiers in Medicine, vol. 5, May 23, 2018.
Jin et al., "Enhanced clinical-scale manufacturing of TCR transduced T-cells using closed culture system modules", Journal of Transactional Medicine, col. 16. No. 1, Jan. 24, 2018.
Klapper, J.A. et al., "Single-pass, closed-system rapid expansion of lymphocyte cultures for adoptive cell therapy", Journal of Immunological Methods, vol. 345, No. 1-2, Jun. 30, 2009.
Merhavi-Shoham et al., "Adoptive Cell Therapy for Metastatic Melanoma", Cancer Journal, vol. 23, No. 1, Jan. 1, 2017.
Mullinax et al., "Combination of Ipilimumab and Adoptive Cell Therapy with Tumor-Infiltrating Lymphocytes for Patients with Metastatic Melanoma", Frontiers in Oncology, vol. 8, Mar. 2, 2018.
Rohaan et al., "Adoptive transfer of tumor-infiltrating lymphocytes in melanoma: a viable treatment option", Journal for Immunotherapy of Cancer, vol. 6, No. 1, Oct. 3, 2018, pp. 1-16.
Rosenberg SA, et al. "Durable Complete Responses in Heavily Pretreated Patients with Metastatic Melanoma Using T Cell Transfer Immunotherapy", Clinical Cancer research, vol. 17, No. 13, Jul. 1, 2011 pp. 4550-4557.
Van den Bossche, J. et al. "Metabolic Characterization of Polarized M1 and M2 Bone Marrow-derived Macrophages Using Real-time Extracellular Flux Analysis." Journal of visualized experiments : JoVE ,105 53424. Nov. 28, 2015.
Wardell et al., "A cryopreserved tumor infiltrating lymphocyte (TIL) product for LN-44", Nov. 8, 2017, retrieved from the Internet: URL: http://www.iovance.com/wp-content/uploads/2017/11/SITC2017_Seth_poster_FINAL_SWDE_PRINT_7Nov2017.pdf.
Zuliani, T. et al., "Value of large scale expansion of tumor infiltrating lymphocytes in a compartmentalised gas-permiable bag: interests for adoptive immunotherapy", Journal of Translational Medicine, vol. 9, No. 1, May 16, 2011.

\* cited by examiner

*Figure 1*

Table 1.

| Tumor Type | | Fresh Product | Cryopreserved Product | |
|---|---|---|---|---|
| | | post-Harvest | post-Thaw | post-restimulation |
| Malignant Melanoma (M1053T) REP | OxPhos (pmol/min) | | | |
| | Basal respiration | 17.5 ± 4.4 | 9.5 ± 4.9 | 22.5 ± 2.5 |
| | SRC | 19.3 ± 9.0 | 27.5 ± 12.1 | 16.8 ± 2.6 |
| | SRC (% of basal) | 210.6 ± 51.4 | 389.8 ± 127.4 | 174.7 ± 11.3 |
| | Glycolysis (mpH/min) | | | |
| | Basal glycolysis | 31.1 ± 4.4 | 22.5 ± 1.2 | 103.1 ± 5.4 |
| | Glycolytic Reserve | 26.4 ± 5.5 | 20.7 ± 2.2 | 15.9 ± 7.7 |
| | Glycolytic Res (% of basal) | 185.1 ± 17.6 | 192.0 ± 9.9 | 115.5 ± 7.4 |

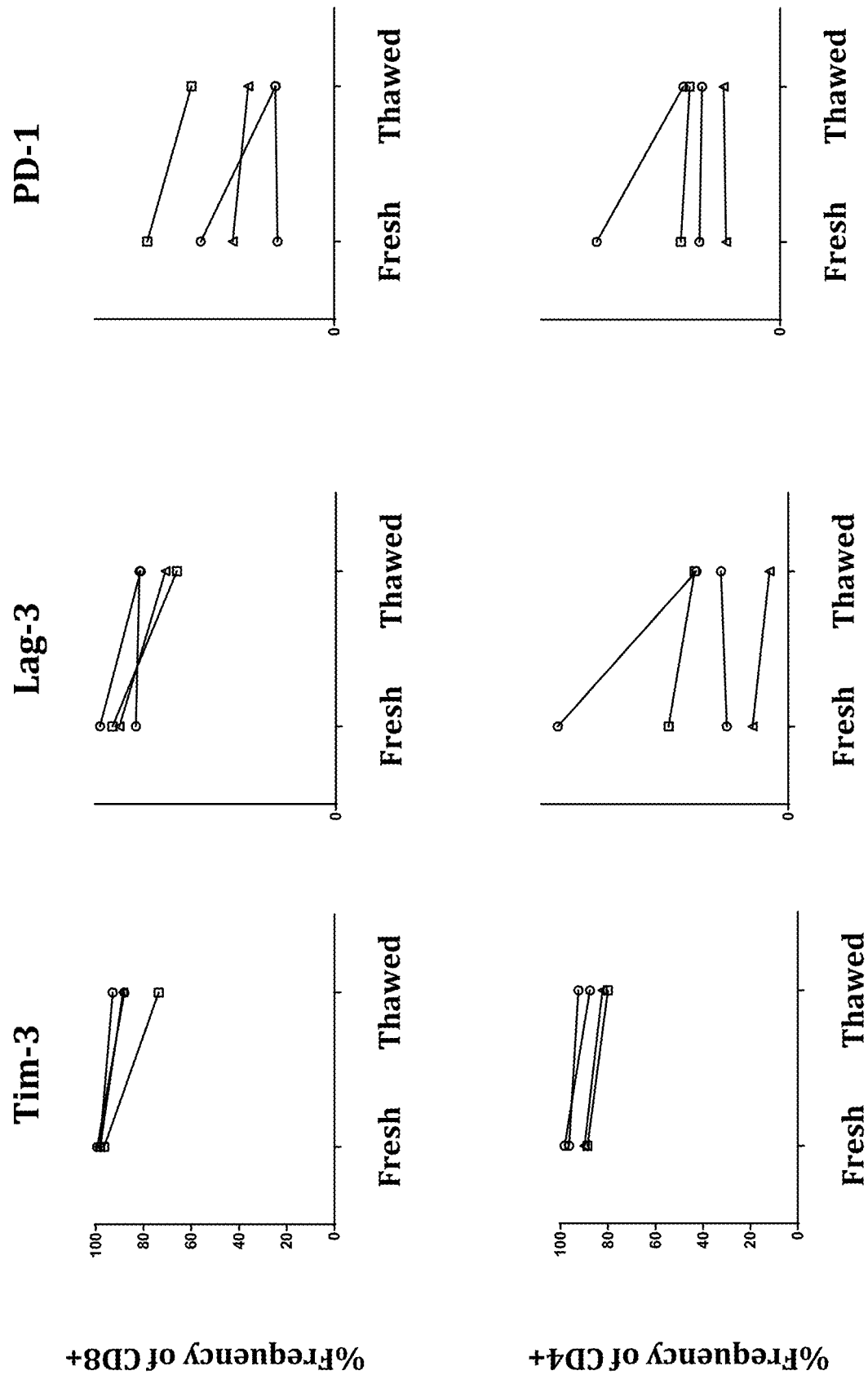

Figure 11

Process 1C : 43-55 Days for Steps A - E

1. STEP A

Obtain Patient Tumor Sample

2. STEP B

Fragmentation and First Expansion
11 to 21 days

3. STEP C

First Expansion to Second Expansion Transition
Optional Storage until Selection

4. STEP D

Second Expansion
IL-2, OKT-3, antigen-presenting feeder cells
Optionally repeated one or more times

5. STEP E

Harvest TILS from Step D

6. STEP F

Final Formulation and/or Transfer to Infusion Bag

*Figure 15*

| TUBE NAME | SSRC | S/Live CD8 CD8+ Freq. of Parent | S/Live CD8 CD8 Freq. of Parent | S/Live CD8 Q1: CCR7+ CD45RA+ Freq of Parent | S/Live CD8 Q2: CCR7+ CD45RA- Freq of Parent | S/Live CD8 Q3: CCR7- CD45RA- Freq of Parent | S/Live CD8 Q4: CCR7- CD45RA+ Freq of Parent | S/Live CD8 Q5: CD28- CD57+ Freq of Parent | S/Live CD8 Q6: CD28+ CD57+ Freq of Parent | S/Live CD8 Q7: CD28+ CD57- Freq of Parent | S/Live CD8 Q8: CD28- CD57- Freq of Parent |
|---|---|---|---|---|---|---|---|---|---|---|---|
| 1.00E+08 | Not Rested | 3.01 | 95 | 0.53 | 0.53 | 52 | 46.9 | 2.16 | 0.23 | 7.87 | 89.8 |
| 4.00E+08 | Not Rested | 2.83 | 95 | 0.47 | 0.69 | 56.7 | 42.2 | 2.51 | 0.32 | 8.19 | 89 |
| 8.00E+08 | Not Rested | 2.85 | 95.6 | 0.34 | 0.58 | 55.4 | 43.6 | 2.26 | 0.29 | 8.37 | 89.1 |
| 1.00E+08 | Rested | 5.78 | 90.4 | 1.1 | 0.78 | 55.1 | 43 | 1.05 | 0.32 | 12.8 | 85.9 |
| 4.00E+08 | Rested | 5.74 | 90 | 0.86 | 0.82 | 61.1 | 37.2 | 1.11 | 0.32 | 13.6 | 85 |
| 8.00E+08 | Rested | 7.64 | 87.5 | 1.42 | 1.07 | 60.5 | 37 | 1.18 | 0.32 | 17.1 | 81.4 |

SEQUENCE LISTING

<160> NUMBER OF SEQ ID NOS: 8

<210> SEQ ID NO 1
<211> LENGTH: 450
<212> TYPE: PRT
<213> ORGANISM: Artificial Sequence
<220> FEATURE:

<223> OTHER INFORMATION: Synthetic Muromonab heavy chain

<400> SEQUENCE: 1

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Gly Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Synthetic Muromonab light chain

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 3
<211> LENGTH: 134
<212> TYPE: PRT
<213> ORGANISM: Artificial Sequence
<220> FEATURE:
<223> OTHER INFORMATION: Synthetic recombinant human IL-2 (rhIL-2)

<400> SEQUENCE: 3

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30
```

-continued

```
Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
 50                  55                  60

Lys Pro Leu Glu Glu Val Leu Asn Leu Ala Gln Ser Lys Asn Phe His
 65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
                100                 105                 110

Ala Thr Ile Val Glu Phe Leu Asn Arg Trp Ile Thr Phe Cys Gln Ser
            115                 120                 125

Ile Ile Ser Thr Leu Thr
        130
```

<210> SEQ ID NO 4
<211> LENGTH: 132
<212> TYPE: PRT
<213> ORGANISM: Artificial Sequence
<220> FEATURE:
<223> OTHER INFORMATION: Synthetic Aldesleukin

<400> SEQUENCE: 4

```
Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130
```

<210> SEQ ID NO 5
<211> LENGTH: 130
<212> TYPE: PRT
<213> ORGANISM: Artificial Sequence
<220> FEATURE:
<223> OTHER INFORMATION: Synthetic recombinant human IL-4 (rhIL-4)

<400> SEQUENCE: 5

```
Met His Lys Cys Asp Ile Thr Leu Gln Glu Ile Ile Lys Thr Leu Asn
 1               5                  10                  15

Ser Leu Thr Glu Gln Lys Thr Leu Cys Thr Glu Leu Thr Val Thr Asp
                20                  25                  30

Ile Phe Ala Ala Ser Lys Asn Thr Thr Glu Lys Glu Thr Phe Cys Arg
            35                  40                  45

Ala Ala Thr Val Leu Arg Gln Phe Tyr Ser His His Glu Lys Asp Thr
```

```
                50                  55                  60
Arg Cys Leu Gly Ala Thr Ala Gln Gln Phe His Arg His Lys Gln Leu
 65                  70                  75                  80

Ile Arg Phe Leu Lys Arg Leu Asp Arg Asn Leu Trp Gly Leu Ala Gly
                 85                  90                  95

Leu Asn Ser Cys Pro Val Lys Glu Ala Asn Gln Ser Thr Leu Glu Asn
                100                 105                 110

Phe Leu Glu Arg Leu Lys Thr Ile Met Arg Glu Lys Tyr Ser Lys Cys
                115                 120                 125

Ser Ser
    130

<210> SEQ ID NO 6
<211> LENGTH: 153
<212> TYPE: PRT
<213> ORGANISM: Artificial Sequence
<220> FEATURE:
<223> OTHER INFORMATION: Synthetic recombinant human IL-7 (rhIL-7)

<400> SEQUENCE: 6

Met Asp Cys Asp Ile Glu Gly Lys Asp Gly Lys Gln Tyr Glu Ser Val
 1               5                  10                  15

Leu Met Val Ser Ile Asp Gln Leu Leu Asp Ser Met Lys Glu Ile Gly
                20                  25                  30

Ser Asn Cys Leu Asn Asn Glu Phe Asn Phe Lys Arg His Ile Cys
                35                  40                  45

Asp Ala Asn Lys Glu Gly Met Phe Leu Phe Arg Ala Ala Arg Lys Leu
 50                  55                  60

Arg Gln Phe Leu Lys Met Asn Ser Thr Gly Asp Phe Asp Leu His Leu
 65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
                100                 105                 110

Ser Leu Glu Glu Asn Lys Ser Leu Lys Glu Gln Lys Lys Leu Asn Asp
                115                 120                 125

Leu Cys Phe Leu Lys Arg Leu Leu Gln Glu Ile Lys Thr Cys Trp Asn
                130                 135                 140

Lys Ile Leu Met Gly Thr Lys Glu His
145                 150

<210> SEQ ID NO 7
<211> LENGTH: 115
<212> TYPE: PRT
<213> ORGANISM: Artificial Sequence
<220> FEATURE:
<223> OTHER INFORMATION: Synthetic recombinant human IL-15 (rhIL-15)

<400> SEQUENCE: 7

Met Asn Trp Val Asn Val Ile Ser Asp Leu Lys Lys Ile Glu Asp Leu
 1               5                  10                  15

Ile Gln Ser Met His Ile Asp Ala Thr Leu Tyr Thr Glu Ser Asp Val
                20                  25                  30

His Pro Ser Cys Lys Val Thr Ala Met Lys Cys Phe Leu Leu Glu Leu
                35                  40                  45

Gln Val Ile Ser Leu Glu Ser Gly Asp Ala Ser Ile His Asp Thr Val
 50                  55                  60
```

-continued

```
Glu Asn Leu Ile Ile Leu Ala Asn Asn Ser Leu Ser Ser Asn Gly Asn
 65                  70                  75                  80

Val Thr Glu Ser Gly Cys Lys Glu Cys Glu Glu Leu Glu Glu Lys Asn
                 85                  90                  95

Ile Lys Glu Phe Leu Gln Ser Phe Val His Ile Val Gln Met Phe Ile
            100                 105                 110

Asn Thr Ser
        115

<210> SEQ ID NO 8
<211> LENGTH: 132
<212> TYPE: PRT
<213> ORGANISM: Artificial Sequence
<220> FEATURE:
<223> OTHER INFORMATION: Synthetic recombinant human IL-21 (rhIL-21)

<400> SEQUENCE: 8

Met Gln Asp Arg His Met Ile Arg Met Arg Gln Leu Ile Asp Ile Val
  1               5                  10                  15

Asp Gln Leu Lys Asn Tyr Val Asn Asp Leu Val Pro Glu Phe Leu Pro
                 20                  25                  30

Ala Pro Glu Asp Val Glu Thr Asn Cys Glu Trp Ser Ala Phe Ser Cys
             35                  40                  45

Phe Gln Lys Ala Gln Leu Lys Ser Ala Asn Thr Gly Asn Asn Glu Arg
         50                  55                  60

Ile Ile Asn Val Ser Ile Lys Lys Leu Lys Arg Lys Pro Pro Ser Thr
 65                  70                  75                  80

Asn Ala Gly Arg Arg Gln Lys His Arg Leu Thr Cys Pro Ser Cys Asp
                 85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
        115                 120                 125

Ser Glu Asp Ser
        130
```

RESTIMULATION OF CRYOPRESERVED TUMOR INFILTRATING LYMPHOCYTES

CROSS REFERENCE TO RELATED APPLICATIONS

This application is a continuation of U.S. patent application Ser. No. 17/233,290, filed Apr. 16, 2021, now U.S. Pat. No. 11,179,419, which is a continuation of U.S. patent application Ser. No. 15/751,440, filed Feb. 8, 2018, now U.S. Pat. No. 11,026,974, which is a U.S. National Stage entry of International Patent Application No. PCT/US2017/058610, filed Oct. 26, 2017, which claims priority to U.S. Provisional Patent Application Nos. 62/413,283 and 62/413,387, filed Oct. 26, 2016, entitled "Expansion of Tumor-Infiltrating Lymphocytes and Methods of Using the Same," and U.S. Provisional Patent Application No. 62/415,452, filed Oct. 31, 2016, entitled "RESTIMULATION OF CRYOPRESERVED TUMOR INFILTRATING LYMPHOCYTES," which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Aug. 27, 2021, titled 116983-5004-U506_Sequence_Listing.txt and is 14,042 kilobytes in size.

BACKGROUND OF THE INVENTION

Treatment of bulky, refractory cancers using adoptive transfer of tumor infiltrating lymphocytes (TILs) represents a powerful approach to therapy for patients with poor prognoses. Gattinoni, et al., *Nat. Rev. Immunol.* 2006, 6, 383-393. A large number of TILs are required for successful immunotherapy, and a robust and reliable process is needed for commercialization. This has been a challenge to achieve because of technical, logistical, and regulatory issues with cell expansion. IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. REP can result in a 1,000-fold expansion of TILs over a 14-day period, although it requires a large excess (e.g., 200-fold) of irradiated allogeneic peripheral blood mononuclear cells (PBMCs), often from multiple donors, as feeder cells, as well as anti-CD3 antibody (OKT3) and high doses of IL-2. Dudley, et al., *J. Immunother.* 2003, 26, 332-42.

TILs that have undergone an REP procedure have produced successful adoptive cell therapy following host immunosuppression in patients with melanoma. Current infusion acceptance parameters rely on readouts of the composition of TILs (e.g., CD28, CD8, or CD4 positivity) and on fold expansion and viability of the REP product.

However, current REP protocols, as well as current TIL expansion protocols generally, give little insight into the health of the TIL that will be infused into the patient. T cells undergo a profound metabolic shift during the course of their maturation from naïve to effector T cells (see Chang, et al., *Nat. Immunol.* 2016, 17, 364, hereby expressly incorporated in its entirety, and in particular for the discussion and markers of anaerobic and aerobic metabolism). For example, naïve T cells rely on mitochondrial respiration to produce ATP, while mature, healthy effector T cells such as TIL are highly glycolytic, relying on aerobic glycolysis to provide the bioenergetics substrates they require for proliferation, migration, activation, and anti-tumor efficacy.

In addition, these expanded cell populations can be cryopreserved, leading to ease of use, long-term storage for multiple reinfusions into patients with recurrent disease, and other considerations. However, current infusion acceptance parameters rely on readouts of the composition of TILs and on fold-expansion and viability of the expanded TIL based product. These measures give little insight into the health of the TIL that will be infused into the patient, and little is known about the effects of cryopreservation on TIL populations.

Accordingly, the present invention is directed to methods for expanding and re-stimulating TIL populations that lead to improved phenotype and increased metabolic health of the TILs and towards methods of assaying for TIL populations to determine suitability for more efficacious infusion after re-stimulation.

BRIEF SUMMARY OF THE INVENTION

The present invention provides methods for expanding TILs in larger, sometimes therapeutic, populations in combination with optional cryopreservation.

According to the present disclosure, a method for expanding tumor infiltrating lymphocytes (TILs) into a therapeutic population of TILs comprising the following steps is provided:

(i) obtaining a first population of TILs from a tumor resected from a patient;

(ii) performing a first expansion by culturing the first population of TILs in a cell culture medium comprising IL-2 to produce a second population of TILs; and (iii) performing a second expansion by supplementing the cell culture medium of the second population of TILs with additional IL-2, OKT-3, and antigen presenting cells (APCs), to produce a third population of TILs, wherein the third population of TILs is at least 50-fold or 100-fold greater in number than the second population of TILs, and wherein the second expansion is performed for at least 14 days in order to obtain the third population of TILs, wherein the third population of TILs is a therapeutic population of TILs which comprises an increased subpopulation of effector T cells and/or central memory T cells relative to the second population of TILs.

In some embodiments, the method further comprises:

(iv) performing an additional second expansion by supplementing the cell culture medium of the third population of TILs with additional IL-2, additional OKT-3, and additional APCs, wherein the additional second expansion is performed for at least 14 days to obtain a larger therapeutic population of TILs than obtained in step (iii), wherein the larger therapeutic population of TILs comprises an increased subpopulation of effector T cells and/or central memory T cells relative to the third population of TILs.

In some embodiments, after step (iii), the cells are removed from the cell culture and cryopreserved in a storage medium prior to performing step (iv).

In some embodiments, the cells are thawed prior to performing step (iv).

In some embodiments, step (iv) is repeated one to four times in order to obtain sufficient TILs in the therapeutic population of TILs for a therapeutically effective dosage of the TILs.

In some embodiments, steps (i) through (iii) or (iv) are performed within a period of about 40 days to about 50 days. In some embodiments, steps (i) through (iii) or (iv) are performed within a period of about 42 days to about 48 days. In some embodiments, steps (i) through (iii) or (iv) are performed within a period of about 42 days to about 45 days. In some embodiments, steps (i) through (iii) or (iv) are performed within about 44 days.

In some embodiments, the cells from steps (iii) or (iv) express CD4, CD8, and TCR αβ at levels similar to freshly harvested cells.

In some embodiments, the antigen presenting cells are peripheral blood mononuclear cells (PBMCs). In some embodiments, the PBMCs are added to the cell culture on any of days 9 through 17 in step (iii).

In some embodiments, the effector T cells and/or central memory T cells in the therapeutic population of TILs in step (iv) exhibit one or more characteristics selected from the group consisting of expression of CD27, expression of CD28, longer telomeres, increased CD57 expression, and decreased CD56 expression, relative to effector T cells and/or central memory T cells in the third population of cells.

In some embodiments, the effector T cells and/or central memory T cells exhibit increased CD57 expression and decreased CD56 expression.

In some embodiments, the APCs are artificial APCs (aAPCs).

In some embodiments, the method further comprises the step of transducing the first population of TILs with an expression vector comprising a nucleic acid encoding a high-affinity T cell receptor.

In some embodiments, the method further comprises the step of transducing the first population of TILs with an expression vector comprising a nucleic acid encoding a chimeric antigen receptor (CAR) comprising a single chain variable fragment antibody fused with at least one endodomain of a T-cell signaling molecule.

In some embodiments, the therapeutic population of TILs are infused into a patient.

In some embodiments, step (iii) further comprises a step of removing the cells from the cell culture medium.

In some embodiments, step (iii) is repeated one to four times in order to obtain sufficient TILs in the therapeutic population of TILs for a therapeutically effective dosage of the TILs.

In some embodiments, the number of TILs sufficient for a therapeutically effective dosage is from about $2.3 \times 10^{10}$ to about $13.7 \times 10^{10}$.

The present disclosure also provides a population of expanded TILs made according to the method of claim 1.

The present disclosure also provides a population of expanded TILs made according to the method of claim 1, wherein the expanded TILs have at least a two-fold increase in basal glycolysis as compared to thawed cryopreserved TILs.

The present disclosure also provides methods for assessing the metabolic activity of a TIL cell population made according to the methods described herein, comprising measuring the basal glycolysis of the cells.

The present disclosure also provides methods for assessing the metabolic activity of a TIL cell population made according to the methods described herein, comprising measuring the basal respiration of the cells.

The present disclosure also provides methods for assessing the metabolic activity of a TIL cell population made according to the methods described herein, comprising measuring the spare respiratory capacity (SRC) of the cells.

The present disclosure also provides methods for assessing the metabolic activity of a TIL cell population made according to the methods described herein, comprising measuring the glycolytic reserve of the cells.

The present disclosure also provides a method for expanding tumor infiltrating lymphocytes (TILs) into a therapeutic population of TILs comprising:
  (i) performing a first expansion by culturing a first population of TILs from a tumor resected from a patient in a cell culture medium comprising IL-2 to obtain a second population of TILs; and
  (ii) performing a second expansion by supplementing the cell culture medium of the second population of TILs with additional IL-2, OKT-3, and antigen presenting cells (APCs) to obtain a third population of TILs, wherein the third population of TILs is at least 50-fold or 100-fold greater in number than the second population of TILs, and wherein the second expansion is performed for at least 14 days in order to obtain the third population of TILs, wherein the third population of TILs is a therapeutic population of TILs which comprises an increased subpopulation of effector T cells and/or central memory T cells relative to the second population of TILs.

In some embodiments, the method further comprises:
  (iii) performing an additional second expansion of the third population of TILs by supplementing the cell culture medium of the third population of TILs with additional IL-2, additional OKT-3, and additional APCs, wherein the additional second expansion is performed for at least 14 days to obtain a larger therapeutic population of TILs than obtained in step (ii), wherein the larger therapeutic population of TILs exhibits an increased subpopulation of effector T cells and/or central memory T cells relative to the third population of TILs.

In some embodiments, the cells from the cell culture medium in step (ii) are removed and cryopreserved in a storage medium prior to step (iii).

In some embodiments, the cells are thawed prior to step (iii).

In some embodiments, step (ii) is repeated one to four times in order to obtain sufficient TILs in the therapeutic population of TILs for a therapeutically effective dosage of the TILs.

In some embodiments, the number of TILs sufficient for a therapeutically effective dosage is from about $2.3 \times 10^{10}$ to about $13.7 \times 10^{10}$.

In some embodiments, the APCs are peripheral blood mononuclear cells (PBMCs).

In some embodiments, the effector T cells and/or central memory T cells exhibit one or more characteristics selected from the group consisting of expression of CD27, expression of CD28, longer telomeres, increased CD57 expression, and decreased CD56 expression, relative to effector T cells and/or central memory T cells in the third population of cells.

In some embodiments, the effector T cells and/or central memory T cells exhibit increased CD57 expression and decreased CD56 expression.

The present disclosure also provides a method for treating a subject with cancer comprising administering expanded tumor infiltrating lymphocytes (TILs) comprising:
(i) obtaining a first population of TILs from a tumor resected from a patient;
(ii) performing a first expansion by culturing the first population of TILs in a cell culture medium comprising IL-2 to produce a second population of TILs;
(iii) performing a second expansion by supplementing the cell culture medium of the second population of TILs with additional IL-2, OKT-3, and antigen presenting cells (APCs), to produce a third population of TILs, wherein the third population of TILs is at least 50-fold or 100-fold greater in number than the second population of TILs, and wherein the second expansion is performed for at least 14 days in order to obtain the third population of TILs, wherein the third population of TILs is a therapeutic population of TILs which comprises an increased subpopulation of effector T cells and/or central memory T cells relative to the second population of TILs; and
(iv) administering a therapeutically effective dosage of the third population of TILs to the patient.

In some embodiments, the method further comprises prior to step (iv) a step of performing an additional second expansion by supplementing the cell culture medium of the third population of TILs with additional IL-2, additional OKT-3, and additional APCs, wherein the additional second expansion is performed for at least 14 days to obtain a larger therapeutic population of TILs than obtained in step (iii), wherein the larger therapeutic population of TILs comprises an increased subpopulation of effector T cells and/or central memory T cells relative to the third population of TILs.

In some embodiments, after step (ii) the cells are removed from the cell culture medium and cryopreserved in a storage medium prior to the additional second expansion according to the methods described herein.

In some embodiments, the cells are thawed prior to the additional second expansion of according to the methods described herein.

In some embodiments, step (iii) is repeated one to four times in order to obtain sufficient TILs in the therapeutic population of TILs for a therapeutically effective dosage of the TILs.

In some embodiments, the number of TILs sufficient for a therapeutically effective dosage is from about $2.3 \times 10^{10}$ to about $13.7 \times 10^{10}$.

In some embodiments, the APCs are peripheral blood mononuclear cells (PBMCs).

In some embodiments, the effector T cells and/or central memory T cells exhibit one or more characteristics selected from the group consisting of expression of CD27, expression of CD28, longer telomeres, increased CD57 expression, and decreased CD56 expression, relative to effector T cells and/or central memory T cells in the third population of cells.

In some embodiments, the effector T cells and/or central memory T cells exhibit increased CD57 expression and decreased CD56 expression.

In some embodiments, the cancer is selected from the group consisting of melanoma, cervical cancer, head and neck cancer, glioblastoma, ovarian cancer, sarcoma, pancreatic cancer, bladder cancer, breast cancer, triple negative breast cancer, and non-small cell lung carcinoma.

The present disclosure also provides a method for treating a subject with cancer comprising administering expanded tumor infiltrating lymphocytes (TILs) comprising:
(i) performing a first expansion by culturing a first population of TILs from a tumor resected from a patient in a cell culture medium comprising IL-2 to obtain a second population of TILs;
(ii) performing a second expansion by supplementing the cell culture medium of the second population of TILs with additional IL-2, OKT-3, and antigen presenting cells (APCs) to obtain a third population of TILs, wherein the third population of TILs is at least 50-fold or 100-fold greater in number than the second population of TILs, and wherein the second expansion is performed for at least 14 days in order to obtain the third population of TILs, wherein the third population of TILs is a therapeutic population of TILs which comprises an increased subpopulation of effector T cells and/or central memory T cells relative to the second population of TILs; and
(iii) administering a therapeutically effective dosage of the therapeutic population of TILs to the patient.

In some embodiments, the method further comprises prior to step (iii) a step of performing an additional second expansion by supplementing the cell culture medium of the third population of TILs with additional IL-2, additional OKT-3, and additional APCs, wherein the additional second expansion is performed for at least 14 days to obtain a larger therapeutic population of TILs than obtained in step (ii), wherein the larger therapeutic population of TILs comprises an increased subpopulation of effector T cells and/or central memory T cells relative to the third population of TILs.

In some embodiments, the cells from the cell culture medium in step (ii) are removed and cryopreserved in a storage medium prior to the additional second expansion as described herein.

In some embodiments, the cells are thawed prior to the additional second expansion as described herein.

In some embodiments, step (ii) is repeated one to four times in order to obtain sufficient TILs in the therapeutic population of TILs for a therapeutically effective dosage of the TILs.

In some embodiments, the number of TILs sufficient for a therapeutically effective dosage is from about $2.3 \times 10^{10}$ to about $13.7 \times 10^{10}$.

In some embodiments, the APCs are peripheral blood mononuclear cells (PBMCs).

In some embodiments, the effector T cells and/or central memory T cells exhibit one or more characteristics selected from the group consisting of expression of CD27, expression of CD28, longer telomeres, increased CD57 expression, and decreased CD56 expression, relative to effector T cells and/or central memory T cells in the third population of cells.

In some embodiments, the effector T cells and/or central memory T cells exhibit increased CD57 expression and decreased CD56 expression.

In some embodiments, the cancer is selected from the group consisting of melanoma, cervical cancer, head and neck cancer, glioblastoma, ovarian cancer, sarcoma, pancreatic cancer, bladder cancer, breast cancer, triple negative breast cancer, and non-small cell lung carcinoma.

The present invention also provides assay methods for determining TIL viability. The present disclosure provides methods for assaying TILs for viability by expanding tumor infiltrating lymphocytes (TILs) into a larger population of TILs comprising:

(i) obtaining a first population of TILs which has been previously expanded;
(ii) performing a first expansion by culturing the first population of TILs in a cell culture medium comprising IL-2 to produce a second population of TILs; and
(iii) performing a second expansion by supplementing the cell culture medium of the second population of TILs with additional IL-2, OKT-3, and antigen presenting cells (APCs), to produce a third population of TILs, wherein the third population of TILs is at least 50-fold or 100-fold greater in number than the second population of TILs, and wherein the second expansion is performed for at least 14 days in order to obtain the third population of TILs, wherein the third population of TILs comprises an increased subpopulation of effector T cells and/or central memory T cells relative to the second population of TILs, and wherein the third population is further assayed for viability.

In some embodiments, the method further comprises:
(iv) performing an additional second expansion by supplementing the cell culture medium of the third population of TILs with additional IL-2, additional OKT-3, and additional APCs, wherein the additional second expansion is performed for at least 14 days to obtain a larger population of TILs than obtained in step (iii), wherein the larger population of TILs comprises an increased subpopulation of effector T cells and/or central memory T cells relative to the third population of TILs, and wherein the third population is further assayed for viability.

In some embodiments, prior to step (i), the cells are cryopreserved.

In some embodiments, the cells are thawed prior to performing step (i).

In some embodiments, step (iv) is repeated one to four times in order to obtain sufficient TILs for analysis.

In some embodiments, steps (i) through (iii) or (iv) are performed within a period of about 40 days to about 50 days.

In some embodiments, steps (i) through (iii) or (iv) are performed within a period of about 42 days to about 48 days.

In some embodiments, steps (i) through (iii) or (iv) are performed within a period of about 42 days to about 45 days.

In some embodiments, steps (i) through (iii) or (iv) are performed within about 44 days.

In some embodiments, the cells from steps (iii) or (iv) express CD4, CD8, and TCR αβ at levels similar to freshly harvested cells.

In some embodiments, the antigen presenting cells are peripheral blood mononuclear cells (PBMCs).

In some embodiments, the PBMCs are added to the cell culture on any of days 9 through 17 in step (iii).

In some embodiments, the effector T cells and/or central memory T cells in the larger population of TILs in step (iv) exhibit one or more characteristics selected from the group consisting of expression of CD27, expression of CD28, longer telomeres, increased CD57 expression, and decreased CD56 expression, relative to effector T cells, and/or central memory T cells in the third population of cells.

In some embodiments, the effector T cells and/or central memory T cells exhibit increased CD57 expression and decreased CD56 expression.

In some embodiments, the APCs are artificial APCs (aAPCs).

In some embodiments, the method further comprises the step of transducing the first population of TILs with an expression vector comprising a nucleic acid encoding a high-affinity T cell receptor.

In some embodiments, the step of transducing occurs before step (i).

In some embodiments, the method further comprises the step of transducing the first population of TILs with an expression vector comprising a nucleic acid encoding a chimeric antigen receptor (CAR) comprising a single chain variable fragment antibody fused with at least one endodomain of a T-cell signaling molecule.

In some embodiments, the step of transducing occurs before step (i).

In some embodiments, the TILs are assayed for viability.

In some embodiments, the TILs are assayed for viability after cryopreservation.

In some embodiments, the TILs are assayed for viability after cryopreservation and after step (iv).

According to the present disclosure, a method for assaying TILs for viability and/or further use in administration to a subject. In some embodiments, the method for assay tumor infiltrating lymphocytes (TILs) comprises:
(i) obtaining a first population of TILs;
(ii) performing a first expansion by culturing the first population of TILs in a cell culture medium comprising IL-2 to produce a second population of TILs; and
(iii) performing a second expansion by supplementing the cell culture medium of the second population of TILs with additional IL-2, OKT-3, and antigen presenting cells (APCs), to produce a third population of TILs, wherein the third population of TILs is at least 50-fold greater in number than the second population of TILs;
(iv) harvesting, washing, and cryopreserving the third population of TILs;
(v) storing the cryopreserved TILs at a cryogenic temperature;
(vi) thawing the third population of TILs to provide a thawed third population of TILs; and
(vii) performing an additional second expansion of a portion of the thawed third population of TILs by supplementing the cell culture medium of the third population with IL-2, OKT-3, and APCs for a reREP period of at least 3 days, wherein the third expansion is performed to obtain a fourth population of TILs, wherein the number of TILs in the fourth population of TILs is compared to the number of TILs in the third population of TILs to obtain a ratio;
(viii) determining based on the ratio in step (vii) whether the thawed population of TILs is suitable for administration to a patient;
(ix) administering a therapeutically effective dosage of the thawed third population of TILs to the patient when the ratio of the number of TILs in the fourth population of TILs to the number of TILs in the third population of TILs is determined to be greater than 5:1 in step (viii).

In some embodiments, the reREP period is performed until the ratio of the number of TILs in the fourth population of TILs to the number of TILs in the third population of TILs is greater than 50:1.

In some embodiments, the number of TILs sufficient for a therapeutically effective dosage is from about $2.3 \times 10^{10}$ to about $13.7 \times 10^{10}$.

In some embodiments, steps (i) through (vii) are performed within a period of about 40 days to about 50 days. In some embodiments, steps (i) through (vii) are performed within a period of about 42 days to about 48 days. In some embodiments, steps (i) through (vii) are performed within a period of about 42 days to about 45 days. In some embodiments, steps (i) through (vii) are performed within about 44 days.

In some embodiments, the cells from steps (iii) or (vii) express CD4, CD8, and TCR αβ at levels similar to freshly harvested cells. In some embodiments the cells are TILs.

In some embodiments, the antigen presenting cells are peripheral blood mononuclear cells (PBMCs). In some embodiments, the PBMCs are added to the cell culture on any of days 9 through 17 in step (iii).

In some embodiments, the effector T cells and/or central memory T cells in the larger population of TILs in steps (iii) or (vii) exhibit one or more characteristics selected from the group consisting of expression of CD27, expression of CD28, longer telomeres, increased CD57 expression, and decreased CD56 expression, relative to effector T cells, and/or central memory T cells in the third population of cells.

In some embodiments, the effector T cells and/or central memory T cells exhibit increased CD57 expression and decreased CD56 expression.

In some embodiments, the APCs are artificial APCs (aAPCs).

In some embodiments, the step of transducing the first population of TILs with an expression vector comprising a nucleic acid encoding a high-affinity T cell receptor.

In some embodiments, the step of transducing occurs before step (i).

In some embodiments, the step of transducing the first population of TILs with an expression vector comprising a nucleic acid encoding a chimeric antigen receptor (CAR) comprising a single chain variable fragment antibody fused with at least one endodomain of a T-cell signaling molecule.

In some embodiments, the step of transducing occurs before step (i).

In some embodiments, the TILs are assayed for viability after step (vii).

The present disclosure also provides further methods for assaying TILs. In some embodiments, the disclosure provides a method for assaying TILs comprising:
(i) obtaining a portion of a first population of cryopreserved TILs;
(ii) thawing the portion of the first population of cryopreserved TILs;
(iii) performing a first expansion by culturing the portion of the first population of TILs in a cell culture medium comprising IL-2, OKT-3, and antigen presenting cells (APCs) for a reREP period of at least 3 days, to produce a second population of TILs, wherein the portion from the first population of TILs is compared to the second population of TILs to obtain a ratio of the number of TILs, wherein the ratio of the number of TILs in the second population of TILs to the number of TILs in the portion of the first population of TILs is greater than 5:1;
(iv) determining based on the ratio in step (iii) whether the first population of TILs is suitable for use in therapeutic administration to a patient;
(v) determining the first population of TILs is suitable for use in therapeutic administration when the ratio of the number of TILs in the second population of TILs to the number of TILs in the first population of TILs is determined to be greater than 5:1 in step (iv).

In some embodiments, the ratio of the number of TILs in the second population of TILs to the number of TILs in the portion of the first population of TILs is greater than 50:1.

In some embodiments, the method further comprises performing expansion of the entire first population of cryopreserved TILs from step (i) according to the methods as described in any of the embodiments provided herein.

In some embodiments, the method further comprises administering the entire first population of cryopreserved TILs from step (i) to the patient.

The present disclosure also provides further methods for assaying TILs. In some embodiments, the disclosure provides a method for assaying TILs comprising:
(i) obtaining a portion of a first population of cryopreserved TILs;
(ii) thawing the portion of the first population of cryopreserved TILs;
(iii) performing a first expansion by culturing the portion of the first population of TILs in a cell culture medium comprising IL-2, OKT-3, and antigen presenting cells (APCs) for a reREP period of at least 3 days, to produce a second population of TILs, wherein the portion from the first population of TILs is compared to the second population of TILs to obtain a ratio of the number of TILs, wherein the ratio of the number of TILs in the second population of TILs to the number of TILs in the portion of the first population of TILs is greater than 5:1;
(iv) determining based on the ratio in step (iii) whether the first population of TILs is suitable for use in therapeutic administration to a patient; and
(v) therapeutically administering the remainder of the first population of TILs to the patient when the ratio of the number of TILs in the second population of TILs to the number of TILs in the first population of TILs is determined to be greater than 5:1 in step (iv).

In some embodiments, the ratio of the number of TILs in the second population of TILs to the number of TILs in the portion of the first population of TILs is greater than 50:1.

In some embodiments, the method further comprises performing expansion of the entire first population of cryopreserved TILs from step (i) according to the methods of any of the preceding claims.

In some embodiments, the method further comprises administering the entire first population of cryopreserved TILs from step (i) to the patient.

In some embodiments, the method further comprised the step of assessing the metabolic health of the second population of TILs.

In some embodiments, the method further comprises the step of assessing the phenotype of the second population of TILs.

In some embodiments, the antigen presenting cells are allogeneic peripheral blood mononuclear cells.

BRIEF DESCRIPTION OF THE DRAWINGS

FIG. 1: Shows the results from Example 1. As the Table shows, following the antigen restimulation rapid expansion protocol ("reREP"), the TILs exhibit a marked enhancement in their glycolytic respiration. SRC=spare respiratory capacity.

FIGS. 6A and 6B: Maintenance of LAG-3 Staining Following Cryopreservation and Thaw. A: LAG-3 staining of CD8 TIL. B: % frequency of regulatory molecules of the CD4 and CD8 populations on fresh and thawed TIL. CD8+TIM-3+ and CD8+LAG-3+ thawed TIL have a lower % than fresh TIL. Mann-Whitney statistical test.

FIG. 15: Fresh versus reREP TIL phenotypes.

DETAILED DESCRIPTION OF THE INVENTION

I. Introduction

Figure 2:
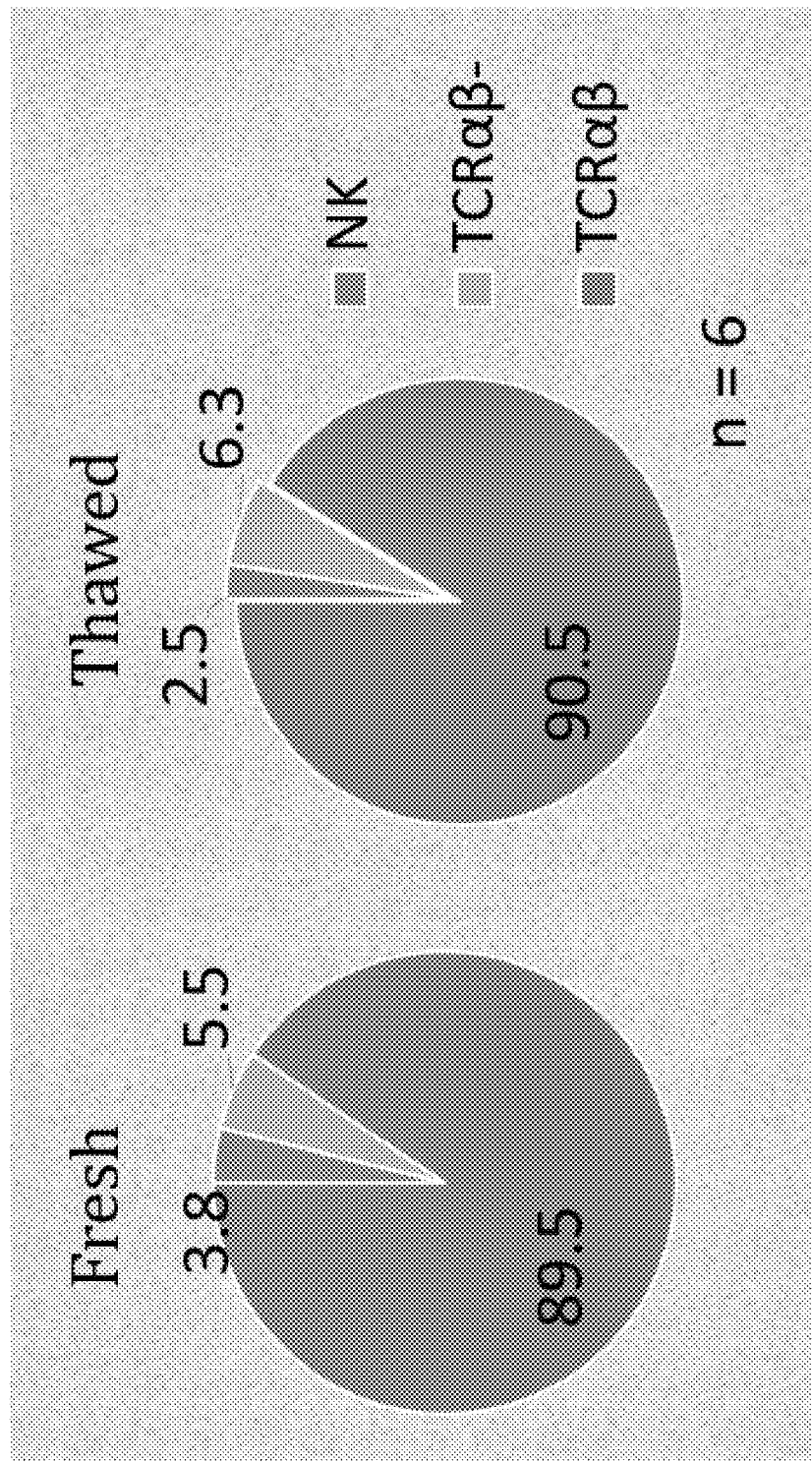
FIG. 2: Composition of fresh vs. thawed TIL. TIL were stained for TCRαβ and CD56 to define T-cell and NK populations. The data shown are averages of 6 individual TILs.
Figure 3:
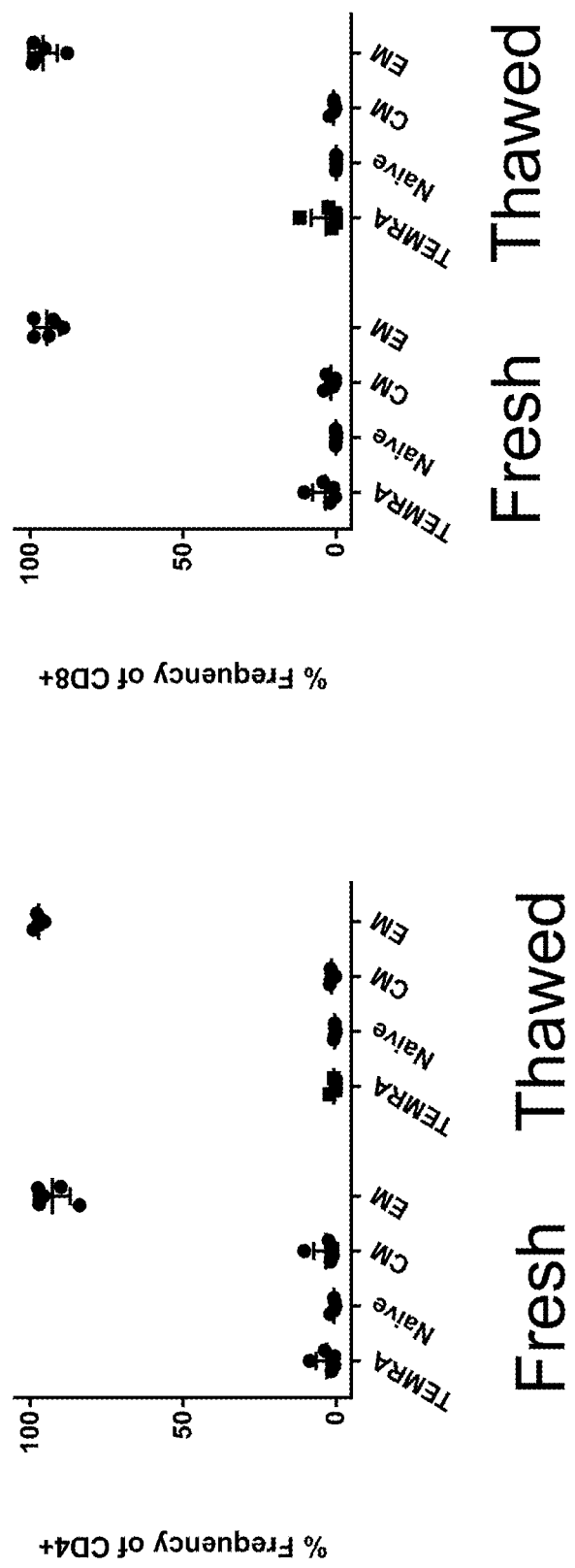
FIG. 3: Memory phenotype is defined by CD45RA and CCR7 Expression. CD4 and CD8 TIL are mainly Effector Memory (EM) This remains the same in the thawed TIL. Each point is one sample analyzed. No significant difference is found in a Wilcoxon matched-pairs signed rank test.
Figure 4:
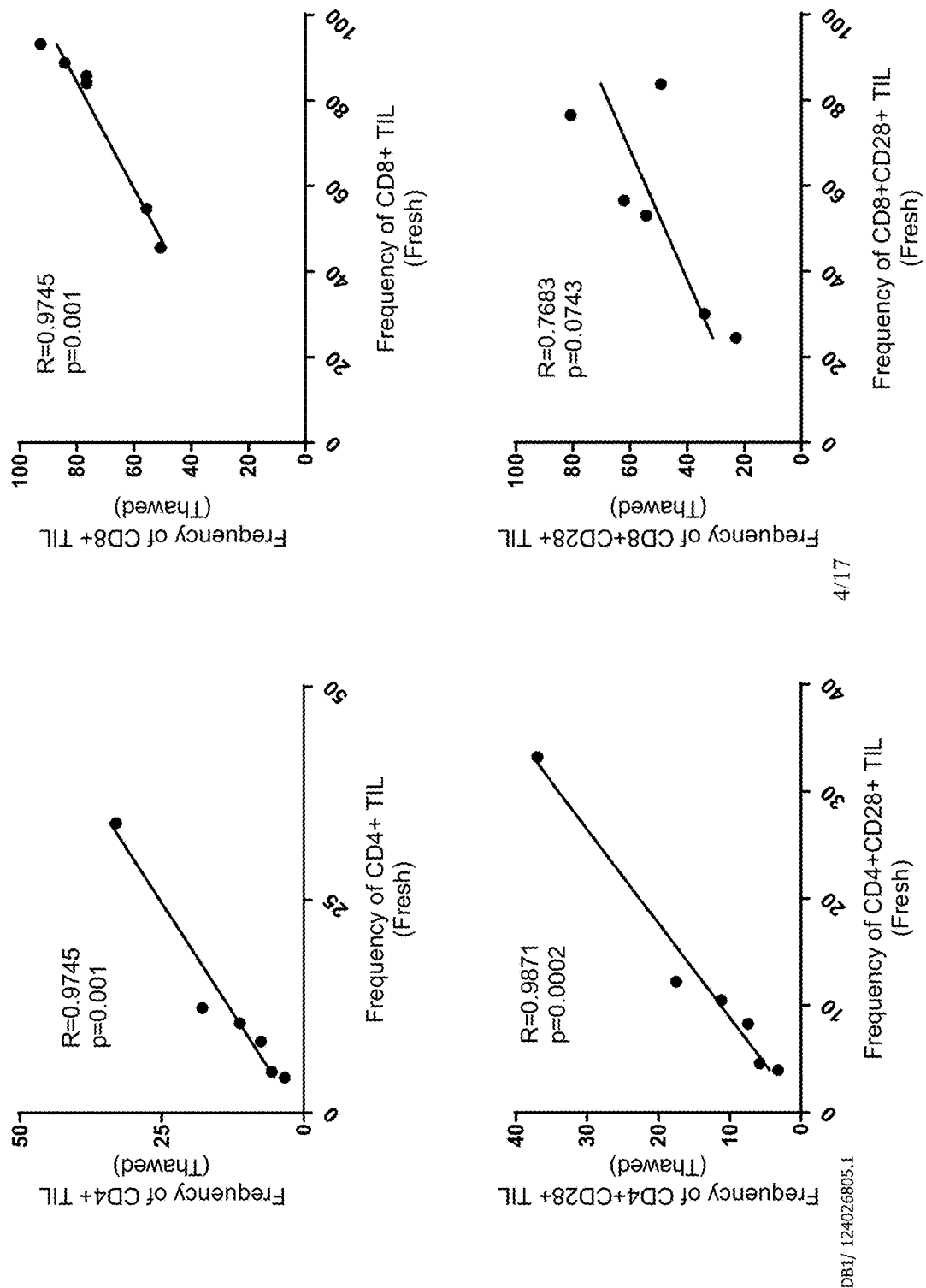
FIG. 4: Pearson's correlation of CD4, CD8, CD4+CD28+, and CD8+CD28+ frequency between fresh and thawed TIL. Cells were stained with above markers. Each dot represents one individual with the fresh value on the x axis and the thawed value on the y axis. The fit line was drawn using linear regression analysis.
Figure 5:
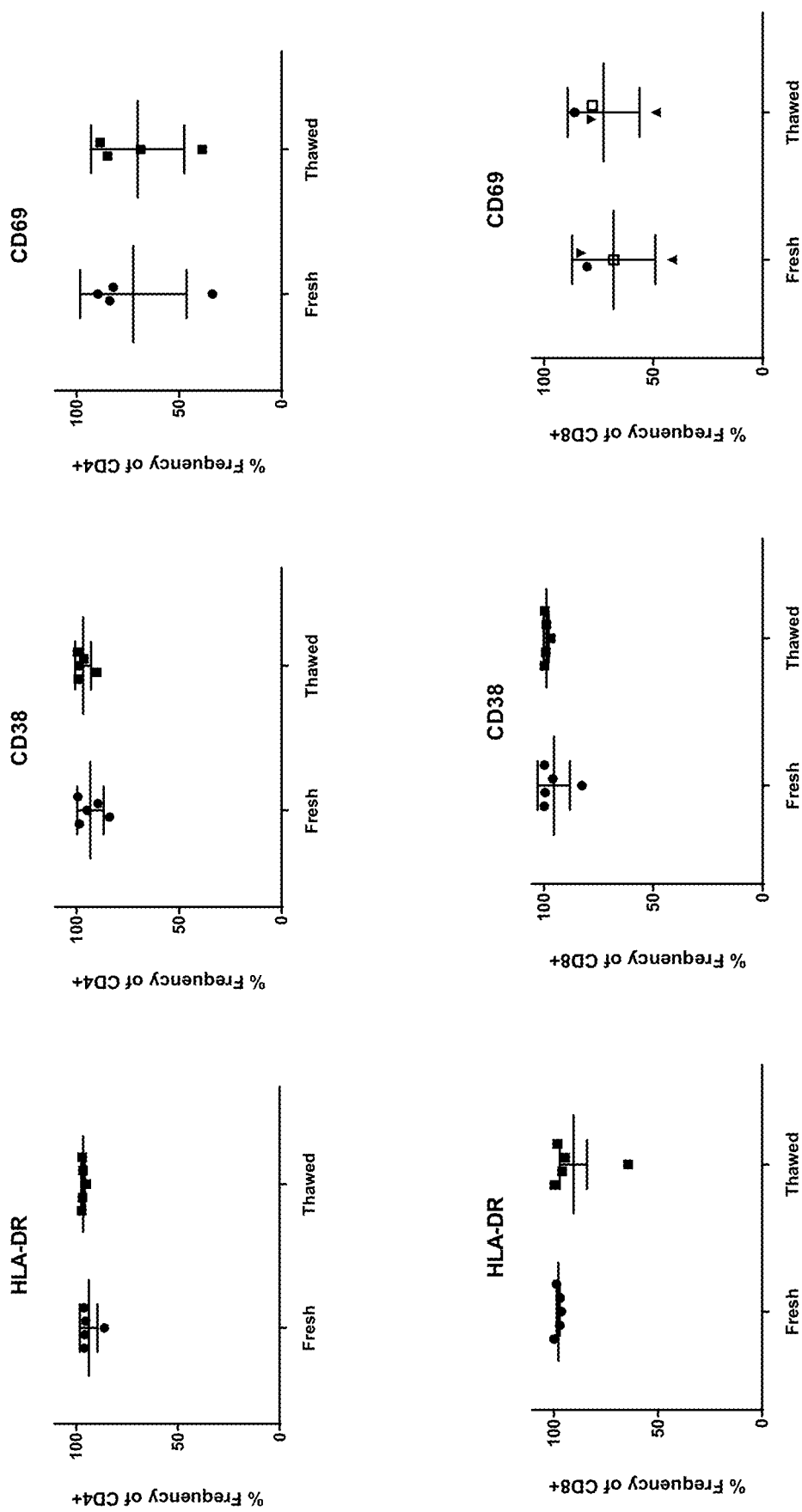
FIG. 5: Comparable Activation Markers on Fresh and Thawed TILs. No significant difference in activation status of fresh vs. thawed TIL was found using a Wilcoxon Matched-Pairs Rank Test. Each point represents one sample analyzed and is shown as mean+/−SEM.
Figure 6A:
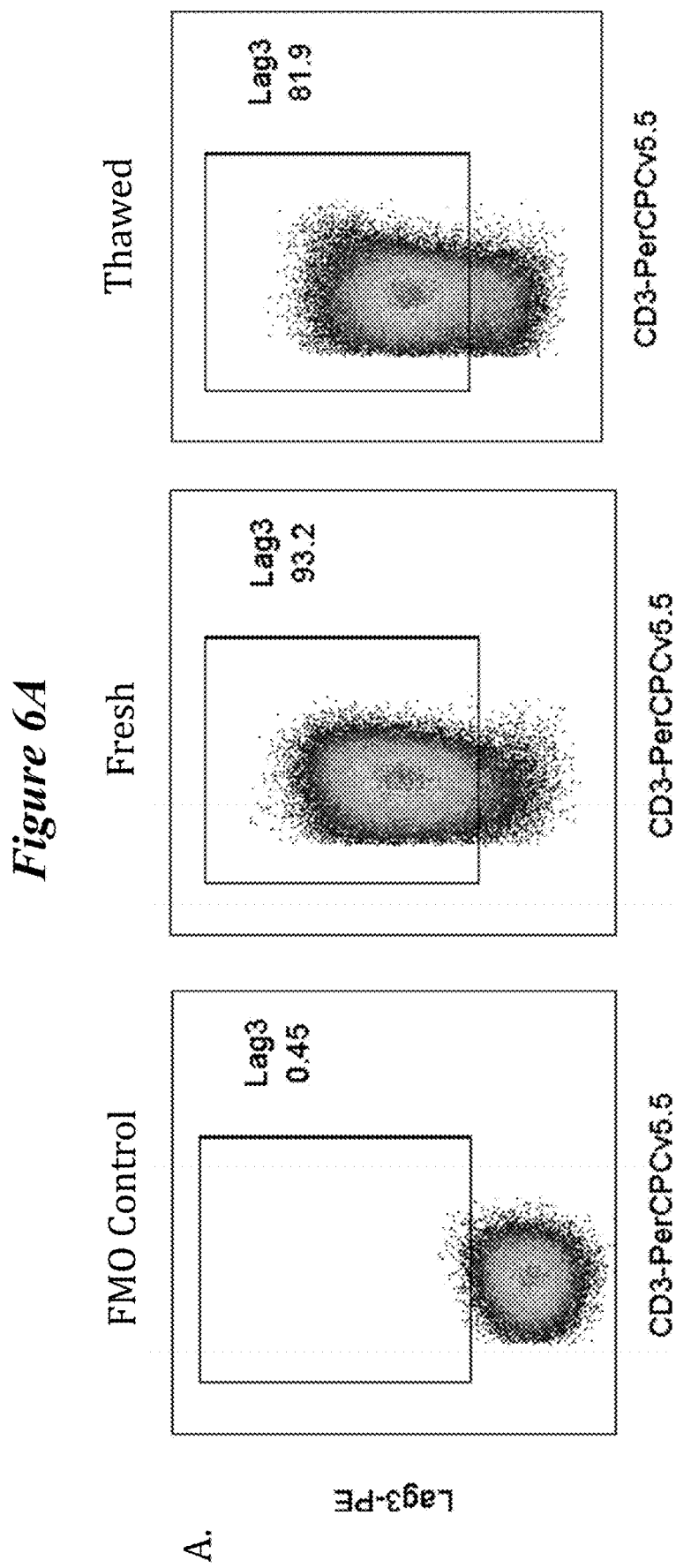
Figure 7:
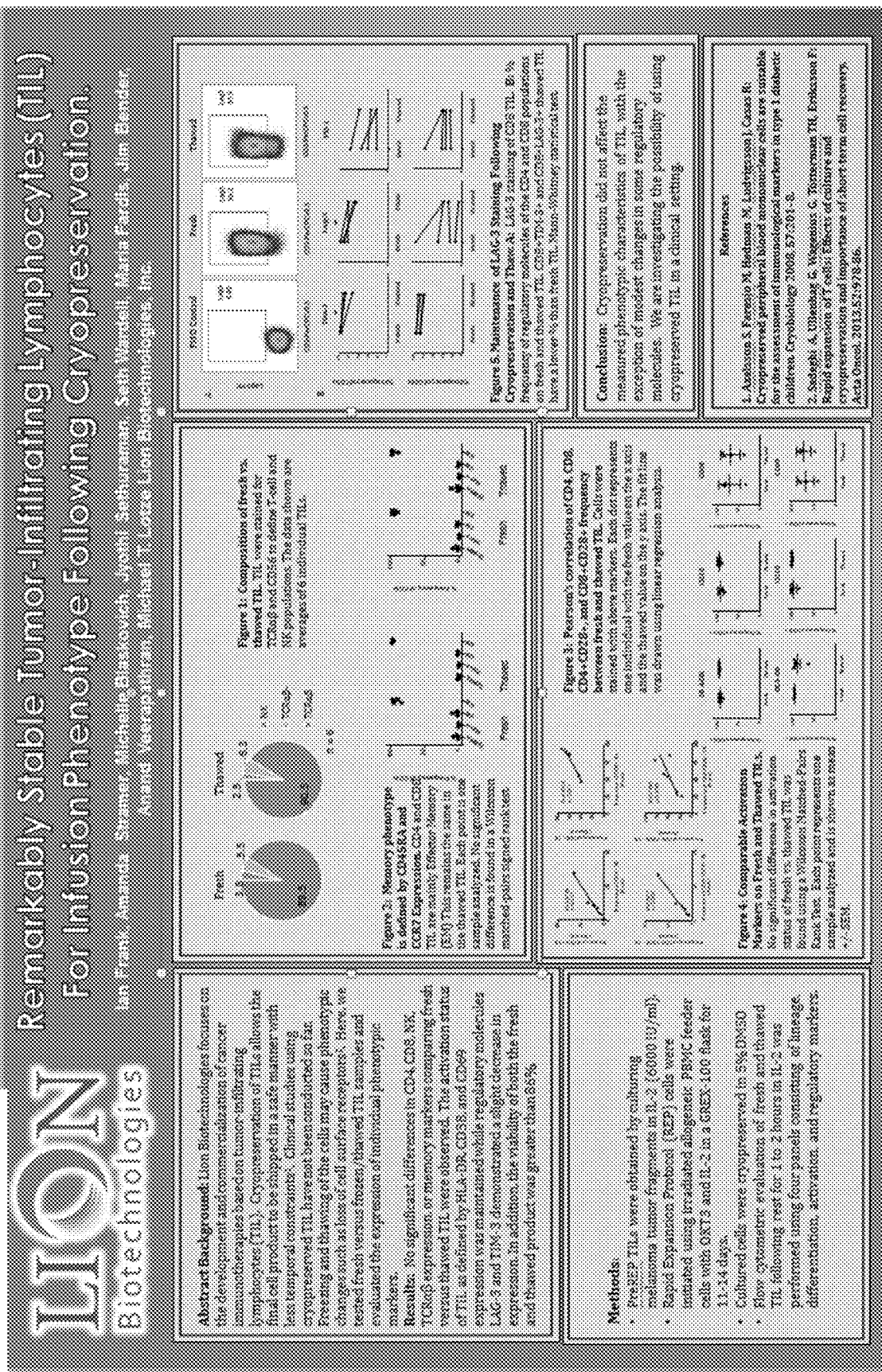
FIG. 7: Remarkably stable tumor-infiltrating lymphocytes (TIL) for infusion phenotype following cryopreservation.

Adoptive cell therapy utilizing TILs cultured ex vivo by the Rapid Expansion Protocol (REP) has produced successful adoptive cell therapy following host immunosuppression in patients with melanoma. Current infusion acceptance parameters rely on readouts of the composition of TILs (e.g., CD28, CD8, or CD4 positivity) and on the numerical folds of expansion and viability of the REP product.

Current REP protocols give little insight into the health of the TIL that will be infused into the patient. T cells undergo a profound metabolic shift during the course of their maturation from naïve to effector T cells (see Chang, et al., Nat. Immunol. 2016, 17, 364, hereby expressly incorporated in its entirety, and in particular for the discussion and markers of anaerobic and aerobic metabolism). For example, naïve T cells rely on mitochondrial respiration to produce ATP, while mature, healthy effector T cells such as TIL are highly glycolytic, relying on aerobic glycolysis to provide the bioenergetics substrates they require for proliferation, migration, activation, and anti-tumor efficacy.

Previous papers report that limiting glycolysis and promoting mitochondrial metabolism in TILs prior to transfer is desirable as cells that are relying heavily on glycolysis will suffer nutrient deprivation upon adoptive transfer which results in a majority of the transferred cells dying. Thus, the art teaches that promoting mitochondrial metabolism might promote in vivo longevity and in fact suggests using inhibitors of glycolysis before induction of the immune response. See Chang et al. (Chang, et al., *Nat. Immunol.* 2016, 17(364), 574-582).

The present invention is directed in preferred aspects to novel methods of augmenting REPs with an additional restimulation protocol, sometimes referred to herein as a "restimulation Rapid Expansion Protocol" or "reREP", which leads surprisingly to expanded memory T cell subsets, including the central memory (CD45RA$^-$CCR7$^+$) or effector memory (CD45RA$^-$CCR7$^-$) phenotypes, and/or to marked enhancement in the glycolytic respiration as compared to freshly harvested TILs or thawed cryopreserved TILs for the restimulated TILs (sometimes referred to herein as "reTILs"). That is, by using a reREP procedure (i.e., a procedure comprising a first expansion and a second expansion) on cryopreserved TILs, patients can receive highly metabolically active, healthy TILs, leading to more favorable outcomes.

The present invention is further directed in some embodiments to methods for evaluating and quantifying this increase in metabolic health. Thus, the present invention provides methods of assaying the relative health of a TIL population using one or more general evaluations of metabolism, including, but not limited to, rates and amounts of glycolysis, oxidative phosphorylation, spare respiratory capacity (SRC) and glycolytic reserve.

Furthermore, the present invention is further directed in some embodiments to methods for evaluating and quantifying this increase in metabolic health. Thus, the present invention provides methods of assaying the relative health of a TIL population using one or more general evaluations of metabolism, including, but not limited to, rates and amounts of glycolysis, oxidative phosphorylation, spare respiratory capacity (SRC), and glycolytic reserve.

In addition, optional additional evaluations include, but are not limited to, ATP production, mitochondrial mass and glucose uptake.

In some cases, the reREP cell population with increased metabolic health are infused into a patient as is generally known in the art.

II. Definitions

By "tumor infiltrating lymphocytes" or "TILs" herein is meant a population of cells originally obtained as white blood cells that have left the bloodstream of a subject and migrated into a tumor. TILs include, but are not limited to, CD8+ cytotoxic T cells (lymphocytes), Th1 and Th17 CD4+ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs, expanded TILs ("REP TILs") as well as "reREP TILs" as discussed herein.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient. TILS may further be characterized by potency—for example, TILS may be considered potent if, for example, interferon (IFN) release is greater than about 50 pg/mL, greater than about 100 pg/mL, greater than about 150 pg/mL, or greater than about 200 pg/mL. Interferon can include interferon gamma (IFNγ).

By "cryopreserved TILs" herein is meant that TILs, either primary, bulk, or expanded (REP TILs), are treated and stored in the range of about −150° C. to −60° C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

By "population of cells" (including TILs) herein is meant a number of cells that share common traits. In general, populations generally range from $1 \times 10^6$ to $1 \times 10^{10}$ in number, with different TIL populations comprising different numbers. For example, initial growth of primary TILs in the presence of IL-2 results in a population of bulk TILs of roughly $1 \times 10^8$ cells. REP expansion is generally done to provide populations of $1.5 \times 10^9$ to $1.5 \times 10^{10}$ cells for infusion.

In general, TILs are initially obtained from a patient tumor sample ("primary TILs") and then expanded into a larger population for further manipulation as described herein, optionally cryopreserved, restimulated as outlined herein and optionally evaluated for phenotype and metabolic parameters as an indication of TIL health.

In general, the harvested cell suspension is called a "primary cell population" or a "freshly harvested" cell population.

In general, as discussed herein, the TILs are initially prepared by obtaining a primary population of TILs from a tumor resected from a patient as discussed herein (the "primary cell population" or "first cell population"). This is followed with an initial bulk expansion utilizing a culturing of the cells with IL-2, forming a second population of cells (sometimes referred to herein as the "bulk TIL population" or "second population").

The term "cytotoxic lymphocyte" includes cytotoxic T (CTL) cells (including $CD8^+$ cytotoxic T lymphocytes and $CD4^+$ T-helper lymphocytes), natural killer T (NKT) cells and natural killer (NK) cells. Cytotoxic lymphocytes can include, for example, peripheral blood-derived α/βTCR-positive or α/βTCR-positive T cells activated by tumor associated antigens and/or transduced with tumor specific chimeric antigen receptors or T-cell receptors, and tumor-infiltrating lymphocytes (TILs).

The term "central memory T cell" refers to a subset of T cells that in the human are CD45RO+ and constitutively express CCR7 (CCR7 hi) and CD62L (CD62 hi). The surface phenotype of central memory T cells also includes TCR, CD3, CD127 (IL-7R), and IL-15R. Transcription factors for central memory T cells include BCL-6, BCL-6B, MBD2, and BMII. Central memory T cells primarily secret IL-2 and CD40L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are CD45R0+, but have lost the constitutive expression of CCR7 (CCR7lo) and are heterogeneous or low for CD62L expression (CD62Llo). The surface phenotype of central memory T cells also includes TCR, CD3, CD127 (IL-7R), and IL-15R. Transcription factors for central memory T cells include BLIMP'. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. CD8+ effector memory T cells carry large amounts of perforin. The term "closed system" refers to a system that is closed to the outside environment. Any closed system appropriate for cell culture methods can be employed with the methods of the present invention. Closed systems include, for example, but are not limited to closed G-containers. Once a tumor segment is added to the closed system, the system is no opened to the outside environment until the TILs are ready to be administered to the patient.

The terms "peripheral blood mononuclear cells" and "PBMCs" refers to a peripheral blood cell having a round nucleus, including lymphocytes (T cells, B cells, NK cells) and monocytes. Preferably, the peripheral blood mononuclear cells are irradiated allogeneic peripheral blood mononuclear cells.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are described herein.

In some embodiments, methods of the present disclosure further include a "pre-REP" stage in which tumor tissue or cells from tumor tissue are grown in standard lab media (including without limitation RPMI) and treated the with reagents such as irradiated feeder cells and anti-CD3 antibodies to achieve a desired effect, such as increase in the number of TILS and/or an enrichment of the population for cells containing desired cell surface markers or other structural, biochemical or functional features. The pre-REP stage may utilize lab grade reagents (under the assumption that the lab grade reagents get diluted out during a later REP stage), making it easier to incorporate alternative strategies for improving TIL production. Therefore, in some embodiments, the disclosed TLR agonist and/or peptide or peptidomimetics can be included in the culture medium during the pre-REP stage. The pre-REP culture can in some embodiments, include IL-2.

The present invention is directed in preferred aspects to novel methods of augmenting REPs with an additional restimulation protocol, sometimes referred to herein as a "restimulation Rapid Expansion Protocol" or "reREP", which leads surprisingly to expanded memory T cell subsets, including the memory effector T cell subset, and/or to marked enhancement in the glycolytic respiration as compared to freshly harvested TILs or thawed cryopreserved TILs for the restimulated TILs (sometimes referred to herein as "reTILs"). That is, by using a reREP procedure on cryopreserved TILs, patients can receive highly metabolically active, healthy TILs, leading to more favorable outcomes. Such restimulation protocols, also referred to herein as additional "expansions" of the cell populations, are described in further detail herein.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue. The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab, and UCHT-1. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, Calif., USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

TABLE 1

Amino acid sequences of muromonab.

| Identifier | Sequence (One-Letter Amino Acid Symbols) | | | | | |
|---|---|---|---|---|---|---|
| SEQ ID NO: 1 | QVQLQQSGAE | LARPGASVKM | SCKASGYTFT | RYTMHWVKQR | PGQGLEWIGY | INPSRGYTNY | 60 |
| Muromonab | NQKFKDKATL | TTDKSSSTAY | MQLSSLTSED | SAVYYCARYY | DDHYCLDYWG | QGTTLTVSSA | 120 |
| heavy chain | KTTAPSVYPL | APVCGGTTGS | SVTLGCLVKG | YFPEPVTLTW | NSGSLSSGVH | TFPAVLQSDL | 180 |
| | YTLSSSVTVT | SSTWPSQSIT | CNVAHPASST | KVDKKIEPRP | KSCDKTHTCP | PCPAPELLGG | 240 |
| | PSVFLFPPKP | KDTLMISRTP | EVTCVVVDVS | HEDPEVKFNW | YVDGVEVHNA | KTKPREEQYN | 300 |
| | STYRVVSVLT | VLHQDWLNGK | EYKCKVSNKA | LPAPIEKTIS | KAKGQPREPQ | VYTLPPSRDE | 360 |
| | LTKNQVSLTC | LVKGFYPSDI | AVEWESNGQP | ENNYKTTPPV | LDSDGSFFLY | SKLTVDKSRW | 420 |
| | QQGNVFSCSV | MHEALHNHYT | QKSLSLSPGK | | | | 450 |
| SEQ ID NO: 2 | QIVLTQSPAI | MSASPGEKVT | MTCSASSSVS | YMNWYQQKSG | TSPKRWIYDT | SKLASGVPAH | 60 |
| Muromonab | FRGSGSGTSY | SLTISGMEAE | DAATYYCQQW | SSNPFTFGSG | TKLEINRADT | APTVSIFPPS | 120 |
| light chain | SEQLTSGGAS | VVCFLNNFYP | KDINVKWKID | GSERQNGVLN | SWTDQDSKDS | TYSMSSTLTL | 180 |
| | TKDEYERHNS | YTCEATHKTS | TSPIVKSFNR | NEC | | | 213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, J. Immunol. 2004, 172, 3983-88 and Malek, Annu. Rev. Immunol. 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, N.H., USA (CELLGRO GMP) or ProSpec-Tany TechnoGene Ltd., East Brunswick, N.J., USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, Calif., USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4902,502, the disclosures of which are incorporated by reference herein. Formulations of IL-2 suitable for use in the invention are described in U.S. Pat. No. 6,706,289, the disclosure of which is incorporated by reference herein.

TABLE 2

Amino acid sequences of interleukins.

| Identifier | Sequence (One-Letter Amino Acid Symbols) | |
|---|---|---|
| SEQ ID NO: 3<br>recombinant<br>human IL-2<br>(rhIL-2) | MAPTSSSTKK TQLQLEHLLL DLQMILNGIN NYKNPKLTRM LTFKFYMPKK ATELKHLQCL<br>EEELKPLEEV LNLAQSKNFH LRPRDLISNI NVIVLELKGS ETTFMCEYAD ETATIVEFLN<br>RWITFCQSII STLT | 60<br>120<br>134 |
| SEQ ID NO: 4<br>Aldesleukin | PTSSSTKKTQ LQLEHLLLDL QMILNGINNY KNPKLTRMLT FKFYMPKKAT ELKHLQCLEE<br>ELKPLEEVLN LAQSKNFHLR PRDLISNINV IVLELKGSET TFMCEYADET ATIVEFLNRW<br>ITFSQSIIST LT | 60<br>120<br>132 |
| SEQ ID NO: 5<br>recombinant<br>human IL-4<br>(rhIL-4) | MHKCDITLQE IIKTLNSLTE QKTLCTELTV TDIFAASKNT TEKETFCRAA TVLRQFYSHH<br>EKDTRCLGAT AQQFHRHKQL IRFLKRLDRN LWGLAGLNSC PVKEANQSTL ENFLERLKTI<br>MREKYSKCSS | 60<br>120<br>130 |
| SEQ ID NO: 6<br>recombinant<br>human IL-7<br>(rhIL-7) | MDCDIEGKDG KQYESVLMVS IDQLLDSMKE IGSNCLNNEF NFFKRHICDA NKEGMFLFRA<br>ARKLRQFLKM NSTGDFDLHL LKVSEGTTIL LNCTGQVKGR KPAALGEAQP TKSLEENKSL<br>KEQKKLNDLC FLKRLLQEIK TCWNKILMGT KEH | 60<br>120<br>153 |
| SEQ ID NO: 7<br>recombinant<br>human IL-15<br>(rhIL-15) | MNWVNVISDL KKIEDLIQSM HIDATLYTES DVHPSCKVTA MKCFLLELQV ISLESGDASI<br>HDTVENLIIL ANNSLSSNGN VTESGCKECE ELEEKNIKEF LQSFVHIVQM FINTS | 60<br>115 |
| SEQ ID NO: 8<br>recombinant<br>human IL-21<br>(rhIL-21) | MQDRHMIRMR QLIDIVDQLK NYVNDLVPEF LPAPEDVETN CEWSAFSCFQ KAQLKSANTG<br>NNERIINVSI KKLKRKPPST NAGRRQKHRL TCPSCDSYEK KPPKEFLERF KSLLQKMIHQ<br>HLSSRTHGSE DS | 60<br>120<br>132 |

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, Respir. Res. 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and IgG1 expression from B cells. Recombinant human IL-4 suitable for use in the invention is commercially available from multiple suppliers, including ProSpec-Tany TechnoGene Ltd., East Brunswick, N.J., USA (Cat. No. CYT-211) and ThermoFisher Scientific, Inc., Waltham, Mass., USA (human IL-15 recombinant protein, Cat. No. Gibco CTP0043). The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, Blood 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-4 suitable for use in the invention is commercially available from multiple suppliers, including ProSpec-Tany TechnoGene Ltd., East Brunswick, N.J., USA (Cat. No. CYT-254) and ThermoFisher Scientific, Inc., Waltham, Mass., USA (human IL-15 recombinant protein, Cat. No. Gibco PHC0071). The amino acid sequence of recombinant human IL-7 suitable for use in the invention is given in Table 2 (SEQ ID NO:6).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, Blood 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, N.J., USA (Cat. No. CYT-230-b) and ThermoFisher Scientific, Inc., Waltham, Mass., USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, Nat. Rev. Drug. Disc. 2014, 13, 379-95, the disclosure of which is incorporated by reference herein. IL-21 is primarily produced by natural killer T cells and activated human CD4+ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, N.J., USA (Cat. No. CYT-408-b) and ThermoFisher Scientific, Inc., Waltham, Mass., USA (human IL-21 recombinant protein, Cat. No. 14-8219-80). The amino acid sequence of recombinant human IL-21 suitable for use in the invention is given in Table 2 (SEQ ID NO:8).

When "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the genetically modified cytotoxic lymphocytes described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{11}$, $10^7$ to $10^{11}$, to $10^{10}$, to $10^{11}$, $10^6$ to $10^{10}$, $10^7$ $10^8$ $10^8$ to $10^{10}$, $10^9$ to $10^{11}$, or $10^9$ to $10^{10}$ cells/kg body weight), including all integer values within those ranges. Genetically modified cytotoxic lymphocytes compositions may also be administered multiple times at these dosages. The genetically modified cytotoxic lymphocytes can be administered by using infusion techniques that are commonly known in immunotherapy (see, e.g., Rosenberg et al., *New Eng. J. of Med.* 319: 1676, 1988). The optimal dosage and treatment regime for a particular patient can readily be determined by one skilled in the art of medicine by monitoring the patient for signs of disease and adjusting the treatment accordingly.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "solid tumor" refers to an abnormal mass of tissue that usually does not contain cysts or liquid areas. Solid tumors may be benign or malignant. The term "solid tumor cancer refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs).

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., Cancer Res., 2012, 72, 2473. Although tumors express antigens that should be recognized by T cells, tumor clearance by the immune system is rare because of immune suppression by the microenvironment.

In an embodiment, the invention includes a method of treating a cancer with a population of rTILs, wherein a patient is pre-treated with non-myeloablative chemotherapy prior to an infusion of rTILs according to the invention. In some embodiments, the population of rTILs may be provided with a population of eTils, wherein a patient is pre-treated with nonmyeloablative chemotherapy prior to an infusion of rTILs and eTils according to the invention. In an embodiment, the non-myeloablative chemotherapy is cyclophosphamide 60 mg/kg/d for 2 days (days 27 and 26 prior to rTIL infusion) and fludarabine 25 mg/m2/d for 5 days (days 27 to 23 prior to rTIL infusion). In an embodiment, after non-myeloablative chemotherapy and rTIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the rTILs of the invention.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least one potassium channel agonist in combination with a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms "sequence identity," "percent identity," and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, Calif.) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are outlined below.

III. Restimulation of Cryopreserved TILs

As discussed herein, the present invention relates to the restimulation of cryopreserved TILs to increase their metabolic activity and thus relative health prior to transplant into a patient, and methods of testing said metabolic health. As generally outlined herein, TILs are generally taken from a patient sample and manipulated to expand their number prior to transplant into a patient. In some embodiments, the TILs may be optionally genetically manipulated as discussed below, and then cryopreserved. Once thawed, they are then restimulated to increase their metabolism prior to infusion into a patient.

Figure 11:
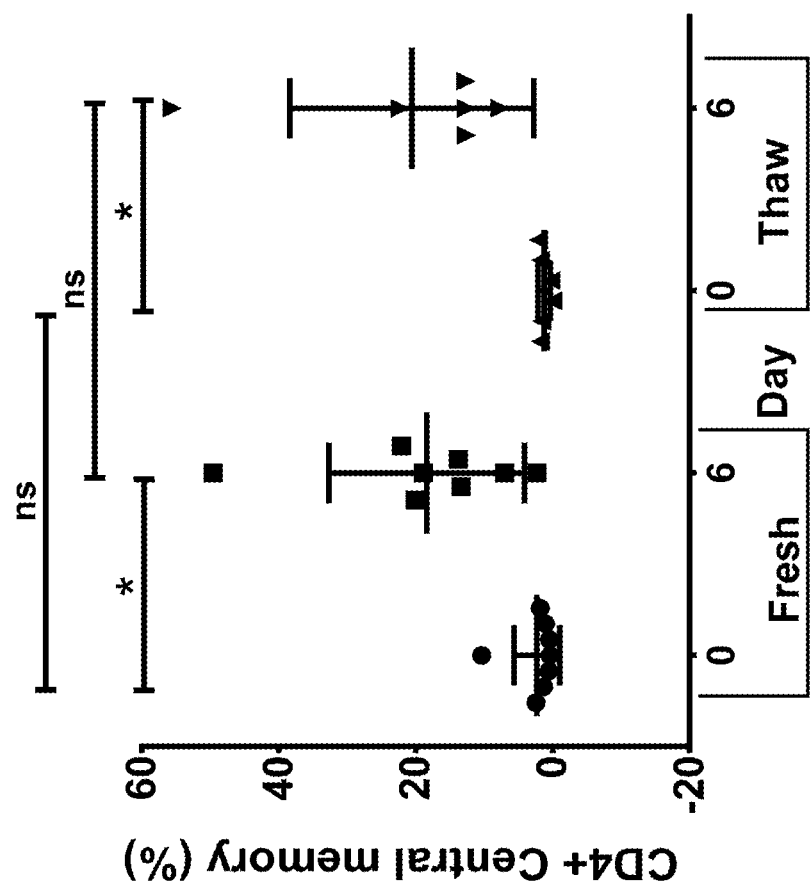
FIG. 11: Exemplary schematic of the TIL preparation process, sometimes referred to herein as the 1C process.

The "Step" Designations A, B, C, etc., below are in reference to FIG. 11. The ordering of the Steps below and in FIG. 11 is exemplary and any combination or order of steps, as well as additional steps, repetition of steps, and/or omission of steps is contemplated by the present application and the methods disclosed herein.

A. STEP A: Obtain Patient Tumor Sample

In general, TILs are initially obtained from a patient tumor sample ("primary TILs") and then expanded into a larger population for further manipulation as described herein, optionally cryopreserved, restimulated as outlined herein and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, useful TILs are obtained from malignant melanoma tumors, as these have been reported to have particularly high levels of TILs.

The term "solid tumor" refers to an abnormal mass of tissue that usually does not contain cysts or liquid areas. Solid tumors may be benign or malignant. The term "solid tumor cancer refers to malignant, neoplastic, or cancerous solid tumors. Solid tumor cancers include, but are not limited to, sarcomas, carcinomas, and lymphomas, such as cancers of the lung, breast, triple negative breast cancer, prostate, colon, rectum, and bladder. In some embodiments, the cancer is selected from cervical cancer, head and neck cancer, glioblastoma, ovarian cancer, sarcoma, pancreatic cancer, bladder cancer, breast cancer, triple negative breast cancer, and non-small cell lung carcinoma. The tissue structure of solid tumors includes interdependent tissue compartments including the parenchyma (cancer cells) and the supporting stromal cells in which the cancer cells are dispersed and which may provide a supporting microenvironment.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

Once obtained, the tumor sample is generally fragmented using sharp dissection into small pieces of between 1 to about 8 mm$^3$, with from about 2-3 mm$^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicin, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% CO$_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients.

In some embodiments, where the tumor is a solid tumor, the tumor undergoes physical fragmentation after the tumor sample is obtained, for example such as in Step A of FIG. 11. In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the tumor is fragmented and 2, 3, or 4 fragments or pieces are placed in each container for the first expansion. In some embodiments, the tumor is fragmented and 3 or 4 fragments or pieces are placed in each container for the first expansion. In some embodiments, the tumor is fragmented and 4 fragments or pieces are placed in each container for the first expansion, In some embodiments, the TILs are obtained from tumor fragments. In some embodiments, the tumor fragment is obtained sharp dissection. In some embodiments, the tumor fragment is between about 1 mm$^3$ and 10 mm$^3$. In some embodiments, the tumor fragment is between about 1 mm$^3$ and 8 mm$^3$. In some embodiments, the tumor fragment is about 1 mm$^3$. In some embodiments, the tumor fragment is about 2 mm$^3$. In some embodiments, the tumor fragment is about 3 mm$^3$. In some embodiments, the tumor fragment is about 4 mm$^3$. In some embodiments, the tumor fragment is about 5 mm$^3$. In some embodiments, the tumor fragment is about 6 mm$^3$. In some embodiments, the tumor fragment is about 7 mm$^3$. In some embodiments, the tumor fragment is about 8 mm$^3$. In some embodiments, the tumor fragment is about 9 mm$^3$. In some embodiments, the tumor fragment is about 10 mm$^3$.

In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, Calif.). After placing the tumor in enzyme media, the tumor can be mechanically dissociated for approximately 1 minute. The solution can then be incubated for 30 minutes at 37° C. in 5% CO$_2$ and it then mechanically disrupted again for approximately 1 minute. After being incubated again for 30 minutes at 37° C. in 5% CO$_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% CO$_2$. In some embodiments, at the end of the final incubation if the cell suspension contained a large number of red blood cells or dead cells, a density gradient separation using Ficoll can be performed to remove these cells.

In some embodiments, the harvested cell suspension prior to the first expansion step is called a "primary cell population" or a "freshly harvested" cell population.

In some embodiments, cells can be optionally frozen after sample harvest and stored frozen prior to entry into Step B, which is described in further detail below.

B. STEP B: First Expansion

In some embodiments, a first expansion of TILs (also referred to as a first expansion or first TIL expansion) may be performed using an initial bulk TIL expansion step (for example, Step B as indicated in FIG. 11 or a first expansion step; this can include an expansion step referred to as preREP) as described below and herein, followed by a second expansion step (for example, Step D as indicated in FIG. 11; which can include as an example what is referred to as a rapid expansion protocol (REP) step) as described below and herein, followed by optional cryopreservation (for example, after Step D as indicated in FIG. 11), and followed by an additional second expansion (for example, a second Step D, as indicated in FIG. 11, which can include what is sometimes referred to as a restimulation REP step) as described below and herein. The TILs obtained from this process may be optionally characterized for phenotypic characteristics and metabolic parameters as described herein. In some embodiments, the TILs are frozen (i.e., cryopreserved) after the first expansion (for example, Step B as indicated in FIG. 11) and stored until phenotyped for selection then thawed prior to proceeding to one or more second expansion steps (for example, one or more expansion according to Step D as indicated in FIG. 11).

In some embodiments, where the cells are frozen after obtained from the tumor sample (such as, for example, during in Step A as indicated in FIG. 11), the cells are thawed prior to the first expansion (for example, Step B as indicated in FIG. 11).

In embodiments where TIL cultures are initiated in 24-well plates, for example, using Costar 24-well cell culture cluster, flat bottom (Corning Incorporated, Corning, N.Y., each well can be seeded with 1×10$^6$ tumor digest cells or one tumor fragment in 2 mL of complete medium (CM) with IL-2 (6000 IU/mL; Chiron Corp., Emeryville, Calif.). In some embodiments, the tumor fragment is between about 1 mm$^3$ and 10 mm$^3$.

After preparation of the tumor fragments, the resulting cells (i.e., fragments) are cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of aAPC cell population) with 6000 IU/mL of IL-2. This primary cell population is cultured for a period of days, generally from 10 to 14 days, resulting in a bulk TIL population, generally about 1×10$^8$ bulk TIL cells. In some embodiments, the growth media during the first expansion comprises IL-2 or a variant thereof. In some embodiments, the IL is recombinant human IL-2 (rhIL-2). In some embodiments the IL-2 stock solution has a specific activity of 20-30×10$^6$ IU/mg for a 1 mg vial. In some embodiments the IL-2 stock solution has a specific activity of 20-×10$^6$ IU/mg for a 1 mg vial. In some embodiments the IL-2 stock solution has a specific activity of 25×10$^6$ IU/mg for a 1 mg vial. In some embodiments the IL-2 stock solution has a specific activity of 30×10$^6$ IU/mg for a 1 mg vial. In some embodiments, the IL-2 stock solution has a final concentration of 4-8×10$^6$ IU/mg of IL-2. In some embodiments, the IL-2 stock solution has a final concentration of 5-7×10$^6$ IU/mg of IL-2. In some embodiments, the IL-2 stock solution has a final concentration of 6×10$^6$ IU/mg of IL-2. In some embodiments, the IL-2 stock solution is prepare as described in Example 4. In some embodiments, first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, first expansion culture media comprises about 9,000 IU/mL of IL-2, to about 5,000 IU/mL of IL-2. In some embodiments, first expansion culture media comprises about 8,000 IU/mL of IL-2, to about 6,000 IU/mL of IL-2. In some embodiments, first expansion culture media comprises about 7,000 IU/mL of IL-2, to about 6,000 IU/mL of IL-2. In some embodiments, first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In some embodiments, the first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, Minn.) (FIG. 1), each flask was loaded with 10-40×10$^6$ viable tumor digest cells or 5-30 tumor fragments in 10-40 mL of CM with IL-2. Both the G-Rex10 and 24-well plates were incubated in a humidified incubator at 37° C. in 5% CO$_2$ and 5 days after culture initiation, half the media was removed and replaced with fresh CM and IL-2 and after day 5, half the media was changed every 2-3 days. In some embodiments, the CM is the CM1 described in the Examples, see, Example 5. In some embodiments, the first expansion occurs in an initial cell culture medium or a first cell culture medium. In some embodiments, the initial cell culture medium or the first cell culture medium comprises IL-2.

In some embodiments, the first TIL expansion can proceed for 11 days, 12 days, 13 days, 14 days, 15 days, 16 days, 17 days, 18 days, 19 days, 20 days, or 21 days. In some embodiments, the first TIL expansion can proceed for 11 days to 21 days. In some embodiments, the first TIL expansion can proceed for 12 days to 21 days. In some embodiments, the first TIL expansion can proceed for 13 days to 21 days. In some embodiments, the first TIL expansion can proceed for 14 days to 21 days. In some embodiments, the first TIL expansion can proceed for 15 days to 21 days. In some embodiments, the first TIL expansion can proceed for 16 days to 21 days. In some embodiments, the first TIL expansion can proceed for 17 days to 21 days. In some embodiments, the first TIL expansion can proceed for 18 days to 21 days. In some embodiments, the first TIL expansion can proceed for 19 days to 21 days. In some embodiments, the first TIL expansion can proceed for 20 days to 21 days. In some embodiments, the first TIL expansion can proceed for 21 days.

C. STEP C: First Expansion to Second Expansion Transition

In some embodiments, the TILs obtained from the first expansion (for example, from Step B as indicated in FIG. 11) are stored until phenotyped for selection. In some embodiments, the TILs obtained from the first expansion are cryopreserved after the first expansion and prior to the second expansion. In some embodiments, the TILs are cryopreserved as part of the first expansion to second expansion transition. For example, in some embodiments, the TILs are cryopreserved after Step B and before Step D as indicated in FIG. 11. In some embodiments, the TILs are cryopreserved and thawed as part of the first expansion to second expansion transition. For example, in some embodiments, the TILs are cryopreserved after Step B then thawed prior to proceeding to Step D (as provided in FIG. 11). In some embodiments, the transition from the first expansion to the second expansion occurs at about 22 days, 23, days, 24 days, 25 days, 26 days, 27 days, 28 days, 29 days, or 30 days from when fragmentation occurs. In some embodiments, the transition from the first expansion to the second expansion occurs at about 22 days to 30 days from when fragmentation occurs. In some embodiments, the transition from the first expansion to the second expansion occurs at about 24 days to 30 days from when fragmentation occurs. In some embodiments, the transition from the first expansion to the second expansion occurs at about 26 days to 30 days from when fragmentation occurs. In some embodiments, the transition from the first expansion to the second expansion occurs at about 28 days to 30 days from when fragmentation occurs. In some embodiments, the transition from the first expansion to the second expansion occurs at about 30 days from when fragmentation occurs.

D. STEP D: Second Expansion

In some embodiments, the second expansion or second TIL expansion (which can include expansions sometimes referred to as REP) of TIL can be performed using any TIL flasks or containers known by those of skill in the art. In some embodiments, the second TIL expansion can proceed for 14 days, 15 days, 16 days, 17 days, 18 days, 19 days, 20 days, 21 days, or 22 days. In some embodiments, the second TIL expansion can proceed for about 14 days to about 22 days. In some embodiments, the second TIL expansion can proceed for about 14 days to about 20 days. In some embodiments, the second TIL expansion can proceed for about 14 days to about 18 days. In some embodiments, the second TIL expansion can proceed for about 14 days to about 16 days. In some embodiments, the second TIL expansion can proceed for about 14 days.

In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells).

In some embodiments, the second expansion (which can include expansions referred to as REP) of TILs can be performed using T-175 flasks and gas-permeable bags as previously described (Tran K Q, Zhou J, Durflinger K H, et al., 2008, J Immunother, 31:742-751, and Dudley M E, Wunderlich J R, Shelton T E, et al. 2003, J Immunother, 26:332-342) or gas-permeable G-Rex flasks. In some embodiments, the second expansion is performed using flasks. In some embodiments, the second expansion is performed using gas-permeable G-Rex flasks. For TIL the second expansion in T-175 flasks, about $1\times10^6$ TIL are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% $CO_2$. In some embodiments, half the media is changed 5 days into the second expansion using 50/50 medium with 3000 IU/mL of IL-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about $2.0\times10^6$ cells/mL.

In some embodiments, the second expansion (which can include expansions referred to as REP) of TIL can be performed in 500 mL capacity gas permeable flasks with 100 cm² gas-permeable silicon bottoms (G-Rex 100, commercially available from Wilson Wolf Manufacturing Corporation, New Brighton, Minn., USA) (FIG. 1), about $5\times10^6$ or $10\times10^6$ TIL are cultured with irradiated allogeneic PBMC at a ratio of 1 to 100 in 400 mL of 50/50 medium, supplemented with 3000 IU/mL of IL-2 and 30 ng/mL of anti-CD3 (OKT3). The G-Rex100 flasks can be incubated at 37° C. in 5% $CO_2$. In some embodiments, 5 days into the second expansion, 250 mL of supernatant is removed and placed into centrifuge bottles and centrifuged at 1500 rpm (491×g) for 10 minutes. The TIL pellets can then be resuspended with 150 mL of fresh medium with 5% human AB serum, 3000 IU per mL of IL-2 and added back to the original G-Rex100 flasks. In embodiments where TILs are expanded serially in G-Rex100 flasks, on day 7 the TIL in each G-Rex100 are suspended in the 300 mL of media present in each flask and the cell suspension was divided into three 100 mL aliquots that can be used to seed three G-Rex100 flasks. Then 150 mL of AIM-V with 5% human AB serum and 3000 IU per mL of IL-2 can be added to each flask. The G-Rex100 flasks can be incubated at 37° C. in 5% $CO_2$ and after 4 days in to the second expansion, 150 mL of AIM-V with 3000 IU per mL of IL-2 can be added to each G-Rex100 flask. In some embodiments, the cells are harvested on day 14 of culture.

In some embodiments, the second expansion (which can include expansions referred to as REP) of TIL can be performed in a gas permeable container. For example, TILs can be rapidly expanded using non-specific T-cell receptor stimulation in the presence of interleukin-2 (IL-2) or interleukin-15 (IL-15). In an embodiment, expansion of the number of TILs uses about $1\times10^9$ to about $1\times10^{11}$ antigen-presenting feeder cells. The non-specific T-cell receptor stimulus can include, for example, about 30 ng/ml of OKT3, a mouse monoclonal anti-CD3 antibody (commercially available from Ortho-McNeil, Raritan, N.J. or Miltenyi Biotech, Auburn, Calif.). TILs can be rapidly expanded further stimulation of the TILs in vitro with one or more antigens, including antigenic portions thereof, such as epitope(s), of the cancer, which can be optionally expressed from a vector, such as a human leukocyte antigen A2 (HLA-A2) binding peptide, e.g., 0.3 µM MART-1:26-35 (27 L) or gp100:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2.

In some embodiments, the second expansion (which can include expansions referred to as REP) of TIL can be performed in 500 mL capacity gas permeable flasks with 100 cm gas-permeable silicon bottoms (G-Rex 100, commercially available from Wilson Wolf Manufacturing Corporation, New Brighton, Minn., USA), $5\times10^6$ or $10\times10^6$ TIL may be cultured with aAPCs at a ratio of 1 to 100 in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-Rex100 flask. The cells may be harvested on day 14 of culture.

In one embodiment, the second expansion (including expansions referred to as REP) is performed in flasks with the bulk TILs being mixed with a 100- or 200-fold excess of inactivated feeder cells, 30 mg/mL OKT3 anti-CD3 antibody and 3000 IU/mL IL-2 in 150 ml media. Media replacement is done (generally ⅔ media replacement via respiration with fresh media) until the cells are transferred to an alternative growth chamber. Alternative growth chambers include GRex flasks and gas permeable containers as more fully discussed below.

In another embodiment, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, Mass.). In some embodiments, viability is determined according to the Cellometer K2 Image Cytometer Automatic Cell Counter protocol described, for example, in Example 2.

In some embodiments, cells are grown for 7 days, 8 days, 9 days, 10 days, or 11 days of the total second expansion time before being split into more than one container or flask.

In some embodiments, the second expansion culture medium (e.g., sometimes referred to as CM2 or the second cell culture medium), comprises IL-2, OKT-3, as well as the antigen-presenting feeder cells (APCs), as discussed in more detail below.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the TIL expansion procedures described herein require an excess of feeder cells during the second expansion (including for example, expansions referred to as REP TIL expansions). In many embodiments, the feeder cells are peripheral blood mononuclear cells (PBMCs) obtained from standard whole blood units from healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the REP procedures.

In some embodiments, the growth media during the first expansion comprises IL-2 or a variant thereof. In some embodiments, the IL is recombinant human IL-2 (rhIL-2). In some embodiments the IL-2 stock solution has a specific activity of $20\text{-}30\times10^6$ IU/mg for a 1 mg vial. In some embodiments the IL-2 stock solution has a specific activity of $20\text{-}\times10^6$ IU/mg for a 1 mg vial. In some embodiments the IL-2 stock solution has a specific activity of $25\times10^6$ IU/mg for a 1 mg vial. In some embodiments the IL-2 stock solution has a specific activity of $30\times10^6$ IU/mg for a 1 mg vial. In some embodiments, the IL-2 stock solution has a final concentration of $4\text{-}8\times10^6$ IU/mg of IL-2. In some embodiments, the IL-2 stock solution has a final concentration of $5\text{-}7\times10^6$ IU/mg of IL-2. In some embodiments, the IL-2 stock solution has a final concentration of $6\times10^6$ IU/mg of IL-2. In some embodiments, the IL-2 stock solution is prepare as described in Example 4. In some embodiments, first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, first expansion culture media comprises about 9,000 IU/mL of IL-2, to about 5,000 IU/mL of IL-2. In some embodiments, first expansion culture media comprises about 8,000 IU/mL of IL-2, to about 6,000 IU/mL of IL-2. In some embodiments, first expansion culture media comprises about 7,000 IU/mL of IL-2, to about 6,000 IU/mL of IL-2. In some embodiments, first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In some embodiments, the second expansion cell culture media also includes an anti-CD3 antibody. In some embodiment, the cell culture medium comprises OKT3 antibody. In some embodiments, the cell culture medium comprises about 30 ng/mL of OKT3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT3 antibody.

In some embodiments, an anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety. As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-McNeil, Raritan, N.J. or Miltenyi Biotech, Auburn, Calif.).

In some embodiment, the cells in the second expansion are grown in a culture media with high doses of a cytokine, in particular IL-2, as is known in the art.

Alternatively, using combinations of cytokines for the second expansion of TILS is additionally possible, with combinations of two or more of IL-2, IL-15 and IL-21 as is generally outlined in International Publication No. WO 2015/189356 and International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

E. Optional Repeats of Step D: Second Expansion

In some embodiments, the second expansion is performed one or more times, i.e., the second expansion is repeated. For example, in some embodiments the Step D second expansion as indicated in FIG. 11 is repeated one or more times. In some embodiments, the second expansion is referred to as an additional second expansion. In some embodiments where the second expansion is performed more than once (i.e., where the second expansion is repeated), this can include procedures referred to as a TIL Rapid Expansion Protocol. In some embodiments, the TIL cell population is expanded in number after harvest and first expansion. This process is generally referred to in the art as a rapid expansion process (REP) and the repeated second expansion can include expansion referred to as reREP. This overall protocol can be generally accomplished using culture media comprising a number of components, including feeder cells, a cytokine source, and an anti-CD3 antibody, in a gas-permeable container. In some embodiments, one or more subsequent second expansion(s) are performed as described above. In some embodiments, one or more subsequent second expansions are performed as provided in under Step D in FIG. 11 and prior to Step E as provide in FIG. 11. In some embodiments, one, two, three, four or more second expansions are performed as described above. In some embodiments, one, two, three, four or more second expansions are performed as provided in Step D of FIG. 11 before Step E of FIG. 11. In some embodiments, two second expansions are performed as described above. In some embodiments, two second expansions are performed as provided in Step D of FIG. 11 before Step E of FIG. 11. In some embodiments, three second expansions are performed as described above. In some embodiments, three second expansions are performed as provided in Step D of FIG. 11 before Step E of FIG. 11. In some embodiments, four second expansions are performed as described above. In some embodiments, four second expansions are performed as provided in Step D of FIG. 11 before Step E of FIG. 11.

In some embodiments, the repeat of the second expansion of the TILS (such as for example in Step D of FIG. 11) can be referred to as a restimulation of TILs. In some embodiments, the present invention includes a restimulation step, i.e., a repeat of the second expansion (for example, a repeat of the second expansion from Step D of FIG. 11). In some embodiments, the repeated second expansion (which can include an expansion referred to as a restimulation step ("reREP")) is performed on cells that have been cryopreserved. In some embodiments, the TILs are cryopreserved after Step D. In some embodiments, after an initial second expansion in Step D, the cells may be cultured in regular media, e.g. a "resting" media, and then one or more second expansions steps are performed. In some embodiments, the resting media comprises IL-2. In some embodiments, the resting media does not comprise IL-2. In some embodiments, the resting media is a standard cell culture media known in the art. In some embodiments, the resting media is AIM-V, DMEM, DMEM/F12, MEM, RPMI, OptiMEM, IMDM, or any other standard media that is known in art, including commercially available media. In some embodiments, the resting media is AIM-V.

In general, as discussed herein, the TILs are initially prepared by obtaining a primary population of TILs from a tumor resected from a patient as discussed herein (the "primary cell population" or "first cell population"). This is followed with an initial bulk expansion utilizing a culturing of the cells with IL-2, forming a second population of cells (sometimes referred to herein as the "bulk TIL population" or "second population"). In some embodiments, this is also referred to as the initial or first expansion.

The bulk TIL population (for example, the population obtained from for example Step A in FIG. 11) is then subjected to a REP step, sometimes referred to as a first expansion (for example, the first expansion as described in Step B of FIG. 11) in a cell culture media comprising IL-2, OKT-3, and antigen presenting feeder cells (APCs), wherein the APCs generally comprise peripheral blood mononuclear cells (PBMCs; or, alternatively as discussed herein, using antigen presenting cells), wherein the rapid expansion (for example, the second expansion as provide in Step D of FIG. 11) is performed for at least 14 days. As discussed herein, the media may also contain combinations of IL-2, IL-15 and/or IL-23 rather than IL-2 alone. In some embodiments, this post second expansion (for example, post Step D of FIG. 11) expanded TIL population is at least 50-fold or 100-fold greater in number than the second population of TILs (for example, the population of TILs obtained from Step B of FIG. 11). In some embodiments, the population of TILs obtained after the second expansion in Step D of FIG. 11 are 50-fold or 100-fold greater in number than the TILs obtained from the first expansion in Step B of FIG. 11. TILs are measured by cell counting methods known in the art, including those methods described in the Examples provided herewith, including Examples 1, 2, and 3. In some embodiments, a K2 cell counter is employed to count the TILs. In some embodiments, a Cellometer IC2 Image cytometer is employed to count the TILs.

In some embodiments, as discussed herein, the TIL population obtained after the second expansion (sometimes referred to as a third TIL population or a REP cell population) is removed from the supplemented cell culture media (for example, the culture media used in Step D of FIG. 11 or the media referred to as CM2 in the Examples) and optionally cryopreserved in a storage media (for example, media containing 5% DMSO) prior to performing and additional second expansion step.

Optionally, the TILs can be cryopreserved after a second expansion and before an additional second expansion. In some embodiments, the TILs are cryopreserved after performing Step D of FIG. 11 and before performing an additional Step D of FIG. 11. In some embodiments, the cryopreserved TILs are thawed prior to performing the additional second expansion. In some embodiments, the cryopreserved TILs are thawed prior to performing the additional Step D as provided in FIG. 11. In some embodiments, the TILs are cryopreserved in 5% DMSO. In some embodiments, the TILs are cryopreserved in cell culture media plus 5% DMSO. Alternatively, the cells are removed from the supplemented cell culture media (for example, the culture media used in Step D of FIG. 11) and cultured in a resting media. Such media include those that are described in Examples 1 and 5, as well as the other Examples provided herewith. In some embodiments, resting media can include media with IL-2. In some embodiments, the resting media can be the media referred to as CM1 in the examples.

The additional second expansion (including expansions referred to as reREP) is done on either the thawed cells or resting cells, using a supplemented cell culture medium (for example, a medium as provide in Step D of FIG. 11) comprising IL-2, OKT-3, and feeder cells (for example, antigen presenting cells), generally comprising peripheral blood mononuclear cells (PBMCs; or, alternatively as discussed herein, using antigen presenting cells), wherein the additional second expansion is performed for at least 14 days. As discussed herein, the media may also contain combinations of IL-2, IL-15 and/or IL-23 rather than IL-2 alone.

This results in an expanded population of TILs that are characterized in that these expanded TILs exhibits an increased subpopulation of effector T cells and/or central memory T cells relative to the second population of TILs (e.g., the bulk starting TILs). In some embodiments, these expanded TILs are the TILs obtained from Step D of FIG. 11.

In some embodiments the memory T cells are those cells that constitutively CCR7 and CD62L. See, Sallusto, et al., *Annu. Rev. Immunol.*, 2004, 22:745-763; incorporated by reference herein in its entirety.

Thus, the present invention provides methods for the restimulation of cryopreserved TILs upon thawing, based on post-thaw methods that result in increases of metabolic health such as glycolysis and respiration. In some embodiments, method comprises providing a population of thawed cryopreserved TILs that are then treated to increase their metabolic health to allow for optimal treatment upon infusion into patients.

F. STEP E: Harvest TILS from Step D

After the second expansion step, cells can be harvested. In some embodiments the TILs are harvested after one, two, three, four or more second expansion steps. In some embodiments, the TILs are harvested after one, two, three, four or more second expansion steps according to Step D as provided in FIG. 11.

TILs can be harvested in any appropriate and sterile manner, including for example by centrifugation. Methods for TIL harvesting are well known in the art and any such know methods can be employed with the present process.

G. STEP F: Final Formulation and/or Transfer to Infusion Bag

After Steps A through E as provided in an exemplary order in FIG. 11 and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using APCs of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic.

1. Pharmaceutical Compositions, Dosages, and Dosing Regimens

In an embodiment, TILs expanded using APCs of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, a therapeutically sufficient number of TILs are needed for a suitable dosage. In some embodiments, from about $2.3 \times 10^{10}$ to about $13.7 \times 10^{10}$ TILs are administered, with an average of around $7.8 \times 10^{10}$ TILs, particularly if the cancer is melanoma. In an embodiment, about $1.2 \times 10^{10}$ to about $4.3 \times 10^{10}$ of TILs are administered. In some embodiments, about $3 \times 10^{10}$ to about $12 \times 10^{10}$ TILs are administered. In some embodiments, about $4 \times 10^{10}$ to about $10 \times 10^{10}$ TILs are administered. In some embodiments, about $5 \times 10^{10}$ to about $8 \times 10^{10}$ TILs are administered. In some embodiments, about $6 \times 10^{10}$ to about $8 \times 10^{10}$ TILs are administered. In some embodiments, about $7 \times 10^{10}$ to about $8 \times 10^{10}$ TILs are administered. In some embodiments, the therapeutically effective dosage is about $2.3 \times 10^{10}$ to about $13.7 \times 10^{10}$. In some embodiments, the therapeutically effective dosage is about $7.8 \times 10^{10}$ TILs, particularly of the cancer is melanoma. In some embodiments, the therapeutically effective dosage is about $1.2 \times 10^{10}$ to about $4.3 \times 10^{10}$ of TILs. In some embodiments, the therapeutically effective dosage is about $3 \times 10^{10}$ to about $12 \times 10^{10}$ TILs. In some embodiments, the therapeutically effective dosage is about $4 \times 10^{10}$ to about $10 \times 10^{10}$ TILs. In some embodiments, the therapeutically effective dosage is about $5 \times 10^{10}$ to about $8 \times 10^{10}$ TILs. In some embodiments, the therapeutically effective dosage is about $6 \times 10^{10}$ to about $8 \times 10^{10}$ TILs. In some embodiments, the therapeutically effective dosage is about $7 \times 10^{10}$ to about $8 \times 10^{10}$ TILs.

In some embodiments, the number of the TILs provided in the pharmaceutical compositions of the invention is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In an embodiment, the number of the TILs provided in the pharmaceutical compositions of the invention is in the range of $1\times10^6$ to $5\times10^6$, $5\times10^6$ to $1\times10^7$, $1\times10^7$, $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$. In some embodiments, the therapeutically effective dosage is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$ $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

H. Optional Cell Viability Analyses

Optionally, a cell viability assay can be performed after the Step B first expansion, using standard assays known in the art. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, Calif.) using a FACSCanto™ flow cytometer (BD Biosciences). The cells can be counted manually using a disposable c-chip hemocytometer (VWR, Batavia, Ill.) and viability can be assessed using any method known in the art, including but not limited to trypan blue staining.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

2. Cell Cultures

In an embodiment, a method for expanding TILs may include using about 5,000 mL to about 25,000 mL of cell medium, about 5,000 mL to about 10,000 mL of cell medium, or about 5,800 mL to about 8,700 mL of cell medium. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad Calif.). In this regard, the inventive methods advantageously reduce the amount of medium and the number of types of medium required to expand the number of TIL. In an embodiment, expanding the number of TIL may comprise adding fresh cell culture media to the cells (also referred to as feeding the cells) no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium therein using aAPCs for a duration of about 14 to about 42 days, e.g., about 28 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L. In an embodiment, TILs can be expanded in G-Rex flasks (commercially available from Wilson Wolf Manufacturing). Such embodiments allow for cell populations to expand from about $5 \times 10^5$ cells/cm$^2$ to between $10 \times 10^6$ and $30 \times 10^6$ cells/cm$^2$. In an embodiment this expansion is conducted without adding fresh cell culture media to the cells (also referred to as feeding the cells). In an embodiment, this is without feeding so long as medium resides at a height of about 10 cm in the GRex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy*, 2012, 35:283-292.

Optional Genetic Engineering of TILs

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19).

I. Optional Cryopreservation of TILs

As discussed above in Steps A through E, cryopreservation can occur at numerous points throughout the TIL expansion process. In some embodiments, the bulk TIL population after the first expansion according to Step B or the expanded population of TILs after the one or more second expansions according to Step D can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Examples 8 and 9.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

J. Phenotypic Characteristics of Expanded TILs

In some embodiment, the TILs are analyzed for expression of numerous phenotype markers after expansion, including those described herein and in the Examples. In an embodiment, expression of one or more phenotypic markers is examined. In some embodiments, the phenotypic characteristics of the TILs are analyzed after the first expansion in Step B. In some embodiments, the phenotypic characteristics of the TILs are analyzed during the transition in Step C. In some embodiments, the phenotypic characteristics of the TILs are analyzed during the transition according to Step C and after cryopreservation. In some embodiments, the phenotypic characteristics of the TILs are analyzed after the second expansion according to Step D. In some embodiments, the phenotypic characteristics of the TILs are analyzed after two or more expansions according to Step D. In some embodiments, the marker is selected from the group consisting of TCRab, CD57, CD28, CD4, CD27, CD56, CD8a, CD45RA, CD8a, CCR7, CD4, CD3, CD38, and HLA-DR. In some embodiments, the marker is selected from the group consisting of TCRab, CD57, CD28, CD4, CD27, CD56, and CD8a. In an embodiment, the marker is selected from the group consisting of CD45RA, CD8a, CCR7, CD4, CD3, CD38, and HLA-DR. In some embodiments, expression of one, two, three, four, five, six, seven, eight, nine, ten, eleven, twelve, thirteen, or fourteen markers is examined. In some embodiments, the expression from one or more markers from each group is examined. In some embodiments, one or more of HLA-DR, CD38, and CD69 expression is maintained (i.e., does not exhibit a statistically significant difference) in fresh TILs as compared to thawed TILs. In some embodiments, the activation status of TILs is maintained in the thawed TILs.

In an embodiment, expression of one or more regulatory markers is measured. In some embodiments, the regulatory marker is selected from the group consisting of CD137, CD8a, Lag3, CD4, CD3, PD1, TIM-3, CD69, CD8a, TIGIT, CD4, CD3, KLRG1, and CD154. In some embodiments, the regulatory marker is selected from the group consisting of CD137, CD8a, Lag3, CD4, CD3, PD1, and TIM-3. In some embodiments, the regulatory marker is selected from the group consisting of CD69, CD8a, TIGIT, CD4, CD3, KLRG1, and CD154. In some embodiments, regulatory molecule expression is decreased in thawed TILs as compared to fresh TILs. In some embodiments, expression of regulatory molecules LAG-3 and TIM-3 is decreased in thawed TILs as compared to fresh TILs. In some embodiments, there is no significant difference in CD4, CD8, NK, TCRαβ expression. In some embodiments, there is no significant difference in CD4, CD8, NK, TCRαβ expression, and/or memory markers in fresh TILs as compared to thawed TILs.

In some embodiments the memory marker is selected from the group consisting of CCR7 and CD62L In some embodiments, the viability of the fresh TILs as compared to the thawed TILs is at least 70%, at least 75%, at least 80%, at least 85%, at least 90%, at least 95%, or at least 98%. In some embodiments, the viability of both the fresh and thawed TILs is greater than 70%, greater than 75%, greater than 80%, greater than 85%, greater than 90%, greater than 95%, or greater than 98%. In some embodiments, the viability of both the fresh and thawed product is greater than 80%, greater than 81%, greater than 82%, greater than 83%, greater than 84%, greater than 85%, greater than 86%, greater than 87%, greater than 88%, greater than 89%, or greater than 90%. In some embodiments, the viability of both the fresh and thawed product is greater than 86%.

In an embodiment, restimulated TILs can also be evaluated for cytokine release, using cytokine release assays. In some embodiments, TILs can be evaluated for interferon-γ (IFN-γ) secretion in response to stimulation either with OKT3 or co-culture with autologous tumor digest. For example, in embodiments employing OKT3 stimulation, TILs are washed extensively, and duplicate wells are prepared with $1 \times 10^5$ cells in 0.2 mL CM in 96-well flat-bottom plates precoated with 0.1 or 1.0 µg/mL of OKT3 diluted in phosphate-buffered saline. After overnight incubation, the supernatants are harvested and IFN-γ in the supernatant is measured by ELISA (Pierce/Endogen, Woburn, Mass.). For the co-culture assay, $1 \times 10^5$ TIL cells are placed into a 96-well plate with autologous tumor cells. (1:1 ratio). After a 24-hour incubation, supernatants are harvested and IFN-γ release can be quantified, for example by ELISA.

Flow cytometric analysis of cell surface biomarkers: TIL samples were aliquoted for flow cytometric analysis of cell surface markers see, for Example see Examples 7, 8, and 9.

In some embodiments, the TILs are being evaluated for various regulatory markers. In some embodiments, the regulatory marker is selected from the group consisting of TCR α/β, CD56, CD27, CD28, CD57, CD45RA, CD45RO, CD25, CD127, CD95, IL-2R–, CCR7, CD62L, KLRG1, and CD122. In some embodiments, the regulatory marker is TCR α/β. In some embodiments, the regulatory marker is CD56. In some embodiments, the regulatory marker is CD27. In some embodiments, the regulatory marker is CD28. In some embodiments, the regulatory marker is CD57. In some embodiments, the regulatory marker is CD45RA. In some embodiments, the regulatory marker is CD45RO. In some embodiments, the regulatory marker is CD25. In some embodiments, the regulatory marker is CD127. In some embodiments, the regulatory marker is CD95. In some embodiments, the regulatory marker is IL-2R–. In some embodiments, the regulatory marker is CCR7. In some embodiments, the regulatory marker is CD62L. In some embodiments, the regulatory marker is KLRG1. In some embodiments, the regulatory marker is CD122.

K. Metabolic Health of Expanded TILs

The restimulated TILs are characterized by significant enhancement of basal glycolysis as compared to either freshly harvested TILs and/or post-thawed TILs.

Spare respiratory capacity (SRC) and glycolytic reserve can be evaluated for TILs expanded with aEM3 aAPCs in comparison to PBMC feeders. The Seahorse XF Cell Mito Stress Test measures mitochondrial function by directly measuring the oxygen consumption rate (OCR) of cells, using modulators of respiration that target components of the electron transport chain in the mitochondria. The test compounds (oligomycin, FCCP, and a mix of rotenone and antimycin A, described below) are serially injected to measure ATP production, maximal respiration, and non-mitochondrial respiration, respectively. Proton leak and spare respiratory capacity are then calculated using these parameters and basal respiration. Each modulator targets a specific component of the electron transport chain. Oligomycin inhibits ATP synthase (complex V) and the decrease in OCR following injection of oligomycin correlates to the mitochondrial respiration associated with cellular ATP production. Carbonyl cyanide-4 (trifluoromethoxy) phenylhydrazone (FCCP) is an uncoupling agent that collapses the proton gradient and disrupts the mitochondrial membrane potential. As a result, electron flow through the electron transport chain is uninhibited and oxygen is maximally consumed by complex IV. The FCCP-stimulated OCR can then be used to calculate spare respiratory capacity, defined as the difference between maximal respiration and basal respiration. Spare respiratory capacity (SRC) is a measure of the ability of the cell to respond to increased energy demand. The third injection is a mix of rotenone, a complex I inhibitor, and antimycin A, a complex III inhibitor. This combination shuts down mitochondrial respiration and enables the calculation of nonmitochondrial respiration driven by processes outside the mitochondria.

In some embodiments, the metabolic assay is basal respiration. In general, second expansion TILs or second additional expansion TILs (such as, for example, those described in Step D of FIG. 11, including TILs referred to as reREP TILs) have a basal respiration rate that is at least 50%, at least 55%, at least 60%, at least 65%, at least 70% at least 75%, at least 80% at least 85% at least 90% at least 95%, at least 97%, at least 98%, or at least 99% of the basal respiration rate of freshly harvested TILs. In some embodiments, the basal respiration rate is from about 50% to about 99% of the basal respiration rate of freshly harvested TILs. In some embodiments, the basal respiration rate is from about 60% to about 99% of the basal respiration rate of freshly harvested TILs. In some embodiments, the basal respiration rate is from about 70% to about 99% of the basal respiration rate of freshly harvested TILs. In some embodiments, the basal respiration rate is from about 80% to about 99% of the basal respiration rate of freshly harvested TILs. In some embodiments, the basal respiration rate is from about 90% to about 99% of the basal respiration rate of freshly harvested TILs. In some embodiments, the basal respiration rate is from about 95% to about 99% of the basal respiration rate of freshly harvested TILs. In some embodiments, the second expansion or second additional expansion TILs (such as, for example, those described in Step D of FIG. 11, including TILs referred to as reREP TILs) have a basal respiration rate that is not statistically significantly different than the basal respiration rate of freshly harvested TILs.

In general, second expansion TILs or additional second expansion TILs, such as those in Step D (including, for example, TILs referred to as reREP which have undergone an additional second expansion) TILs have a spare respiratory capacity that is at least is at least 50%, at least 55%, at least 60%, at least 65%, at least 70% at least 75%, at least 80% at least 85% at least 90% at least 95%, at least 97%, at least 98%, or at least 99% of the basal respiration rate of freshly harvested TILs. In some embodiments, the spare respiratory capacity is from about 50% to about 99% of the basal respiration rate of freshly harvested TILs. In some embodiments, the spare respiratory capacity is from about 50% to about 99% of the basal respiration rate of freshly harvested TILs. In some embodiments, the spare respiratory capacity is from about 60% to about 99% of the basal respiration rate of freshly harvested TILs. In some embodiments, the spare respiratory capacity is from about 70% to about 99% of the basal respiration rate of freshly harvested TILs. In some embodiments, the spare respiratory capacity is from about 80% to about 99% of the basal respiration rate of freshly harvested TILs. In some embodiments, the spare respiratory capacity is from about 90% to about 99% of the basal respiration rate of freshly harvested TILs. In some embodiments, the spare respiratory capacity is from about 95% to about 99% of the basal respiration rate of freshly harvested TILs. In some embodiments, the second expansion TILs or second additional expansion TILs (such as, for example, those described in Step D of FIG. 11, including TILs referred to as reREP TILs) have a spare respiratory capacity that is not statistically significantly different than the basal respiration rate of freshly harvested TILs.

In general, the second expansion TILs or second additional expansion TILs (such as, for example, those described in Step D of FIG. 11, including TILs referred to as reREP TILs) have a spare respiratory capacity that is at least is at least 50%, at least 55%, at least 60%, at least 65%, at least 70% at least 75%, at least 80% at least 85% at least 90% at least 95%, at least 97%, at least 98%, or at least 99% of the basal respiration rate of freshly harvested TILs. In some embodiments, the metabolic assay measured is glycolytic reserve. In some embodiments, the metabolic assay is glycolytic reserve. In some embodiments, the metabolic assay is spare respiratory capacity. To measure cellular (respiratory) metabolism cells were treated with inhibitors of mitochondrial respiration and glycolysis to determine a metabolic profile for the TIL consisting of the following measures: baseline oxidative phosphorylation (as measured by OCR), spare respiratory capacity, baseline glycolytic activity (as measured by ECAR), and glycolytic reserve. Metabolic profiles were performed using the Seahorse Combination Mitochondrial/Glycolysis Stress Test Assay (including the kit commercially available from Agilent®), which allows for determining a cells' capacity to perform glycolysis upon blockage of mitochondrial ATP production. In some embodiments, cells are starved of glucose, then glucose is injected, followed by a stress agent. In some embodiments, the stress agent is selected from the group consisting of oligomycin, FCCP, rotenone, antimycin A and/or 2-deoxyglucose (2-DG), as well as combinations thereof. In some embodiments, oligomycin is added at 10 mM. In some embodiments, FCCP is added at 10 mM. In some embodiments, rotenone is added at 2.5 mM. In some embodiments, antimycin A is added at 2.5 mM. In some embodiments, 2-deoxyglucose (2-DG) is added at 500 mM. In some embodiments, glycolytic capacity, glycolytic reserve, and/or non-glycolytic acidification are measured. In general, TILs have a glycolytic reserve that is at least 50%, at least 55%, at least 60%, at least 65%, at least 70% at least 75%, at least 80% at least 85% at least 90% at least 95%, at least 97%, at least 98%, or at least 99% of the basal respiration rate of freshly harvested TILs. In some embodiments, the glycolytic reserve is from about 50% to about 99% of the basal respiration rate of freshly harvested TILs. In some embodiments, the glycolytic reserve is from about 60% to about 99% of the basal respiration rate of freshly harvested TILs. In some embodiments, the glycolytic reserve is from about 70% to about 99% of the basal respiration rate of freshly harvested TILs. In some embodiments, the glycolytic reserve is from about 80% to about 99% of the basal respiration rate of freshly harvested TILs. In some embodiments, the glycolytic reserve is from about 90% to about 99% of the basal respiration rate of freshly harvested TILs. In some embodiments, the glycolytic reserve is from about 95% to about 99% of the basal respiration rate of freshly harvested TILs.

In some embodiments, the metabolic assay is basal glycolysis. In some embodiments second expansion TILs or additional second expansion TILs, such as those in Step D (including, for example, TILs referred to as reREP which have undergone an additional second expansion) have an increase in basal glycolysis of at least two-fold, at least three-fold, at least four-fold, at least five-fold, at least six-fold, at least 7-fold, at least eight-fold, at least nine-fold, or at least ten-fold. In some embodiments, the second expansion TILs or additional second expansion, such as those in Step D (including TILs referred to as reREP TILs) have an increase in basal glycolysis of about two-fold to about ten-fold. In some embodiments, the second expansion TILs or additional second expansion, such as those in Step D (including TILs referred to as reREP TILs) have an increase in basal glycolysis of about two-fold to about eight-fold. In some embodiments, the second expansion TILs or additional second expansion, such as those in Step D (including TILs referred to as reREP TILs) have an increase in basal glycolysis of about three-fold to about seven-fold. In some embodiments, the second expansion TILs or additional second expansion, such as those in Step D (including TILs referred to as reREP TILs) have an increase in basal glycolysis of about two-fold to about four-fold. In some embodiments, the second expansion TILs or additional second expansion, such as those in Step D (including TILs referred to as reREP TILs) have an increase in basal glycolysis of about two-fold to about three-fold.

In general, second expansion TILs or additional second expansion, such as those in Step D (including, for example, TILs referred to as reREP which have undergone an additional second expansion) TILs have a glycolytic reserve that is at least 50%, at least 55%, at least 60%, at least 65%, at least 70% at least 75%, at least 80% at least 85% at least 90% at least 95%, at least 97%, at least 98%, or at least 99% of the basal respiration rate of freshly harvested TILs. In some embodiments, the glycolytic reserve is from about 50% to about 99% of the basal respiration rate of freshly harvested TILs. In some embodiments, the glycolytic reserve is from about 60% to about 99% of the basal respiration rate of freshly harvested TILs. In some embodiments, the glycolytic reserve is from about 70% to about 99% of the basal respiration rate of freshly harvested TILs. In some embodiments, the glycolytic reserve is from about 80% to about 99% of the basal respiration rate of freshly harvested TILs. In some embodiments, the glycolytic reserve is from about 90% to about 99% of the basal respiration rate of freshly harvested TILs. In some embodiments, the glycolytic reserve is from about 95% to about 99% of the basal respiration rate of freshly harvested TILs. In some embodiments, the second expansion TILs or second additional expansion TILs (such as, for example, those described in Step D of FIG. 11, including TILs referred to as reREP TILs) have a spare respiratory capacity that is not statistically significantly different than the basal respiration rate of freshly harvested TILs.

Granzyme B Production: Granzyme B is another measure of the ability of TIL to kill target cells. Media supernatants restimulated as described above using antibodies to CD3, CD28, and CD137/4-1BB were also evaluated for their levels of Granzyme B using the Human Granzyme B DuoSet ELISA Kit (R & D Systems, Minneapolis, Minn.) according to the manufacturer's instructions. In some embodiments, the second expansion TILs or second additional expansion TILs (such as, for example, those described in Step D of FIG. 11, including TILs referred to as reREP TILs) have increased Granzyme B production. In some embodiments, the second expansion TILs or second additional expansion TILs (such as, for example, those described in Step D of FIG. 11, including TILs referred to as reREP TILs) have increased cytotoxic activity.

In some embodiments, the present methods include an assay for assessing TIL viability, using the methods as described above. In some embodiments, the TILs are expanded as discussed above, including for example as provided in FIG. 11. In some embodiments, the TILs are cryopreserved prior to being assessed for viability. In some embodiments, the viability assessment includes thawing the TILs prior to performing a first expansion, a second expansion, and an additional second expansion. In some embodiments, the present methods provide an assay for assessing cell proliferation, cell toxicity, cell death, and/or other terms related to viability of the TIL population. Viability can be measured by any of the TIL metabolic assays described above as well as any methods know for assessing cell viability that are known in the art. In some embodiments, the present methods provide as assay for assessment of cell proliferation, cell toxicity, cell death, and/or other terms related to viability of the TILs expanded using the methods described herein, including those exemplified in FIG. 11.

The present invention also provides assay methods for determining TIL viability. The present disclosure provides methods for assaying TILs for viability by expanding tumor infiltrating lymphocytes (TILs) into a larger population of TILs comprising:
- (i) obtaining a first population of TILs which has been previously expanded;
- (ii) performing a first expansion by culturing the first population of TILs in a cell culture medium comprising IL-2 to produce a second population of TILs; and
- (iii) performing a second expansion by supplementing the cell culture medium of the second population of TILs with additional IL-2, OKT-3, and antigen presenting cells (APCs), to produce a third population of TILs, wherein the third population of TILs is at least 50-fold or 100-fold greater in number than the second population of TILs, and wherein the second expansion is performed for at least 14 days in order to obtain the third population of TILs, wherein the third population of TILs comprises an increased subpopulation of effector T cells and/or central memory T cells relative to the second population of TILs, and wherein the third population is further assayed for viability.

In some embodiments, the method further comprises:
- (iv) performing an additional second expansion by supplementing the cell culture medium of the third population of TILs with additional IL-2, additional OKT-3, and additional APCs, wherein the additional second expansion is performed for at least 14 days to obtain a larger population of TILs than obtained in step (iii), wherein the larger population of TILs comprises an increased subpopulation of effector T cells and/or central memory T cells relative to the third population of TILs, and wherein the third population is further assayed for viability.

In some embodiments, prior to step (i), the cells are cryopreserved.

In some embodiments, the cells are thawed prior to performing step (i).

In some embodiments, step (iv) is repeated one to four times in order to obtain sufficient TILs for analysis.

In some embodiments, steps (i) through (iii) or (iv) are performed within a period of about 40 days to about 50 days.

In some embodiments, steps (i) through (iii) or (iv) are performed within a period of about 42 days to about 48 days.

In some embodiments, steps (i) through (iii) or (iv) are performed within a period of about 42 days to about 45 days.

In some embodiments, steps (i) through (iii) or (iv) are performed within about 44 days.

In some embodiments, the cells from steps (iii) or (iv) express CD4, CD8, and TCR αβ at levels similar to freshly harvested cells.

In some embodiments, the antigen presenting cells are peripheral blood mononuclear cells (PBMCs).

In some embodiments, the PBMCs are added to the cell culture on any of days 9 through 17 in step (iii).

In some embodiments, the effector T cells and/or central memory T cells in the larger population of TILs in step (iv) exhibit one or more characteristics selected from the group consisting of expression of CD27, expression of CD28, longer telomeres, increased CD57 expression, and decreased CD56 expression, relative to effector T cells, and/or central memory T cells in the third population of cells.

In some embodiments, the effector T cells and/or central memory T cells exhibit increased CD57 expression and decreased CD56 expression.

In some embodiments, the APCs are artificial APCs (aAPCs).

In some embodiments, the method further comprises the step of transducing the first population of TILs with an expression vector comprising a nucleic acid encoding a high-affinity T cell receptor.

In some embodiments, the step of transducing occurs before step (i).

In some embodiments, the method further comprises the step of transducing the first population of TILs with an expression vector comprising a nucleic acid encoding a chimeric antigen receptor (CAR) comprising a single chain variable fragment antibody fused with at least one endodomain of a T-cell signaling molecule.

In some embodiments, the step of transducing occurs before step (i).

In some embodiments, the TILs are assayed for viability.

In some embodiments, the TILs are assayed for viability after cryopreservation.

In some embodiments, the TILs are assayed for viability after cryopreservation and after step (iv).

According to the present disclosure, a method for assaying TILs for viability and/or further use in administration to a subject. In some embodiments, the method for assay tumor infiltratitng lymphocytes (TILs) comprises:
- (i) obtaining a first population of TILs;
- (ii) performing a first expansion by culturing the first population of TILs in a cell culture medium comprising IL-2 to produce a second population of TILs; and
- (iii) performing a second expansion by supplementing the cell culture medium of the second population of TILs with additional IL-2, OKT-3, and antigen presenting cells (APCs), to produce a third population of TILs, wherein the third population of TILs is at least 50-fold greater in number than the second population of TILs;
- (iv) harvesting, washing, and cryopreserving the third population of TILs;
- (v) storing the cryopreserved TILs at a cryogenic temperature;
- (vi) thawing the third population of TILs to provide a thawed third population of TILs; and
- (vii) performing an additional second expansion of a portion of the thawed third population of TILs by supplementing the cell culture medium of the third population with IL-2, OKT-3, and APCs for a reREP period of at least 3 days, wherein the third expansion is performed to obtain a fourth population of TILs, wherein the number of TILs in the fourth population of TILs is compared to the number of TILs in the third population of TILs to obtain a ratio;
- (viii) determining based on the ratio in step (vii) whether the thawed population of TILs is suitable for administration to a patient;
- (ix) administering a therapeutically effective dosage of the thawed third population of TILs to the patient when the ratio of the number of TILs in the fourth population of TILs to the number of TILs in the third population of TILs is determined to be greater than 5:1 in step (viii).

In some embodiments, the reREP period is performed until the ratio of the number of TILs in the fourth population of TILs to the number of TILs in the third population of TILs is greater than 50:1.

In some embodiments, the number of TILs sufficient for a therapeutically effective dosage is from about $2.3 \times 10^{10}$ to about $13.7 \times 10^{10}$.

In some embodiments, steps (i) through (vii) are performed within a period of about 40 days to about 50 days. In some embodiments, steps (i) through (vii) are performed within a period of about 42 days to about 48 days. In some embodiments, steps (i) through (vii) are performed within a period of about 42 days to about 45 days. In some embodiments, steps (i) through (vii) are performed within about 44 days.

In some embodiments, the cells from steps (iii) or (vii) express CD4, CD8, and TCR αβ at levels similar to freshly harvested cells. In some embodiments the cells are TILs.

In some embodiments, the antigen presenting cells are peripheral blood mononuclear cells (PBMCs). In some embodiments, the PBMCs are added to the cell culture on any of days 9 through 17 in step (iii).

In some embodiments, the effector T cells and/or central memory T cells in the larger population of TILs in steps (iii) or (vii) exhibit one or more characteristics selected from the group consisting of expression of CD27, expression of CD28, longer telomeres, increased CD57 expression, and decreased CD56 expression, relative to effector T cells, and/or central memory T cells in the third population of cells.

In some embodiments, the effector T cells and/or central memory T cells exhibit increased CD57 expression and decreased CD56 expression.

In some embodiments, the APCs are artificial APCs (aAPCs).

In some embodiments, the step of transducing the first population of TILs with an expression vector comprising a nucleic acid encoding a high-affinity T cell receptor.

In some embodiments, the step of transducing occurs before step (i).

In some embodiments, the step of transducing the first population of TILs with an expression vector comprising a nucleic acid encoding a chimeric antigen receptor (CAR) comprising a single chain variable fragment antibody fused with at least one endodomain of a T-cell signaling molecule.

In some embodiments, the step of transducing occurs before step (i).

In some embodiments, the TILs are assayed for viability after step (vii).

The present disclosure also provides further methods for assaying TILs. In some embodiments, the disclosure provides a method for assaying TILs comprising:
  (i) obtaining a portion of a first population of cryopreserved TILs;
  (ii) thawing the portion of the first population of cryopreserved TILs;
  (iii) performing a first expansion by culturing the portion of the first population of TILs in a cell culture medium comprising IL-2, OKT-3, and antigen presenting cells (APCs) for a reREP period of at least 3 days, to produce a second population of TILs, wherein the portion from the first population of TILs is compared to the second population of TILs to obtain a ratio of the number of TILs, wherein the ratio of the number of TILs in the second population of TILs to the number of TILs in the portion of the first population of TILs is greater than 5:1;
  (iv) determining based on the ratio in step (iii) whether the first population of TILs is suitable for use in therapeutic administration to a patient;
  (v) determining the first population of TILs is suitable for use in therapeutic administration when the ratio of the number of TILs in the second population of TILs to the number of TILs in the first population of TILs is determined to be greater than 5:1 in step (iv).

In some embodiments, the ratio of the number of TILs in the second population of TILs to the number of TILs in the portion of the first population of TILs is greater than 50:1.

In some embodiments, the method further comprises performing expansion of the entire first population of cryopreserved TILs from step (i) according to the methods as described in any of the embodiments provided herein.

In some embodiments, the method further comprises administering the entire first population of cryopreserved TILs from step (i) to the patient.

In some embodiments, the cryopreserved TILs are thawed and a second expansion performed to determine if the cells expand sufficiently. If the cells expand to a ratio of at least 5:1, the TILs are sufficiently viably for administration to the patient. If the cells expand to a ratio of at least 10:1, the TILs are sufficiently viably for administration to the patient. If the cells expand to a ratio of at least 15:1, the TILs are sufficiently viably for administration to the patient. If the cells expand to a ratio of at least 20:1, the TILs are sufficiently viably for administration to the patient. If the cells expand to a ratio of at least 25:1, the TILs are sufficiently viably for administration to the patient. If the cells expand to a ratio of at least 30:1, the TILs are sufficiently viably for administration to the patient. If the cells expand to a ratio of at least 35:1, the TILs are sufficiently viably for administration to the patient. If the cells expand to a ratio of at least 40:1, the TILs are sufficiently viably for administration to the patient. If the cells expand to a ratio of at least 45:1, the TILs are sufficiently viably for administration to the patient. If the cells expand to a ratio of at least 5:1, the TILs are sufficiently viably for administration to the patient.

The present disclosure also provides further methods for assaying TILs. In some embodiments, the disclosure provides a method for assaying TILs comprising:
  (i) obtaining a portion of a first population of cryopreserved TILs;
  (ii) thawing the portion of the first population of cryopreserved TILs;
  (iii) performing a first expansion by culturing the portion of the first population of TILs in a cell culture medium comprising IL-2, OKT-3, and antigen presenting cells (APCs) for a reREP period of at least 3 days, to produce a second population of TILs, wherein the portion from the first population of TILs is compared to the second population of TILs to obtain a ratio of the number of TILs, wherein the ratio of the number of TILs in the second population of TILs to the number of TILs in the portion of the first population of TILs is greater than 5:1;
  (iv) determining based on the ratio in step (iii) whether the first population of TILs is suitable for use in therapeutic administration to a patient; and
  (v) therapeutically administering the remainder of the first population of TILs to the patient when the ratio of the number of TILs in the second population of TILs to the number of TILs in the first population of TILs is determined to be greater than 5:1 in step (iv).

In some embodiments, the ratio of the number of TILs in the second population of TILs to the number of TILs in the portion of the first population of TILs is greater than 50:1.

In some embodiments, the method further comprises performing expansion of the entire first population of cryopreserved TILs from step (i) according to the methods of any of the preceding claims.

In some embodiments, the method further comprises administering the entire first population of cryopreserved TILs from step (i) to the patient.

In some embodiments, the method further comprised the step of assessing the metabolic health of the second population of TILs.

In some embodiments, the method further comprises the step of assessing the phenotype of the second population of TILs.

In some embodiments, the antigen presenting cells are allogeneic peripheral blood mononuclear cells.

L. Methods of Treating Patients

Methods of treatment begin with the initial TIL collection and culture of TILs. Such methods have been both described in the art by, for example, Jin et al. (*J. Immunotherapy*, 2012, 35(3):283-292), incorporated by reference herein in its entirety. As well as described throughout the Examples section below.

The present invention provides novel methods for TIL generation that have not been previously described, e.g., TILs produced according to Steps A through F. The expanded TILs produced according to Steps A through F above or as otherwise produced as described herein find particular use in the treatment of patients with cancer. General methods of using TILs for the treatment of cancer have been described in Goff, et al., *J. Clinical Oncology*, 2016, 34(20):2389-239, as well as the supplemental content; incorporated by reference herein in its entirety.) Similarly, the TILs produced according to the present invention can also be used for the treatment of cancer. In some embodiments, TIL were grown from resected deposits of metastatic melanoma as previously described (see, Dudley, et al., *J Immunother.*, 2003, 26:332-342; incorporated by reference herein in its entirety). Fresh tumor can be dissected under sterile conditions. A representative sample can be collected for formal pathologic analysis. Single fragments of 2 mm$^3$ to 3 mm$^3$. In some embodiments, 5, 10, 15, 20, 25 or 30 samples per patient are obtained. In some embodiments, 20, 25, or 30 samples per patient are obtained. In some embodiments, 20, 22, 24, 26, or 28 samples per patient are obtained. In some embodiments, 24 samples per patient are obtained. Samples can be placed in individual wells of a 24-well plate, maintained in growth media with high-dose IL-2 (6,000 IU/mL), and monitored for destruction of tumor and/or proliferation of TIL. Any tumor with viable cells remaining after processing can be enzymatically digested into a single cell suspension and cryopreserved, as described herein.

In some embodiments, expanded TILs can be sampled for phenotype analysis (CD3, CD4, CD8, and CD56) and tested against autologous tumor when available. TILs can be considered reactive if overnight co-culture yielded interferon-gamma (IFN-γ) levels >200 pg/mL and twice background. (Goff, et al., *J Immunother*, 2010, 33:840-847; incorporated by reference herein in its entirety). In some embodiments, cultures with evidence of autologous reactivity or sufficient growth patterns can be selected for a second expansion (for example, a second expansion as provided in according to Step D of FIG. 11), including second expansions that are sometimes referred to as rapid expansion (REP). In some embodiments, expanded TILs with high autologous reactivity (for example, high proliferation during a second expansion), are selected for an additional second expansion. In some embodiments, TILs with high autologous reactivity (for example, high proliferation during second expansion as provided in Step D of FIG. 11), are selected for an additional second expansion according to Step D of FIG. 11.

In some embodiments, the patient is not moved directly to ACT (adoptive cell transfer), for example, in some embodiments, after tumor harvesting and/or a first expansion, the cells are not utilized immediately. In such embodiments, TILs can be cryopreserved and thawed 2 days before the second expansion step (for example, in some embodiments, 2 days before a step referred to as a REP step). In such embodiments, TILs can be cryopreserved and thawed 2 days before the second expansion step (for example, in some embodiments, 2 days before a Step D as provided in FIG. 11). As described in various embodiments throughout the present application, the second expansion (including processes referred to as REP) used OKT3 (anti-CD3) antibody (Miltenyi Biotech, San Diego, Calif.) and IL-2 (3,000 IU/mL; Prometheus, San Diego, Calif.) in the presence of irradiated feeder cells, autologous when possible, at a 100:1 ratio (see, Dudley, et al., *J Immunother*, 2003, 26:332-342; incorporated by reference herein in its entirety). In some embodiments, the TILs can be cryopreserved and thawed 5 days before the second expansion step. In some embodiments, the TILs can be cryopreserved and thawed 4 days before the second expansion step. In some embodiments, the TILs can be cryopreserved and thawed 3 days before the second expansion step. In some embodiments, the TILs can be cryopreserved and thawed 2 days before the second expansion step. In some embodiments, the TILs can be cryopreserved and thawed 1 day before the second expansion step. In some embodiments, the TILs can be cryopreserved and thawed immediately before the second expansion step.

Cell phenotypes of cryopreserved samples of infusion bag TIL can be analyzed by flow cytometry (FlowJo) for surface markers CD3, CD4, CD8, CCR7, and CD45RA (BD BioSciences), as well as by any of the methods described herein. Serum cytokines were measured by using standard enzyme-linked immunosorbent assay techniques. A rise in serum IFN-g was defined as >100 pg/mL and greater than 4 3 baseline levels.

1. Optional Lymphodepletion Preconditioning of Patients

Experimental findings indicate that lymphodepletion prior to adoptive transfer of tumor-specific T lymphocytes plays a key role in enhancing treatment efficacy by eliminating regulatory T cells and competing elements of the immune system ('cytokine sinks'). Accordingly, some embodiments of the invention utilize a lymphodepletion step (sometimes also referred to as "immunosuppressive conditioning") on the patient prior to the introduction of the second expansion TILs or second additional expansion TILs (such as, for example, those described in Step D of FIG. 11, including TILs referred to as reREP TILs) of the invention.

In general, lymphodepletion is done using fludarabine and/or cyclophosphamide (the active form being referred to as mafosfamide) and combinations thereof. Such methods are described in Gassner et al. (*Cancer Immunol Immunother.* 2011, 60(1):75-85, Muranski, et al., *Nat Clin Pract Oncol.*, 2006 3(12):668-681, Dudley, et al., J Clin Oncol 2008, 26:5233-5239, and Dudley, et al., *J Clin Oncol.* 2005, 23(10):2346-2357, all of which are incorporated by reference herein in their entireties.

In some embodiments, the fludarabine is at a concentration of 0.5 μg/ml-10 μg/ml fludarabine (Sigma-Aldrich, MO, USA). In some embodiments, the fludarabine is at a concentration of 1 μg/ml fludarabine (Sigma-Aldrich, MO, USA). In some embodiments, the fludarabine treatment is for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day 25 mg/kg/day, 30 mg/kg/day, 35 mg/kg/day, 40 mg/kg/day, or 45 mg/kg/day. In some embodiments, the fludarabine treatment is for 2-7 days at 35 mg/kg/day. In some embodiments, the fludarabine treatment is for 4-5 days at 35 mg/kg/day. In some embodiments, the fludarabine treatment is for 4-5 days at 25 mg/kg/day.

In some embodiments, the mafosfamide, the active form of cyclophosphamide, is at a concentration of 0.5 µg/ml-10 µg/ml. In some embodiments, the mafosfamide, the active form of cyclophosphamide, is at a concentration of 1 µg/ml. In some embodiments, the cyclophosphamide treatment is for 1 day, 2 days, 3 days, 4 days, 5 days, 6 days, or 7 days or more. In some embodiments, the cyclophosphamide is administered at a dosage of 100 mg/m$^2$/day, 150 mg/m$^2$/day, 175 mg/m$^2$/day 200 mg/m$^2$/day, 225 mg/m$^2$/day, 250 mg/m$^2$/day, 275 mg/m$^2$/day, or 300 mg/m$^2$/day. In some embodiments, the cyclophosphamide is administered intravenously (i.e., i.v.) In some embodiments, the cyclophosphamide treatment is for 2-7 days at 35 mg/kg/day. In some embodiments, the cyclophosphamide treatment is for 4-5 days at 250 mg/m$^2$/day i.v. In some embodiments, the cyclophosphamide treatment is for 4 days at 250 mg/m$^2$/day i.v.

In some embodiments, the fludarabine and the cyclophosphamide are administered together to a patient. In some embodiments, fludarabine is administered at 25 mg/m$^2$/day i.v. and cyclophosphamide is administered at 250 mg/m$^2$/day i.v. over 4 days.

This protocol includes administration of fludarabine (25 mg/m$^2$/day i.v.) and cyclophosphamide (250 mg/m$^2$/day i.v.) over 4 days.

2. Exemplary Treatment Embodiments

In some embodiments, the present disclosure provides a method of treating a cancer with a population of tumor infiltrating lymphocytes (TILs) comprising the steps of (a) obtaining a first population of TILs from a tumor resected from a patient; (b) performing an initial expansion of the first population of TILs in a first cell culture medium to obtain a second population of TILs, wherein the second population of TILs is at least 5-fold greater in number than the first population of TILs, and wherein the first cell culture medium comprises IL-2; (c) performing a rapid expansion of the second population of TILs using a population of myeloid artificial antigen presenting cells (myeloid aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; (d) administering a therapeutically effective portion of the third population of TILs to a patient with the cancer. In some embodiments, the IL-2 is present at an initial concentration of about 3000 IU/mL and OKT-3 antibody is present at an initial concentration of about 30 ng/mL in the second cell culture medium. In some embodiments, first expansion is performed over a period not greater than 14 days. In some embodiments, the first expansion is performed using a gas permeable container. In some embodiments, the second expansion is performed using a gas permeable container. In some embodiments, the ratio of the second population of TILs to the population of aAPCs in the rapid expansion is between 1 to 80 and 1 to 400. In some embodiments, the ratio of the second population of TILs to the population of aAPCs in the rapid expansion is about 1 to 300. In some embodiments, the cancer for treatment is selected from the group consisting of melanoma, ovarian cancer, cervical cancer, non-small-cell lung cancer (NSCLC), lung cancer, bladder cancer, breast cancer, cancer caused by human papilloma virus, head and neck cancer, renal cancer, and renal cell carcinoma. In some embodiments, the cancer for treatment is selected from the group consisting of melanoma, ovarian cancer, and cervical cancer. In some embodiments, the cancer for treatment is melanoma. In some embodiments, the cancer for treatment is ovarian cancer. In some embodiments, the cancer for treatment is cervical cancer. In some embodiments, the method of treating cancer further comprises the step of treating the patient with a non-myeloablative lymphodepletion regimen prior to administering the third population of TILs to the patient. In some embodiments, the non-myeloablative lymphodepletion regimen comprises the steps of administration of cyclophosphamide at a dose of 60 mg/m2/day for two days followed by administration of fludarabine at a dose of 25 mg/m2/day for five days. In some embodiments, the high dose IL-2 regimen comprises 600,000 or 720,000 IU/kg of aldesleukin, or a biosimilar or variant thereof, administered as a 15-minute bolus intravenous infusion every eight hours until tolerance.

3. Methods of Co-Administration

In some embodiments, the TILs produced as described herein in Steps A through F can be administered in combination with one or more immune checkpoint regulators, such as the antibodies described below. For example, antibodies that target PD-1 and which can be co-administered with the TILs of the present invention include, e.g., but are not limited to nivolumab (BMS-936558, Bristol-Myers Squibb; Opdivo®), pembrolizumab (lambrolizumab, MK03475 or MK-3475, Merck; Keytruda®), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat #BP0146. Other suitable antibodies suitable for use in co-administration methods with TILs produced according to Steps A through F as described herein are anti-PD-1 antibodies disclosed in U.S. Pat. No. 8,008, 449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in co-administration methods with TILs produced according to Steps A through F as described herein. For example, antibodies that target PD-L1 and are in clinical trials, include BMS-936559 (Bristol-Myers Squibb) and MPDL3280A (Genentech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are suitable for use in co-administration methods with TILs produced according to Steps A through F as described herein. In some embodiments, the subject administered the combination of TILs produced according to Steps A through F is co-administered with a and anti-PD-1 antibody when the patient has a cancer type that is refractory to administration of the anti-PD-1 antibody alone. In some embodiments, the patient is administered TILs in combination with and anti-PD-1 when the patient has refractory melanoma. In some embodiments, the patient is administered TILs in combination with and anti-PD-1 when the patient has non-small cell lung carcinoma (NSCLC).

4. Adoptive Cell Transfer

Adoptive cell transfer (ACT) is a very effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). TILs for ACT can be prepared as described herein. In some embodiments, the TILs are prepared, for example, according to a method as described in FIG. 11. They can also be derived or from blood if they are genetically engineered to express antitumor T-cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. U.S. Publication No. 2011/0052530 relates to a method for performing adoptive cell therapy to promote cancer regression, primarily for treatment of patients suffering from metastatic melanoma, which is incorporated by reference in its entirety for these methods.

In some embodiments, TILs can be administered as described herein. In some embodiments, TILs can be administered in a single dose. Such administration may be by injection, e.g., intravenous injection. In some embodiments, TILs and/or cytotoxic lymphocytes may be administered in multiple doses. Dosing may be once, twice, three times, four times, five times, six times, or more than six times per year. Dosing may be once a month, once every two weeks, once a week, or once every other day. Administration of TILs and/or cytotoxic lymphocytes may continue as long as necessary.

I. Exemplary Embodiments

In an embodiment, the invention provides a method for expanding tumor infiltrating lymphocytes (TILs) comprising:
(a) obtaining a first population of TILs from a tumor resected from a patient;
(b) performing an initial expansion of the first population of TILs in a first cell culture medium to obtain a second population of TILs, wherein the first cell culture medium comprises IL-2;
(c) performing a rapid expansion of the second population of TILs, wherein the third population of TILs is at least 100-fold greater in number than the second population of TILs; and wherein the second cell culture medium comprises IL-2, OKT-3, and peripheral blood mononuclear cells (PBMCs), wherein the rapid expansion is performed for at least 14 days;
(d) removing the cells from the second cell culture medium and optionally cryopreserving the cells in a storage medium to obtain a third population of cells;
(e) optionally thawing the third population of cells; and
(f) performing a second rapid expansion of the third population of TILs in a third cell culture medium, wherein the third cell culture medium comprises IL-2, OKT-3, and peripheral blood mononuclear cells (PBMCs), wherein the second rapid expansion is performed for at least 14 days, to obtain a fourth population of TILs, wherein the fourth population of cells exhibits an increased subpopulation of effector T cells and/or central memory T cells relative to the second population of TILs; and
(g) optionally, repeating step f) one or more times.

In an embodiment, the invention provides that said restimulated cells express CD4, CD8 and TCR $\alpha\beta$ at levels similar to freshly harvested cells.

In an embodiment, the invention provides that said reREP medium comprises peripheral blood mononuclear cells (PBMCs).

In an embodiment, the invention provides that said PBMCs are added to the TILs on any of days 9 through 17. In some embodiments, the invention provides that said PBMCs are added to the TILs on days 9, 10, 11, 12, 13, 14, 15, 16, and/or 17.

In an embodiment, the invention provides that said reREP medium comprises aAPCs.

In an embodiment, the invention provides that the cryopreserved TILs were transduced with an expression vector comprising a nucleic acid encoding a high-affinity T cell receptor.

In an embodiment, the invention provides that the cryopreserved TILs were transduced with an expression vector comprising a nucleic acid encoding a chimeric antigen receptor (CAR) comprising an immunoglobulin light chain fused with an endodomain of a T-cell signaling molecule.

In an embodiment, the invention provides that restimulated TILs are infused into a patient.

In an embodiment, the invention provides that step d) further comprises removing the cells from the second cell culture medium.

In an embodiment, the invention provides that step f) is repeated a sufficient number of times in order to obtain sufficient TILs for a therapeutic dosage of said TILs.

In an embodiment, the invention provides a population of restimulated TILs made according to the methods described above and herein.

In an embodiment, the invention provides a population of restimulated TILs made according to the method of claim 1 wherein said restimulated TILs have at least a two-fold increase in basal glycolysis as compared to said thawed cryopreserved TILs.

In an embodiment, the invention provides a method for assessing the metabolic activity of a TIL cell population comprising measuring the basal glycolysis of said cells.

In an embodiment, the invention provides a method for assessing the metabolic activity of a TIL cell population comprising measuring the basal respiration of said cells.

In an embodiment, the invention provides a method for assessing the metabolic activity of a TIL cell population comprising measuring the spare respiratory capacity (SRC) of said cells.

In an embodiment, the invention provides a method for assessing the metabolic activity of a TIL cell population comprising measuring the glycolytic reserve of said cells.

In an embodiment, the invention provides a method of treating cancer in a patient with a population of tumor infiltrating lymphocytes (TILs) comprising the steps of:
a) obtaining a primary TIL population from said patient;
b) rapidly expanding said primary TIL population to form an expanded TIL population;
c) cryopreserving said expanded population to form a cryopreserved TIL population;
d) thawing said cryopreserved TIL population;

e) culturing said cryopreserved TIL population in media comprising IL-2 and anti-CD3 antibody to form a reREP TIL population; and
f) administering a therapeutically effective amount of reREP TIL cells to said patient.

In an embodiment, the invention provides a method for expanding tumor infiltrating lymphocytes (TILs) comprising:
(a) obtaining a first population of TILs from a tumor resected from a patient
(b) performing an initial expansion of the first population of TILs in a first cell culture medium to obtain a second population of TILs, wherein the first cell culture medium comprises IL-2;
(c) performing a rapid expansion of the second population of TILs, wherein the third population of TILs is at least 100-fold greater in number than the second population of TILs; and wherein the second cell culture medium comprises IL-2, OKT-3, and peripheral blood mononuclear cells (PBMCs), wherein the rapid expansion is performed for at least 14 days;
(d) removing the cells from the second cell culture medium and optionally cryopreserving the cells in a storage medium to obtain a third population of cells;
(e) optionally thawing the third population of cells;
(f) performing a second rapid expansion of the third population of TILs in a third cell culture medium, wherein the third cell culture medium comprises IL-2, OKT-3, and peripheral blood mononuclear cells (PBMCs), wherein the second rapid expansion is performed for at least 14 days, to obtain a fourth population of TILs, wherein the fourth population of cells exhibits an increased subpopulation of effector T cells and/or central memory T cells relative to the second population of TILs; and
(g) administering a therapeutically effective amount of reREP TIL cells to said patient.

In an embodiment, the invention provides that step d) further comprises removing the cells from the second cell culture medium.

In an embodiment, the invention provides that step f) is repeated a sufficient number of times in order to obtain sufficient TILs for a therapeutic dosage of said TILs.

EXAMPLES

Example 1: Restimulation Protocol

As discussed herein, a restimulation protocol and assay were developed utilizing fresh antigen restimulation following harvest or thaw of TILs grown in a REP.

The purpose of this example was to test the proliferation/expansion of post REP Tumor Infiltrating Lymphocytes in a Re-stimulation assay. Post REP TIL (post Step D TIL according to FIG. 11) were be restimulated with allogeneic PBMC feeder cells, anti-CD3 (clone OKT3) antibody, and interleukin-2 (IL-2). Viable cells were counted on Day 7 and recorded.

The post REP TIL (post Step D TIL according to FIG. 11) were infused into the patients who were previously lymphodepleted to facilitate TIL survival and expansion in vivo. Once the TIL were re-infused into the patient, they encountered antigen, resulting in the activation of the TIL, but the TIL were ultimately short-lived. Re-stimulation of the TIL through antigen contact together with exposure to IL-2 during ACT may result in TIL proliferation and tumor control or may lead to deletion through apoptosis (activation induced cell death) or induction of a non-proliferative (anergic) state due to lack of appropriate co-stimulation. Without being bound by theory, restimulation of post REP TIL (restimulation of, for example post Step D TIL according to FIG. 11) with allogeneic PBMC feeder cells may mimic the in vivo process by providing antigen stimulation and necessary cytokines for TIL expansion. Post REP TIL (post Step D TIL according to FIG. 11) were activated through membrane receptors on the feeder MNCs that bind to anti-CD3 (clone OKT3) antibody and crosslink to TIL in the REP flask, stimulating the TIL to expand.

Proliferation/Expansion of Post REP Tumor Infiltrating Lymphocytes in a Re-Stimulation Assay Post REP (post Step D TIL according to FIG. 11) TIL were restimulated with allogeneic PBMC feeder cells, anti-CD3 (clone OKT3) antibody, and interleukin-2 (IL-2). Viable cells were counted on Day 7 and recorded.

In some embodiments, this procedure can also be applied to test or validate the current REP protocol.

TABLE 3

DEFINITIONS AND ABBREVIATIONS

| Abbreviation | Definition |
|---|---|
| μl | Microliter |
| AOPI | Acridine Orange Propidium Iodide |
| BSC | Biological Safety Cabinet |
| BSL2 | Biosafety Level 2 |
| CM1 | Complete Medium for TIL, #1 |
| CM2 | Complete Medium for TIL, #2; 50:50 mixture of CM1 and AIM-V |
| GMP | Good Manufacturing Processing |
| Gy | Gray |
| IPA | Isopropyl alcohol |
| LN2 | Liquid nitrogen |
| MNC; | Mononuclear Cells; |
| PBMC | Peripheral Blood Mononuclear Cells |
| ml | Milliliter |
| NA | Not applicable |
| NR | Not required |
| OKT3 | MACS ® GMP CD3 pure (clone OKT3) antibody |
| PPE | Personal protective equipment |
| Pre-REP | Initial TIL cultures originating from tumor fragments |
| REP | Rapid Expansion Protocol |
| SDBB | San Diego Blood Bank |
| TIL | Tumor Infiltrating Lymphocyte |

TABLE 4

Materials

| Product | Specifications | Vendor | Catalog # | Storage |
|---|---|---|---|---|
| AIM-V | GMP | Gibco ™/ Life Technologies | 087-0112DK | 2-8° C. |
| Cellometer ViaStain ™ AOPI Staining Solution | NA | Nexcelom | CS2-0106 | 2-8° C. |
| Disposable Hemacytometer | NA | Nexcelom | CP2-001 | RT |
| CM1 | Prepared as per Example 5 | NA | NA | 2-8° C. |
| GMP recombinant human IL-2 (rhIL-2) | $6 \times 10^6$ IU/ml stock solution prepared as per Example 4 | CellGenix | 1020-1000 | −20° C. |

TABLE 4-continued

Materials

| Product | Specifications | Vendor | Catalog # | Storage |
|---|---|---|---|---|
| MACS ® GMP CD3 pure (clone OKT3) antibody | GMP | Miltenyi Biotec | 170-076-116 | 2-8° C. |
| 50 mL conical tubes | sterile | Any in use | | RT |
| transfer pipets | sterile | Any in use | | RT |
| 500 ml filter system | sterile | EMD/Millipore or equivalent | SCGPU05RE or equivalent | RT |
| 24-well tissue culture plates | sterile | Greiner or equivalent | 662160 or equivalent | RT |
| 5 ml, 10 ml serological pipets | sterile | Any in use | | RT |
| Pipet tips | sterile | Any in use | | RT |

TABLE 5

SPECIMENS

| Specimen | Specification | Origin | Ref number | Storage |
|---|---|---|---|---|
| Cryopreserved and Gamma-irradiated MNC Feeder lots | Stored in freezer | SDBB | NA | NA |
| Post-REP TIL cells | Fresh or Frozen in freezer | Iovance Biotechnologies | NA | NA |

The post REP (post Step D TIL according to FIG. 11) TIL were infused into the patients who were prior lymphodepleted to facilitate TIL survival and expansion in vivo. Once the TIL were re-infused into the patient, they encountered antigen, resulting in the activation of the TIL, but the TIL were ultimately short-lived. Re-stimulation of the TIL through antigen contact together with exposure to IL-2 during ACT may result in TIL proliferation and tumor control or may lead to deletion through apoptosis (activation induced cell death) or induction of a non-proliferative (anergic) state due to lack of appropriate co-stimulation. Our hypothesis was that restimulation of post REP TIL with allogeneic PBMC feeder cells mimicked the in vivo process by providing antigen stimulation and necessary cytokines for TIL expansion. Post REP TIL were activated through membrane receptors on the feeder MNCs that bind to anti-CD3 (clone OKT3) antibody and crosslink to TIL in the REP flask, stimulating the TIL to expand.

Procedure

Either fresh post-REP (post Step D TIL according to FIG. 11) or frozen post-REP (post Step D TIL according to FIG. 11) TIL that was thawed, was washed once in CM1 media. The Re-REP (repeat of Step D according to FIG. 11) was set up in a 24 well tissue culture plate with $2\times10^6$ MNC feeder cells, 30 ng/ml OKT3, $1\times10^4$ post-REP TIL plus 3,000 IU/ml rhIL-2 in CM2. The cultures were incubated for seven days in a 5% $CO_2$, 37° C. humidified incubator at which point viable cell recovery and viability was determined. The fold expansion of TIL was calculated based on the viable cell counts.

ReREP—Day 0

Prepare TIL

TILs were obtained from fresh post REP or frozen post REP. TIL cultures were removed from the incubator and transferred to the BSC. Next, 200 µl was removed for a cell count using the Cellometer K2. Counts were recorded.

Prepare Feeder Cells

For this protocol a minimum of $20\times10^6$ feeder cells were needed. Each 1 ml vial frozen by SDBB had $100\times10^6$ viable cells upon freezing. Assuming a 50% recovery upon thaw from LN2 storage, it was recommended to thaw at least two vials of feeder cells per lot giving an estimated $100\times10^6$ viable cells for each REP. Before thawing feeder cells, approximately 50 ml of CM2 was pre-warmed without rhIL-2 for each feeder lot that was tested. The designated feeder lot vials were removed from LN2 storage and placed on ice. Vials were transferred to the tissue culture room. Vials were thawed in a 37° C. water bath. Vials were transferred to BSC and sprayed or wiped with 70% EtOH or IPA. Using a transfer pipette, the contents of feeder vials was immediately transferred into 50 mL of warm CM2 in a 50-mL conical tube. 200 µl was removed for cell counting using the Cellometer K2. Counts were recorded. Cells were centrifuged at 350×g for 10 minutes. The supernatant and resuspended cells were aspirated in a desired volume at $2\times10^6$ cells/ml in warm CM2 plus 3000 IU/ml rhIL-2.

Prepare CM2+3000 IU/ml Working Solution

A sufficient amount of CM2 was prepared for the conditions needed. Each well contained 2 ml of CM2. Each well was supplemented the CM2 with 3000 IU/mL of rhIL-2. From the stock of $6\times10^6$ IU/mL, 50 µl was needed for each 100 ml of CM2.

Prepare MACS® GMP CD3 Pure (OKT3) Working Solution

Stock solution of OKT3 (1 mg/ml) was taken out of the 4° C. refrigerator. A final concentration of 30 ng/ml OKT3 was used in the REP. 60 ng of OKT3 were needed for 2 ml of CM2 medium in each 24 well. TIL+Feeders, TIL alone and Feeders alone conditions were cultured in triplicates. For each feeder lot tested, 1000 µl of a 1:1000 dilution of 1 mg/ml OKT3 for a working concentration of 1 µg/ml (1,000 ng/ml) was made. For 9 wells, 1000 µl of a 1:1000 dilution of 1 mg/ml OKT3. 1 µl 1 mg/ml OKT3+999 µl of CM2 with 3000 IU/ml IL-2 was made.

Prepare 24 Well Plate and Coculture.

Each ReREP tested required 9 wells of 24 well plate.

Each plate was labeled with Experiment Name, Feeder Lot #, post-REP TIL designation, date, and operator initials. Each plate was filled with components as listed in Table 8. Each component was added and each well filled with a total of 2 ml and place the plates into 37° C. incubator. Plates were mixed carefully 3 times using 1 ml pipette.

TABLE 6

REP set-up in 24 well plate

| Order of addition to single well of 24 well plate | TIL + Feeders + OKT3 | TIL + OKT3 | Feeders + OKT3 |
|---|---|---|---|
| TIL cells (1 × 10$^4$/0.5 ml) in CM2 + IL-2 | 500 ul | 500 ul | — |
| PBMC feeder cells (2 × 10$^6$/1 ml) in CM2 + IL-2 | 1000 ul | — | 1000 ul |
| OKT3 (1000 ng/ml) in CM2 + IL-2 | 60 ul | 60 ul | 60 ul |
| CM + IL-2 | 440 ul | 1440 ul | 940 ul |
| Total Volume | 2000 ul | 2000 ul | 2000 ul |

Media Exchange—Day 5

CM2 was prepared with 3000 IU/ml rhIL-2. 10 ml was needed. 1 ml of the media was removed from each well and discarded. With a 1 ml pipette, 1 ml warm CM2 with 3000 IU/mL rhIL-2 was transferred to each well. The plates were returned to the incubator.

Harvest—Day 7

Using a 1 ml serological pipet, each well was mixed to break up any clumps of cells. After thoroughly mixing cell suspension by pipetting, 200 μl was removed for cell counting using the Cellometer K2. All the conditions were counted and recorded for TIL+Feeders+OKT3, TIL+OKT3, and FEEDERS+OKT3.

In addition to 24 well ReREP, separate reREP were set up in 4 upright T25 tissue culture flasks with $1.3 \times 10^7$ MNC feeder cells, 30 ng/ml OKT3, $0.65 \times 10^5$ pre-REP TIL plus 3,000 IU/ml rhIL-2 in CM2. Note: Please refer to Evaluation of Irradiated Allogeneic Feeder Cells for Rapid Expansion Protocol of LN-144 (Example 6).

Allocation of cells for functional assays:

TABLE 7

Assay

| Functional Assay | Number of Cells/ Culture Supernatant |
| --- | --- |
| Flow Phenotyping | $10^6$ |
| Potency—P815effLuc-eGFP | $40^6$ |
| For restimulation assay to Granzyme-B, IFN-gamma | $5^6$ |
| Metabolism | $2^6$ |
| TCR Sequencing | $1^6$ |
| Store culture supernatant of TIL + feeders and feeders alone for Multiplex ELISA | 1 ml |

Evaluation/Acceptance Criteria

TABLE 8

Acceptance Criteria Used

| Test | Acceptance criteria |
| --- | --- |
| TIL expansion | At least a 50-200-fold expansion of Post REP TIL with feeders |
| PBMC Feeders cells alone | No expansion and at least 20% reduction in the total viable number of feeder cells |

Reference Procedures—Included in Examples Below

TABLE 9

Reference Procedures

| Name | Example Citation |
| --- | --- |
| Determination of Cell Count and Viability of TIL Cultures Using the Cellometer K2 Cell Counter | Example 2 |
| Preparation of IL-2 stock solution (CellGenix) | Example 4 |
| CM Media Formulation | Example 5 |
| Evaluation of Irradiated Allogeneic Feeder Cells for Rapid Expansion Protocol of LN-144 | Example 6 |
| Extended Phenotype of Tumor infiltrating Lymphocyte after Post REP | Example 6 |
| Validating the post REP cryofrozen TIL product | Example 8 and 9 |

Example 2: Determination of Cell Count and Viability of TIL Cultures Using the Cellometer K2 Cell Counter This example provides exemplary instructions for how the operation of the Cellometer K2 Image Cytometer automatic cell counter was carried out.

Scope: Determination of the total cell count and viability of cell cultures.

TABLE 10

Definitions

| | |
| --- | --- |
| μl | Microliter |
| AOPI | Acridine Orange Propidium Iodine |
| BSC | Biological Safety Cabinet |
| DPBS | Dulbecco's Phosphate Buffered Saline |
| ml | Milliliter |
| MNC | Mononuclear Blood Cells |
| NA | Not Applicable |
| PBMC | Peripheral Blood Mononuclear Cells |
| PPE | Personal Protective Equipment |
| Pre-REP | Initial TIL culture before Rapid Expansion Protocol of culture |
| REP | Rapid Expansion Protocol |
| TIL | Tumor Infiltrating Lymphocytes |

Procedure
Cell Suspension Preparation
Trypan Blue Preparation

The final Trypan blue concentration was 0.1%. The manufacturer recommended preparing a stock solution of 0.2%. When using Trypan blue on the Cellometer K2, the stock (0.4%) with PBS was diluted to 0.2%. The Trypan blue was filtered with a 0.2-0.4 micron filter and aliquoted in small volumes into labeled, capped tubes. The cell suspension was mixed at 1:1 with 0.2% trypan blue.

AOPI Preparation

When using AOPI on the Cellometer K2, the AOPI solution was obtained. Cell samples were stained at 1:1 with AOPI solution. NOTE: When counting high concentration cultures, the cell samples were diluted in cell culture medium prior to the final 1:1 dilution with Trypan Blue or AOPI. The manufacturer's suggested range of counting was used to determine the best dilution to use.

Cellometer K2 Set-Up

The Cellometer K2 equipment was turned on. The Cellometer Image Cytometer icon was selected on the associated computer monitor. On the main screen of the software, one of the Assays listed in the dropdown box was selected. When selecting the appropriate Assay, the Cell Type and Image Mode self-populated. Under "Sample" section, Set User/Sample ID was clicked to open another screen to input operator's information for specimen. "User ID" was entered. This consisted of the user's three letter initials. Enter "Sample ID". The sample ID was derived from incoming specimen information.

Set Up Dilution Parameters

When no other dilution was made besides the 1:1 mixture, the dilution factor was 2. When a dilution was made prior to the final 1:1 mixture, the dilution factor was 2 times of the prior dilution. The dilution factor was updated according to the mixture used.

Cell Counting

The plastic backing was removed from both sides of a Cellometer counting chamber slide (SD100) and placed on top of a clean, lint-free wipe. After preparing the cell suspension, a small aliquot of the sample was removed and transferred into a well of a multiwell cell culture plate or tube. When diluting the sample, the dilution was performed using cell culture medium. 20 µl of cell suspension was added into a well of the multiwell cell culture plate or tube. 20 µl of 0.2% trypan blue or the AOPI solution was added to the 20 µl of cell suspension and the sample mixed thoroughly. 20 µl of the 1:1 solution was measured and transferred it into one side of the counting chamber. NOTE: Touching the clear area of the slide was avoided. As needed, the samples were repeated on the other side of the slide. The chamber was inserted into the slot on the front of the Cellometer. For the AOPI cell counting, "Preview F1" was selected on the main screen to preview the green fluorescent image (live cell) image. For Trypan blue counting, "Preview Brightfield" was selected. The focusing wheel was used to bring image into optimal focus. Cells that had a bright center and a clearly-defined edge. "Count" was selected to begin the counting process. Results were displayed in a counting results pop-up box on the computer screen that showed the results of the counting process.

Example 3: Cellometer IC2 Image Cytometer Automatic Cell Counter

This Example describes the procedure for operation of the Cellometer K2 Image Cytometer automatic cell counter.
1. Definitions
   µl Microliter
   AOPI Acridine Orange Propidium Iodine
   BSC Biological Safety Cabinet
   DPBS Dulbecco's Phosphate Buffered Saline
   ml Milliliter
   MNC Mononuclear Blood Cells
   NA Not Applicable
   PBMC Peripheral Blood Mononuclear Cells
   PPE Personal Protective Equipment
   Pre-REP Initial TIL culture before Rapid Expansion Protocol of culture
   REP Rapid Expansion Protocol
   TIL Tumor Infiltrating Lymphocytes
7. Procedure
   7.1 Cell suspension preparation
   7.1.1 Trypan Blue Preparation
   The final Trypan blue concentration was 0.1%. The manufacturer recommended preparing a stock solution of 0.2%.
      7.1.1.1 When Trypan blue was used on the Cellometer K2, the stock (0.4%) was diluted with PBS to 0.2%.
      7.1.1.2 The Trypan blue was filtered with a 0.2-0.4 micron filter and aliquoted in small volumes into labeled, capped tubes.
      7.1.1.3 The cell suspension was mixed at 1:1 with 0.2% trypan blue.
   7.1.2 AOPI Preparation
      7.1.2.1 When AOPI was used on the Cellometer K2, the AOPI solution was obtained.
      7.1.2.2 The cell sample was stained at 1:1 with AOPI solution.
   NOTE: When high concentration cultures were counted, the cell samples were diluted in cell culture medium prior to the final 1:1 dilution with Trypan Blue or AOPI. The manufacturer's suggested range of counting was used to determine the best dilution to use.
   7.2 Cellometer K2 Set-Up
   7.2.1 The Cellometer K2 equipment was turned on.
   7.2.2 The Cellometer Image Cytometer icon was selected on the associated computer monitor.
   7.2.3 On the main screen of the software, one of the Assays listed in the dropdown box was selected.
      7.2.3.1 When the appropriate Assay was selected, the Cell Type and Image Mode self-populated.
      7.2.3.2 Under "Sample" section, Set User/Sample ID was selected to open another screen to input operator's information for specimen.
         7.2.3.2.1 The "User ID" was entered.
         7.2.3.2.2 The "Sample ID" was entered. The sample ID was derived from incoming specimen information.
      7.2.3.3 Dilution parameters were set up.
         7.2.3.3.1 When no other dilution was made besides the 1:1 mixture, the dilution factor was 2.
         7.2.3.3.2 When a dilution was made prior to the final 1:1 mixture, the dilution factor was 2 times of the prior dilution.
         7.2.3.3.3 The dilution factor was updated according to the mixture used in the dilution section of the screen. The pencil icon was selected to bring up the dialog screens.
         7.2.3.3.4 The F1 Image and F2 Image sections were verified to be identical to each other.
         7.2.3.3.5 The "Save" button was selected after set up was completed.
   7.3 Cell Counting
   7.3.1 The plastic backing from both sides of a Cellometer counting chamber slide (SD100) was removed and placed on top of a clean, lint-free wipe.
   7.3.2 After the cell suspension was prepared, a small aliquot of the sample was removed and transferred into a well of a multiwell cell culture plate or tube.
   7.3.3 When the sample was diluted, the dilution was performed using cell culture medium.
   7.3.4 20 µl of cell suspension was added into a well of the multiwell cell culture plate or tube.
   7.3.5 20 µl of 0.2% trypan blue or the AOPI solution was added to the 20 µl of cell suspension and mix sample thoroughly.
   7.3.6 20 µl of the 1:1 solution was measured and transferred it into one side of the counting chamber.
   NOTE: Touching the clear area of the slide was avoided.
   7.3.7 When necessary, the sample was repeated on the other side of the slide. 7.3.8. The chamber was inserted into the slot on the front of the Cellometer.
   7.3.8 For the AOPI cell counting, "Preview F1" was selected on the main screen to preview the green fluorescent image (live cell) image. For Trypan blue counting, "Preview Brightfield" was selected.
   7.3.9 The focusing wheel was used to bring image into optimal focus. Cells had a bright center and a clearly-defined edge.
   7.3.10 "Count" was selected to begin the counting process.
   7.3.11 Results were displayed in a counting results pop-up box on the computer screen that showed the results of the counting process.

Example 4: Preparation of IL-2 Stock Solution (Cellgenix)

This example describes an exemplary preparation procedure for an IL-2 stock solution.
Definitions/Abbreviations
µL: microliter or µl
BSC: Biological Safety Cabinet
BSL2: Biosafety Level 2

D-PBS: Dulbecco's Phosphate Buffered Saline
G: Gauge
GMP: Good Manufacturing Processing
HAc: Acetic Acid
HSA: Human Serum Albumin
mL: Milliliter
NA: Not applicable
PPE: Personal Protective Equipment
rhIL-2; IL-2: Recombinant human Interleukin-2
COA: Certificate of Analysis
6. Procedure
  6.1 Prepared 0.2% Acetic Acid solution (HAc).
    6.1.1 Transferred 29 mL sterile water to a 50 mL conical tube.
    6.1.2 Added 1 mL 1 N acetic acid to the 50 mL conical tube.
    6.1.3 Mixed well by inverting tube 2-3 times.
    6.1.4 Sterilized the HAc solution by filtration using a Steriflip filter.
    6.1.5 Capped, dated and labeled the solution "Sterile 0.2% Acetic Acid Solution"
    6.1.6 Solution expired after 2 months. Stored at room temperature.
  6.2 Prepared 1% HSA in PBS.
    6.2.1 Added 4 mL of 25% HSA stock solution to 96 mL PBS in a 150 mL sterile filter unit.
    6.2.2 Filtered solution.
    6.2.3 Capped, dated and labeled the solution "1% HSA in PBS."
    6.2.4 Solution expired after 2 months. Stored 4° C.
  6.3 For each vial of rhIL-2 prepared, document.
  6.4 Prepared rhIL-2 stock solution (6×10⁶ IU/mL final concentration)
    6.4.1 Each lot of rh1L-2 was different and required information found in the manufacturer's Certificate of Analysis (COA), such as:
      6.4.1.1 Mass of rhIL-2 per vial (mg)
      6.4.1.2 Specific activity of rhIL-2 (IU/mg)
      6.4.1.3 Recommended 0.2% HAc reconstitution volume (mL)
    6.4.2 Calculated the volume of 1% HSA required for rhIL-2 lot by using the equation below:

$$\left(\frac{\text{Vial Mass (mg)} \times \text{Biological Activity}\left(\frac{IU}{mg}\right)}{6\times10^6 \frac{IU}{mL}}\right) - HAc\ vol\ (mL) = 1\%\ HSA\ vol\ (mL)$$

6.4.2.1 For example, according to CellGenix's rhIL-2 lot 10200121 COA, the specific activity for the 1 mg vial was 25×10⁶ IU/mg. It recommends reconstituting the rhIL-2 in 2 mL 0.2% HAc.

$$\left(\frac{1\ mg \times 25 \times 10^6 \frac{IU}{mg}}{6\times10^6 \frac{IU}{mL}}\right) - 2\ mL = 2.167\ mL\ HSA$$

6.4.3 Wiped rubber stopper of IL-2 vial with alcohol wipe.
    6.4.4 Using a 16 G needle attached to a 3 mL syringe, the recommended volume of 0.2% HAc was injected into the vial. Care was taken to not dislodge the stopper as the needle was withdrawn.
    6.4.5 Inverted vial 3 times and swirled until all powder was dissolved.
    6.4.6 The stopper was carefully removed and set aside on an alcohol wipe.
    6.4.7 Added the calculated volume of 1% HSA to the vial.
    6.4.8 Capped the vial with the rubber stopper.
  6.5 Storage of rhIL-2 solution
    6.5.1 For short-term storage (<72 hrs), vials were stored at 4° C.
    6.5.2 For long-term storage (>72 hrs), the vial was aliquoted into smaller volumes and stored in cryovials at −20° C. until ready to use. Freeze/thaw cycles were avoided. Expired 6 months after date of preparation.
    6.5.3 Rh-IL-2 labels included vendor and catalog number, lot number, expiration date, operator initials, concentration and volume of aliquot.

Example 5: Preparation of Media for Pre-Rep and Rep Processes

This Example describes the procedure for the preparation of tissue culture media for use in protocols involving the culture of tumor infiltrating lymphocytes (TIL) derived from various tumor types including, but not limited to, metastatic melanoma, head and neck squamous cell carcinoma, ovarian carcinoma, triple-negative breast carcinoma, and lung adenocarcinoma. In many cases, this media was used for preparation of any of the TILs described in the present application and Examples.

Definition
μg microgram
μm micrometer
μM micromolar
AIM-V® serum-free tissue culture medium (Thermo Fisher Scientific)
BSC Biological Safety Cabinet
CM1 Complete Medium #1
CM2 Complete Medium #2
CM3 Complete Medium #3
CM4 Complete Medium #4
IU or U International units
ml milliliter
mM millimolar
NA not applicable
PPE personal protective equipment
Pre-REP pre-Rapid Expansion Process
REP Rapid Expansion Process
rhIL-2, IL-2 recombinant human Interleukin-2
RPMI1640 Roswell Park Memorial Institute medium, formulation 1640
SOP Standard Operating Procedure
TIL tumor infiltrating lymphocytes
7. Procedure
  7.1 All procedures were done using sterile technique in a BSC (Class II, Type A2).
    7.1.1 Surface of hood was sprayed with 70% ethanol prior to its use.
    7.1.2 All items and reagents were sprayed with 70% ethanol prior to placing them into tissue culture hood.
  7.2 Aliquoting of 200 mM L-glutamine
    7.2.1 L-glutamine was supplied in larger volumes than needed for the preparation of serum (e.g., 100 ml or 500 ml volumes).
    7.2.2 Thawed bottle of L-glutamine in 37° C. water bath.

7.2.3 Mixed L-glutamine well after thawing, as it precipitates after thaw. Ensure that all precipitates have returned to solution prior to aliquoting.
7.2.4 Placed 5-10 ml aliquots of L-glutamine into sterile 15 ml conical tubes.
7.2.5 Labeled tubes with concentration, vendor, lot number, date aliquoted, and expiration date.
7.2.6 Tubes were stored at −20° C. and pulled as needed for media preparation.
7.3 Preparation of CM1
  7.3.1 Removed the following reagents from cold storage and warmed them in a 37° C. water bathe:
    7.3.1.1 RPMI1640
    7.3.1.2 Human AB serum
    7.3.1.3 200 mM L-glutamine
  7.3.2 Removed the BME from 4° C. storage and place in tissue culture hood.
  7.3.3 Placed the gentamycin stock solution from room temperature storage into tissue culture hood.
  7.3.4 Prepared CM1 medium according to Table 1 below by adding each of the ingredients into the top section of a 0.2 µm filter unit appropriate to the volume that was filtered.

TABLE 11

Preparation of CM1

| Ingredient | Final concentration | Final Volume 500 ml | Final Volume 1L |
|---|---|---|---|
| RPMI1640 | NA | 450 ml | 900 ml |
| Human AB serum, heat-inactivated 10% | 50 ml | | 100 ml |
| 200 mM L-glutamine | 2 mM | 5 ml | 10 ml |
| 55 mM BME | 55 µM | 0.5 ml | 1 ml |
| 50 mg/ml gentamicin sulfate | 50 µg/ml | 0.5 ml | 1 ml |

7.3.5 Labeled the CM1 media bottle with its name, the initials of the preparer, the date it was filtered/prepared, the two week expiration date and stored at 4° C. until needed for tissue culture. Media was aliquoted into smaller volume bottles as required.
  7.3.6 Any remaining RPMI1640, Human AB serum, or L-glutamine was stored at 4° C. until next preparation of media.
  7.3.7 Stock bottle of BME was returned to 4° C. storage.
  7.3.8 Stock bottle of gentamicin was returned to its proper RT storage location.
  7.3.9 Because of the limited buffering capacity of the medium, CM1 was discarded no more than two weeks after preparation, or as the phenol red pH indicator showed an extreme shift in pH (bright red to pink coloration).
  7.3.10 On the day of use, the required amount of CM1 was warmed in a 37° C. water bath and 6000 IU/ml IL-2 was added.
  7.3.11 Additional supplementation—as was needed
    7.3.11.1 CM1 was supplemented with GlutaMAX®
      7.3.11.1.1 CM1 was prepared by substituting 2 mM GlutaMAX™ for 2 mM glutamine (final concentration, see Table 2.) When this was done, the media bottle was labeled adding "2 mM GlutaMAX" to prevent confusion with the standard formulation of CM1.
    7.3.11.2 CM1 was supplemented with extra antibiotic/antimycotic
      7.3.11.2.1 Some CM1 formulations required additional antibiotic or antimycotic to prevent contamination of pre-REP TIL grown from certain tumor types.
      7.3.11.2.2 Antibiotic/antimycotic was added to the final concentrations shown in Table 2 below.
      7.3.11.2.3 When done, the media bottle was labeled by adding the name/s of the additional antibiotic/antimycotic to prevent confusion with the standard formulation of CM1.

8.

TABLE 12

Additional supplementation of CM1, as was needed.

| Supplement | Stock concentration | Dilution | Final concentration |
|---|---|---|---|
| GlutaMAXTm | 200 mM | 1:100 | 2 mM |
| Penicillin/streptomycin | 10,000 U/ml penicillin 10,000 µg/ml streptomycin | 1:100 | 100 U/ml penicillin 100 ug/ml streptomycin |
| Amphotericin B | 250 µg/ml | 1:100 | 2.5 µg/ml |

8.1 Preparation of CM2
  8.1.1 Removed prepared CM1 from refrigerator or prepare fresh CM1 as per Example above.
  8.1.2 Removed AIM-V® from refrigerator.
  8.1.3 Prepared the amount of CM2 needed by mixing prepared CM1 with an equal volume of AIM-V® in a sterile media bottle.
  8.1.4 Added 3000 IU/ml IL-2 to CM2 medium on the day of usage.
  8.1.5 Made sufficient amount of CM2 with 3000 IU/ml IL-2 on the day of usage.
  8.1.6 Labeled the CM2 media bottle with its name, the initials of the preparer, the date it was filtered/prepared, the two week expiration date and stored at 4° C. until needed for tissue culture. Media was aliquoted into smaller volume bottles as required.
  8.1.7 Returned any CM2 without IL-2 to the refrigerator where it was stored for up to two weeks, or until phenol red pH indicator showed an extreme shift in pH (bright red to pink coloration).
8.2 Preparation of CM3
  8.2.1 Prepared CM3 on the day it was required for use.
  8.2.2 CM3 was the same as AIM-V® medium, supplemented with 3000 IU/ml IL-2 on the day of use.
  8.2.3 Prepared an amount of CM3 sufficient to experimental needs by adding IL-2 stock solution directly to the bottle or bag of AIM-V. Mixed well by gentle shaking. Labeled bottle with "3000 IU/ml IL-2" immediately after adding to the AIM-V. When there was excess CM3, it was stored in bottles at 4° C. labeled with the media name, the initials of the preparer, the date the media was prepared, and its expiration date (7 days after preparation).
  8.2.4 Discarded media supplemented with IL-2 after 7 days storage at 4° C.
8.3 Preparation of CM4
  8.3.1 CM4 was the same as CM3, with the additional supplement of 2 mM GlutaMAX™ (final concentration).
    8.3.1.1 For every 1 L of CM3, added 10 ml of 200 mM GlutaMAX™.
  8.3.2 Prepared an amount of CM4 sufficient to experimental needs by adding IL-2 stock solution and GlutaMAX™ stock solution directly to the bottle or bag of AIM-V. Mixed well by gentle shaking.

8.3.3 Labeled bottle with "3000 IL/nil IL-2 and GlutaMAX" immediately after adding to the AIM-V.

8.3.4 If there was excess CM4, it was stored in bottles at 4° C. labeled with the media name, "GlutaMAX", the initials of the preparer, the date the media was prepared, and its expiration date (7 days after preparation).

8.3.5 Discarded media supplemented with IL-2 after 7 days storage at 4° C.

Example 6: Evaluation of Irradiated Allogeneic Feeder Cells for Rapid Expansion Protocol of LN-144

This Example describes a novel abbreviated procedure for qualifying individual lots of gamma-irradiated peripheral mononuclear cells (PBMCs, also known as MNC) for use as allogeneic feeder cells in the exemplary methods described herein.

Each irradiated MNC feeder lot was prepared from an individual donor. Each lot or donor was screened individually for its ability to expand TIL in the REP in the presence of purified anti-CD3 (clone OKT3) antibody and interleukin-2 (IL-2). In addition, each lot of feeder cells was tested without the addition of TIL to verify that the received dose of gamma radiation was sufficient to render them replication incompetent.

Definitions
  AOPI—Acridine Orange/Propidum Iodide
  BSC—Biological Safety Cabinet
  CD3—Cluster of Differentiation 3; surface marker protein for T-lymphocytes
  CF—Centrifugal Force
  CM1—Complete Medium for T1L, #1
  CM2—Complete Medium for TIL, #
  CMO—Contract Manufacturing Organization
  $CO_2$— Carbon Dioxide
  EtOH—Ethyl Alcohol
  GMP—Good Manufacturing Practices
  Gy—Gray
  IL-2—Interleukin 2
  IU—International Units
  LN2—Liquid Nitrogen
  Mini-REP—Mini-Rapid Expansion Protocol
  ml—Milliliter
  MNC—Mononuclear Cells
  NA—Not Applicable
  OKT3—MACS GMP CD3 pure (clone OKT3) antibody
  PPE—Personal Protective Equipment
  Pre-REP—Before Rapid Expansion Protocol
  QS—Quantum Satis; fill to this quantity
  REP—Rapid Expansion Protocol
  TIL—Tumor Infiltrating Lymphocytes
  T25—25 cm2 tissue culture flask
  µg—Micrograms
  µl—Microliter
Equipment, Software, Materials
  Equipment
    BSC (Biological Safety Cabinet)
    Liquid Nitrogen Freezer
    Temperature-controlled water bath
    Centrifuge with swinging bucket rotor
    Humidified tissue culture incubator
    Pipet Aid
    2-20 µl Pipettors
    20-200 µl Pipettor
    100-1000 µl Pipettor
    Automated Cell Counter
  Material
    15 ml conical centrifuge tubes, sterile
    50 ml conical centrifuge tubes, sterile
    CM1
    CM2
    AIM V Medium CTS (Therapeutic Grade)
    Cell Counter Staining Solution
    IL-2
    MACS GMP CD3 pure (clone OKT3) antibody
    Sterile, disposable serological pipets
    Sterile, disposable transfer pipets
    Sterile, pipet tips
    24-well tissue culture plate
    T25 flasks (Greiner #690175)
    5.3.14. Zipper storage bags
Procedure
Background Gamma-irradiated, growth-arrested MNC feeder cells were required for REP (Step D) of TIL expansion. Membrane receptors on the feeder MNCs bind to anti-CD3 (clone OKT3) antibody and crosslink to TIL in the REP (Step D) flask, stimulating the TIL to expand. Feeder lots were prepared from the leukapheresis of whole blood taken from individual donors. The leukapheresis product was subjected to centrifugation over Ficoll-Hypaque, washed, irradiated, and cryopreserved under GMP conditions.

It was important that patients who received TIL therapy not be infused with viable feeder cells as this can result in Graft-Versus-Host Disease (GVHD). Feeder cells were therefore growth-arrested by dosing the cells with gamma-irradiation, which resulted in double strand DNA breaks and the loss of cell viability of the MNC cells upon reculture.

Evaluation Criteria and Experimental Set-Up

Feeder lots were evaluated on two criteria: 1) their ability to expand TIL in co-culture >100-fold and 2) their replication incompetency.

Feeder lots were tested in mini-REP format utilizing two primary pre-REP TIL lines grown in upright T25 tissue culture flasks. Feeder lots were tested against two distinct TIL lines, as each TIL line was unique in its ability to proliferate in response to activation in a REP. As a control, a lot of irradiated MNC feeder cells which was historically been shown to meet the criteria of 1) and 2): (1) their ability to expand TIL in co-culture >100-fold and (2) their replication incompetency was run alongside the test lots.

To ensure that all lots tested in a single experiment receive equivalent testing, sufficient stocks of the same pre-REP TIL lines were used to test all conditions and all feeder lots. For each lot of feeder cells tested, there was a total of six T25 flasks:
  Pre-REP TIL line #1 (2 flasks)
  Pre-REP TIL line #2 (2 flasks)
  Feeder control (2 flasks)
    NOTE: Flasks containing TIL lines #1 and #2 evaluated the ability of the feeder lot to expand TIL. The feeder control flasks evaluated the replication incompetence of the feeder lot.
Experimental Protocol
  Day −2/3, Thaw of TIL lines
    Prepared CM2 medium as per Example 5, Pre-REP and REP Media Preparation. Warmed CM2 in 37° C. water bath. Prepared 40 ml of CM2 supplemented with 3000 IU/ml IL-2. Kept warm until use. Placed 20 ml of pre-warmed CM2 without IL-2 into each of two 50 ml conical tubes labeled with names of the TIL lines used. Removed the two designated pre-REP TIL lines from LN2 storage and transfer the vials to the tissue culture room. Recorded TIL line identification form. Thawed vials by placing them inside a sealed zipper storage bag in a 37° C. water bath until a small amount of ice remains. Sprayed or wiped thawed vials with 70% ethanol and transferred vials to BSC. Used a sterile transfer pipet to immediately transfer the contents of vial into the 20 ml of CM2 in the prepared, labeled 50 ml conical tube. QS (filled to this quantity) to 40 ml using CM2 without IL-2 to wash cells. Centrifuged at 400×CF for 5 minutes. Aspirated the supernatant and resuspended in 5 ml warm CM2 supplemented with 3000 IU/ml IL-2. Removed small aliquot (20 µl) in duplicate for cell counting using an automated cell counter. Recorded the counts. While counting, placed the 50 ml conical tube with TIL cells into a humidified 37° C., 5% $CO_2$ incubator, with the cap loosened to allow for gas exchange. Determined cell concentration and dilute TIL to $1×10^6$ cells/ml in CM2 supplemented with IL-2 at 3000 IU/ml. Cultured in 2 ml/well of a 24-well tissue culture plate in as many wells as needed in a humidified 37° C. incubator until Day 0 of the mini-REP. Cultured the different TIL lines in separate 24-well tissue culture plates to avoid confusion and potential cross-contamination.

Day 0, Initiate Mini-REP

Prepared enough CM2 medium for the number of feeder lots to be tested. (e.g., for testing 4 feeder lots at one time, prepare 800 ml of CM2 medium). Aliquoted a portion of the CM2 prepared in Example 5 and supplemented it with 3000 IU/ml IL-2 for the culturing of the cells. (e.g., for testing 4 feeder lots at one time, prepare 500 ml of CM2 medium with 3000 IU/ml IL-2). The remainder of the CM2 with no IL-2 was used for washing of cells as described below.

Prepared TIL 7.3.2.4. Working with each TIL line separately to prevent cross-contamination, the 24-well plate with TIL culture was removed from the incubator and transferred to the BSC.

7.3.2.5. Using a sterile transfer pipet or 100-1000 µl Pipettor and tip, removed about 1 ml of medium from each well of TIL to be used and placed in an unused well of the 24-well tissue culture plate. This was used for washing wells.

7.3.2.6. Using a fresh sterile transfer pipet or 100-1000 µl Pipettor and tip, mixed remaining medium with TIL in wells to resuspend the cells and then transferred the cell suspension to a 50 ml conical tube labeled with the TIL name and recorded the volume.

7.3.2.7. Washed the wells with the reserved media and transferred that volume to the same 50 ml conical tube.

7.3.2.8. Spun the cells at 400×CF to collect the cell pellet.

7.3.2.9. Aspirated off the media supernatant and resuspended the cell pellet in 2-5 ml of CM2 medium containing 3000 IU/ml IL-2; volume used was based on the number of wells harvested and the size of the pellet—volume was sufficient to ensure a concentration of >$1.3×10^6$ cells/ml.

7.3.2.10. Using a serological pipet, mixed the cell suspension thoroughly and recorded the volume.

7.3.2.11. Removed 200 µl for a cell count using an automated cell counter.

7.3.2.12. While counting, the 50 ml conical tube with TIL cells was placed into a humidified, 5% $CO_2$, 37° C. incubator, with the cap loosened to allow gas exchange.

7.3.2.13. Recorded the counts.

7.3.2.14. Removed the 50 ml conical tube containing the TIL cells from the incubator and resuspended them cells at a concentration of $1.3×10^6$ cells/ml in warm CM2 supplemented with 3000 IU/ml IL-2. Returned the 50 ml conical tube to the incubator with a loosened cap.

7.3.2.15 When needed, the original 24-well plate was kept to reculture any residual TIL.

7.3.2.16. Repeated steps 7.3.2.4-7.3.2.15 for the second TIL line.

7.3.2.17. Just prior to plating the TIL into the T25 flasks for the experiment, TIL were diluted 1:10 for a final concentration of $1.3×10^5$ cells/ml as per step 7.3.2.35 below.

Prepare MACS GMP CD3 pure (OKT3) working solution 7.3.2.18. Took out stock solution of OKT3 (1 mg/ml) from 4° C. refrigerator and placed in BSC.

7.3.2.19. A final concentration of 30 ng/ml OKT3 was used in the media of the mini-REP.

7.3.2.20. 600 ng of OKT3 were needed for 20 ml in each T25 flask of the experiment; this is the equivalent of 60 µl of a 10 µg/ml solution for each 20 ml, or 360 µl for all 6 flasks tested for each feeder lot.

7.3.2.21. For each feeder lot tested, 400 µl of a 1:100 dilution of 1 mg/ml OKT3 was made for a working concentration of 10 µg/ml (e.g., for testing 4 feeder lots at one time, made 1600 µl of a 1:100 dilution of 1 mg/ml OKT3: 16µl of 1 mg/ml OKT3+1.584 ml of CM2 medium with 3000 IU/ml IL-2)

Prepare T25 flasks 7.3.2.22. Labeled each flask with the name of the TIL line tested, flask replicate number, feeder lot number, date, and initials of analyst.

7.3.2.23. Filled flask with the CM2 medium prior to preparing the feeder cells.

7.3.2.24. Placed flasks into 37° C. humidified 5% CO2 incubator to keep media warm while waiting to add the remaining components.

7.3.2.25. Once feeder cells were prepared, the components were added to the CM2 in each flask as shown in Table 14, Flask Set-up, below.

TABLE 13

Flask Set-up

| Component | Volume in co-culture | Volume in control (feeder only) flasks |
|---|---|---|
| CM2 + 3000 IU/ml IL-2 | 18 ml | 19 ml |
| MNC: $1.3 × 10^7$/ml in CM2 + 3000 IU IL-2 (final concentration $1.3 × 10^7$/flask) | 1 ml | 1 ml |
| OKT3: 10 µg/ml in CM2 + 3000 IU IL-2 | 60 nl | 60 nl |
| TIL: $1.3 × 10^5$/ml in CM2 with 3000 IU of IL-2 (final concentration $1.3 × 10^5$/flask) | 1 ml | 0 |

Prepared Feeder Cells 7.3.2.26. A minimum of $78×10^6$ feeder cells were needed per lot tested for this protocol. Each 1 ml vial frozen by SDBB had $100×10^6$ viable cells upon freezing. Assuming a 50% recovery upon thaw from LN2 storage, it was recommended to thaw at least two 1 ml vials of feeder cells per lot giving an estimated $100×10^6$ viable cells for each REP. Alternately, if supplied in 1.8 ml vials, only one vial would provide enough feeder cells.

7.3.2.27. Before thawing feeder cells, pre-warmed approximately 50 ml of CM2 without IL-2 for each feeder lot to be tested.

7.3.2.28. Removed the designated feeder lot vials from LN2 storage, placed in zipper storage bag, and place on ice. Transferred vials to tissue culture room.

7.3.2.29. Thawed vials inside closed zipper storage bag by immersing in a 37° C. water bath.

7.3.2.30. Removed vials from zipper bag, spray or wipe with 70% EtOH and transferred vials to BSC.

7.3.2.31. Using a transfer pipet, the contents of feeder vials were immediately transferred into 30 ml of warm CM2 in a 50 ml conical tube. Washed vial with a small volume of CM2 to remove any residual cells in the vial.

7.3.2.32. Centrifuged at 400×CF for 5 minutes.

7.3.2.33. Aspirated the supernatant and resuspended in 4 ml warm CM2 plus 3000 IU/ml IL-2.

7.3.2.34. Removed 200 µl for cell counting using the Automated Cell Counter. Record the counts.

7.3.2.35. Resuspended cells at $1.3 \times 10^7$ cells/ml in warm CM2 plus 3000 IU/ml IL-2.

Setup Co-Culture 7.3.2.36. Diluted TIL cells from $1.3 \times 10^6$ cells/ml to $1.3 \times 10^5$ cells/ml. Worked with each TIL line independently to prevent cross-contamination.

7.3.2.36.1. Added 4.5 ml of CM2 medium to a 15 ml conical tube.

7.3.2.36.2. Removed TIL cells from incubator and resuspended well using a 10 ml serological pipet.

7.3.2.36.3. Removed 0.5 ml of cells from the $1.3 \times 10^6$ cells/ml TIL suspension and add to the 4.5 ml of medium in the 15 ml conical tube. Returned TIL stock vial to incubator.

7.3.2.36.4. Mixed well.

7.3.2.36.5. Repeated steps 7.3.2.36.1-7.3.2.36.4 for the second TIL line.

7.3.2.36.6. When testing more than one feeder lot at one time, diluted the TIL to the lower concentration for each feeder lot just prior to plating the TIL.

7.3.2.37. Transferred flasks with pre-warmed media for a single feeder lot from the incubator to the BSC.

7.3.2.38. Mixed feeder cells by pipetting up and down several times with a 1 ml pipet tip and transfer 1 ml ($1.3 \times 10^7$ cells) to each flask for that feeder lot.

7.3.2.39. Added 60 µl of OKT3 working stock (10 µg/ml) to each flask. 7.3.2.40. Returned the two control flasks to the incubator.

7.3.2.41. Transferred 1 ml ($1.3 \times 10^5$) of each TIL lot to the correspondingly labeled T25 flask.

7.3.2.42. Returned flasks to the incubator and incubated upright. Did not disturb until Day 5.

7.3.2.43. Repeated 7.3.2.36-7.3.2.42 for all feeder lots tested.

7.3.3. Day 5, Media Changed 7.3.3.1. Prepared CM2 with 3000 IU/ml IL-2. 10 ml is needed for each flask 7.3.3.2. To prevent cross-contamination, handled the flasks for a single feeder lot at a time. Removed flasks from the incubator and transferred to the BSC, and care was taken not to disturb the cell layer on the bottom of the flask.

7.3.3.3. Gently removed 10 ml of the media from flask and discarded.

7.3.3.4. Repeated for all flasks including control flask.

7.3.3.5. With a 10 ml pipette, transferred 10 ml warm CM2 with 3000 IU/ml IL-2 to each flask.

7.3.3.6. Returned flasks to the incubator and incubate upright until Day 7. 7.3.3.7. Repeat 7.3.3.1-7.3.3.6 for all feeder lots tested.

7.3.4. Day 7, Harvest 7.3.4.1. To prevent cross-contamination, handled the flasks for a single feeder lot at a time.

7.3.4.2. Removed flasks from the incubator and transferred to the BSC, and care was taken not to disturb the cell layer on the bottom of the flask.

7.3.4.3. Without disturbing the cells growing on the bottom of the flasks, removed 10 ml of medium from each test flask and 15 ml of medium from each of the control flasks.

7.3.4.4. Using a 10 ml serological pipet, resuspended the cells in the remaining medium and mixed well to break up any clumps of cells.

7.3.4.5. Recorded the volumes for each flask in Day 7.

7.3.4.6. After thoroughly mixing cell suspension by pipetting, removed 200 µl for cell counting.

7.3.4.7. Counted the TIL using the appropriate standard operating procedure in conjunction with the automatic cell counter equipment.

7.3.4.8. Recorded counts for Day 7.

7.3.4.9. Repeated 7.3.4.1-7.3.4.8 for all feeder lots tested.

7.3.4.10. Feeder control flasks were evaluated for replication incompetence and flasks containing TIL were evaluated for fold expansion from Day 0 according to the criteria listed in FIG. 2.

7.3.5. Day 7, Continuation of Feeder Control Flasks to Day 14

7.3.5.1. After completing the Day 7 counts of the feeder control flasks, added 15 ml of fresh CM2 medium containing 3000 IU/ml IL-2 to each of the control flasks.

7.3.5.2. Returned the control flasks to the incubator and incubated in an upright position until Day 14.

7.3.6. Day 14, Extended Non-Proliferation of Feeder Control Flasks 7.3.6.1 To prevent cross-contamination, handled the flasks for a single feeder lot at a time.

7.3.6.2 Removed flasks from the incubator and transferred to the BSC, and care was taken not to disturb the cell layer on the bottom of the flask.

7.3.6.3. Without disturbing the cells growing on the bottom of the flasks, removed approximately 17 ml of medium from each control flasks.

7.3.6.4. Using a 5 ml serological pipet, resuspended the cells in the remaining medium and mixed well to break up any clumps of cells.

7.3.6.5. Recorded the volumes for each flask.

7.3.6.6. After thoroughly mixing cell suspension by pipetting, removed 200 µl for cell counting.

7.3.6.7. Counted the TIL using the appropriate standard operating procedure in conjunction with the automatic cell counter equipment.

7.3.6.8. Recorded counts for Day 14.

7.3.6.9. Repeated 7.3.4.1-7.3.4.8 for all feeder lots tested.

Expected Results and Acceptance Criteria

Expected Results

The dose of gamma irradiation was sufficient to render the feeder cells replication incompetent. All lots were expected to meet the evaluation criteria and also demonstrated a reduction in the total viable number of feeder cells remaining on Day 7 of the REP culture compared to Day 0.

All feeder lots were expected to meet the evaluation criteria of 100-fold expansion of TIL growth by Day 7 of the REP culture.

Day 14 counts of Feeder Control flasks were expected to continue the non-proliferative trend seen on Day 7.

Acceptance Criteria

The following acceptance criteria had to be met for each replicate TIL line tested for each lot of feeder cells.
Acceptance was Two-Fold, as Follows (Outlined in FIG. 2, Acceptance Criteria):

Whether the dose of radiation was sufficient to render the MNC feeder cells replication incompetent when cultured in the presence of 30 ng/ml OKT3 antibody and 3000 IU/ml IL-2 was evaluated.

Replication incompetence was evaluated by total viable cell count (TVC) as determined by automated cell counting on Day 7 and Day 14 of the REP.

Acceptance criteria is "No Growth," meaning the total viable cell number had not increased on Day 7 and Day 14 from the initial viable cell number put into culture on Day 0 of the REP.

Evaluate the Ability of the Feeder Cells to Support TIL Expansion.

TIL growth was measured in terms of fold expansion of viable cells from the onset of culture on Day 0 of the REP to Day 7 of the REP.

On Day 7, TIL cultures achieved a minimum of 100-fold expansion, (i.e., greater than 100 times the number of total viable TIL cells put into culture on REP Day 0), as evaluated by automated cell counting.

MNC feeder lots that did not meet these two criteria above were typically excluded.

Any MNC feeder lots that meet acceptance criteria but are judged to have poor performance in regard to the ability to expand TIL relative to other previous feeder lots tested in parallel with the same pre-REP TIL lines, as judged by those of skill in the art could have been excluded. See Table 15 below for acceptance criteria used.

TABLE 14

Acceptance Criteria

| Test | Acceptance criteria |
|---|---|
| Irradiation of MNC/ Replication Incompetence | No growth observed at 7 and 14 days |
| TIL expansion | At least a 100-fold expansion of each TIL (minimum of $1.3 \times 10^7$ viable cells) |

Whether the dose of radiation was sufficient to render the MNC feeder cells replication incompetent when cultured in the presence of 30 ng/ml OKT3 antibody and 3000 IU/ml IL-2 was evaluated.

10.2.2.1.1 Replication incompetence was evaluated by total viable cell count (TVC) as determined by automated cell counting on Day 7 and Day 14 of the REP.

10.2.2.1.2 Acceptance criteria was "No Growth," meaning the total viable cell number was not increased on Day 7 and Day 14 from the initial viable cell number put into culture on Day 0 of the REP.

10.2.2.2 The ability of the feeder cells to support TIL expansion was evaluated.

10.2.2.2.1 TIL growth was measured in terms of fold expansion of viable cells from the onset of culture on Day 0 of the REP to Day 7 of the REP.

10.2.2.2.1 On Day 7, TIL cultures achieved a minimum of 100-fold expansion, (i.e., greater than 100 times the number of total viable TIL cells put into culture on REP Day 0), as evaluated by automated cell counting.

10.2.2.3 When a lot failed to meet the two criteria above, the lot was retested according to the contingency plan outlined in Section 10.3 below.

10.2.2.4 Following retesting of a failed lot, any MNC feeder lot that did not meet the two acceptance criteria in both the original evaluation and the contingency testing was excluded.

10.2.2.5 Any MNC feeder lots that met acceptance criteria but were judged to have poor performance in regard to the ability to expand TIL relative to other previous feeder lots tested in parallel with the same pre-REP TIL lines were excluded as appropriate.

Contingency Testing of MNC Feeder Lots that do not meet acceptance criteria 10.3.1 In the event that an MNC feeder lot met either of the acceptance criteria outlined in Section 10.2 above, the following steps were taken to retest the lot to rule out simple experimenter error as its cause.

10.3.2 If there were two or more remaining satellite testing vials of the lot, then the lot could be retested. If there were one or no remaining satellite testing vials of the lot, then the lot was failed according to the acceptance criteria listed in Section 10.2 above.

10.3.3 Two trained personnel, include the original person who evaluated the lot in question, had to both test the lot at the same time.

10.3.4 Repeating Section 7.2-7.3 was done to re-evaluate the lot in question.

10.3.5 Each person would test the lot in question as well as a control lot (as defined in Section 7.2.4 above).

10.3.6 In order to be qualified, the lot in question and the control lot had to achieve the acceptance criteria of Section 10.2 for both of the personnel doing the contingency testing.

10.3.7 Upon meeting these criteria, the lot could then be released for CMO use as outlined in Section 10.2 above.

Example 7: Procedure for Qualifying Individual Lots of Gamma-Irradiated Peripheral Blood Mononuclear Cells This Example describes a novel abbreviated procedure for qualifying individual lots of gamma-irradiated peripheral blood mononuclear cells (PBMC) for use as allogeneic feeder cells in the exemplary methods described herein. This example provides a protocol for the evaluation of irradiated PBMC cell lots for use in the production of clinical lots of TIL. Each irradiated PBMC lot was prepared from an individual donor. Over the course of more than 100 qualification protocols, it has been shown that, in all cases, irradiated PBMC lots from SDBB (San Diego Blood Bank) can expand TILs >100-fold on Day 7 of a REP. This modified qualification protocol is intended to apply to irradiated donor PBMC lots from SDBB which must still be tested to verify that the received dose of gamma radiation was sufficient to render them replication incompetent. Once demonstrated that they maintain replication incompetence over the course of 14 days, donor PBMC lots were considered "qualified" for usage to produce clinical lots of TIL.

Key Terms and Definitions

μg—Microgram

μl—Microliter

AIM-V—commercially available cell culture medium
Biological Safety Cabinet

BSC—Cluster of Differentiation

CD—Complete Medium for TIL #2

CM2—CM2 supplemented with 3000 IU/ml IL-2

CM2IL2—Contract Manufacturing Organization $CO_2$—Carbon Dioxide

EtOH—Ethanol
GMP—Good Manufacturing Practices
Gy—Gray
IL—Interleukin
IU—International Units
LN2—Liquid Nitrogen
MI—Milliliter
NA—Not Applicable
OKT3—anti-CD3 monoclonal antibody designation
P20—2-20 µl pipettor
P200—20-200 µl pipettor
PBMC—peripheral blood mononuclear cells
P1000—100-1000 µl pipettor
PPE—Personal Protective Equipment
REP—Rapid Expansion Protocol
SDBB—San Diego Blood Bank
TIL—Tumor Infiltrating Lymphocytes
T25—25 cm2 tissue culture flask
xg—"times gravity"—measure of relative centrifugal force
Specimens included Irradiated donor PBMC (SDBB).
Procedure
Background
7.1.1 Gamma-irradiated, growth-arrested PBMC were required for current standard REP of TIL. Membrane receptors on the PBMCs bind to anti-CD3 (clone OKT3) antibody and crosslink to TIL in culture, stimulating the TIL to expand. PBMC lots were prepared from the leukapheresis of whole blood taken from individual donors. The leukapheresis product was subjected to centrifugation over Ficoll-Hypaque, washed, irradiated, and cryopreserved under GMP conditions.
It is important that patients who receive TIL therapy not be infused with viable PBMCs as this can result in Graft-Versus-Host Disease (GVHD). Donor PBMCs were therefore growth-arrested by dosing the cells with gamma-irradiation, resulting in double strand DNA breaks and the loss of cell viability of the PBMCs upon reculture.
Evaluation Criteria
7.2.1 Evaluation criterion for irradiated PBMC lots was their replication incompetency.
Experimental Set-Up
7.3.1 Feeder lots were tested in mini-REP format as if they were to be co-cultured with TIL, using upright T25 tissue culture flasks.
7.3.1.1 Control lot: One lot of irradiated PBMCs, which had historically been shown to meet the criterion of 7.2.1, was run alongside the experimental lots as a control.
7.3.2 For each lot of irradiated donor PBMC tested, duplicate flasks were run.
Experimental Protocol
All tissue culture work in this protocol was done using sterile technique in a BSC.
Day 0
7.4.1 Prepared ~90 ml of CM2 medium for each lot of donor PBMC to be tested. Kept CM2 warm in 37° C. water bath.
7.4.2 Thawed an aliquot of $6 \times 10^6$ IU/ml IL-2.
7.4.3 Returned the CM2 medium to the BSC, wiping with 70% EtOH prior to placing in hood. For each lot of PBMC tested, about 60 ml of CM2 was removed to a separate sterile bottle. Added IL-2 from the thawed $6 \times 10^6$ IU/ml stock solution to this medium for a final concentration of 3000 IU/ml. Labeled this bottle as "CM2/IL2" (or similar) to distinguish it from the unsupplemented CM2.
7.4.4 Labeled two T25 flasks for each lot of PBMC to be tested. Minimal label included:
7.4.4.1 Lot number
7.4.4.2 Flask number (1 or 2)
7.4.4.3 Date of initiation of culture (Day 0)
Prepared OKT3
7.4.5 Took out the stock solution of anti-CD3 (OKT3) from the 4° C. refrigerator and placed in the BSC.
7.4.6 A final concentration of 30 ng/ml OKT3 was used in the media of the mini-REP.
7.4.7 Prepared a 10 µg/ml working solution of anti-CD3 (OKT3) from the 1 mg/ml stock solution. Placed in refrigerator until needed.
7.4.7.1 For each PBMC lot tested, prepared 150 µl of a 1:100 dilution of the anti-CD3 (OKT3) stock.
E.g., for testing 4 PBMC lots at one time, prepared 600 µl of 10 µg/ml anti-CD3 (OKT3) by adding 6 µl of the 1 mg/ml stock solution to 594 µl of CM2 supplemented with 3000 IU/ml IL-2.
Prepared Flasks
7.4.8 Added 19 ml per flask of CM2/IL-2 to the labeled T25 flasks and place flasks into 37° C., humidified, 5% $CO_2$ incubator while preparing cells.
Prepared Irradiated PBMC
7.4.9 Worked with each donor PBMC lot individually to avoid the potential cross-contamination of the lots.
7.4.10 Retrieved vials of PBMC lots to be tested from LN2 storage. These were placed at −80° C. or kept on dry ice prior to thawing.
7.4.11 Placed 30 ml of CM2 (without IL-2 supplement) into 50 ml conical tubes for each lot to be thawed. Labeled each tube with the different lot numbers of the PBMC to be thawed. Capped tubes tightly and place in 37° C. water bath prior to use. As needed, returned 50 ml conical tubes to the BSC, wiping with 70% EtOH prior to placing in the hood.
7.4.12 Removed a vial PBMC from cold storage and place in a floating tube rack in a 37° C. water bath to thaw. Allowed thaw to proceed until a small amount of ice remains in the vial.
7.4.13 Sprayed or wiped thawed vial with 70% EtOH and transfer to BSC.
7.4.14 Using a sterile transfer pipet, the contents of the vial were immediately transferred into the 30 ml of CM2 in the 50 ml conical tube. Removed about 1 ml of medium from the tube to rinse the vial; returned rinse to the 50 ml conical tube. Capped tightly and swirl gently to wash cells.
7.4.15 Centrifuged at 400×g for 5 min at room temperature.
7.4.16 Aspirated the supernatant and resuspended the cell pellet in 1 ml of warm CM2/IL-2 using a 1000 µl pipet tip. Alternatively, prior to adding medium, resuspended cell pellet by dragging capped tube along an empty tube rack. After resuspending the cell pellet, bring volume to 4 ml using CM2/IL-2 medium. Recorded volume.
7.4.17 Removed a small aliquot (e.g., 100µ1) for cell counting using an automated cell counter.
7.4.17.1 Performed counts in duplicate according to the particular automated cell counter SOP. It was often necessary to perform a dilution of the PBMC prior to performing the cell counts. A recommended starting dilution was 1:10, but this could vary depending on the type of cell counter used.

7.4.17.2 Recorded the counts.

7.4.18 Adjusted concentration of PBMC to $1.3\times10^7$ cells/ml as per step 7.4.15.2 using CM2/IL-2 medium. Mixed well by gentle swirling or by gently aspirating up-and-down using a serological pipet.

Set Up Culture Flasks 7.4.19 Returned two labeled T25 flasks to the BSC from the tissue culture incubator.

7.4.20 Returned the 10 μg/ml vial of anti-CD3/OKT3 to the BSC.

7.4.21 Added 1 ml of the $1.3\times10^7$ PBMC cell suspension to each flask.

7.4.22 Added 60 μl of the 10 μg/ml anti-CD3/OKT3 to each flask.

7.4.23 Returned capped flasks to the tissue culture incubators for 14 days of growth without disturbance.

7.4.24 The anti-CD3/OKT3 vial was placed back into the refrigerator until needed for the next lot.

7.4.25 Repeated steps 7.4.9-7.4.24 for each lot of PBMC to be evaluated.

Day 14, Measurement of Non-proliferation of PBMC 7.4.26 Working with each lot independently, carefully returned the duplicate T25 flasks to the BSC.

7.4.27 For each flask, using a fresh 10 ml serological pipet, removed ~17 ml from each of the flasks, then carefully pulled up the remaining media to measure the volume remaining in the flasks. Recorded volume.

7.4.28 Mixed sample well by pipetting up and down using the same serological pipet.

7.4.29 Removed a 200 μl sample from each flask for counting.

7.4.30 Counted cells using an automated cell counter.

7.4.31 Repeated steps 7.4.26-7.4.31 for each lot of PBMC being evaluated.

Results and Acceptance Criterion

Results 10.1.1 The dose of gamma irradiation was sufficient to render the feeder cells replication incompetent. All lots were expected to meet the evaluation criterion and demonstrated a reduction in the total viable number of feeder cells remaining on Day 14 of the REP culture compared to Day 0.

Acceptance Criterion 10.2.1 The following acceptance criterion was met for each irradiated donor PBMC lot tested:

10.2.2 "No growth"—meaning that the total number of viable cells on Day 14 was less than the initial viable cell number put into culture on Day 0 of the REP.

10.2.3 Should a lot fail to meet the criterion above, the lot was retested per the Contingency Testing Procedure outlined in the section 10.4.

10.2.4 Following retesting of a failed lot, any MNC feeder lot that did not meet the acceptance criterion in both the original evaluation and the contingency testing was excluded.

Contingency Testing of PBMC lots which did not meet acceptance criterion.

10.4.1 In the event than an irradiated donor PBMC lot did not meet the acceptance criterion above, the following steps were taken to retest the lot to rule out simple experimenter error as the cause of its failure.

10.4.2 If there were two or more remaining satellite vials of the lot, then the lot was retested. If there were one or no remaining satellite vials of the lot, then the lot was failed according to the acceptance criterion of section 10.2 above.

10.4.3 Whenever possible, two trained personnel (preferably including the original person who evaluated the lot in question) did the testing of the two separate vials independently. This was the preferred method of contingency testing. Aside from the separate vials of PBMC, the same reagents can be used by both personnel.

10.4.3.1 If two personnel were not available, one person did the testing of the two PBMC vials for the failed lot, working with each vial independently.

10.4.4 Repeating of section 7.4 "Experimental Protocol" was done to re-evaluated the lot in question.

10.4.5 In addition to the lot in question, a control lot was tested by each person carrying out the contingency testing.

10.4.5.1 If two personnel perform contingency testing, both personnel tested the control lot independently.

10.4.5.2 If only one person was available to perform contingency testing, it was not necessary for the control lot to be run in duplicate.

10.4.5.3 To be qualified, a PBMC lot going through contingency testing must have had both the control lot and both replicates of the lot in question achieve the acceptance criterion of Section 10.2 to pass.

10.4.5.4 Upon meeting this criterion, the lot was then be released for CMO usage as outlined in section 10.2.

Example 8: Comparison of Pre- and Post-Cryopreserved TILS

Antibody cocktails for the samples and the FMO controls were made before starting the sample preparation and staining procedure. The cocktails were stored at 4° C. in the dark for up to 60 days. See Cocktail Preparation section below.

TABLE 15

Staining Procedure:

| Step | Description |
| --- | --- |
| 1 | Removed Aqua dye aliquot from the freezer.ptdark. |
| 2 | Added 3 mL 1 × PBS to each sample tube |
| 3 | Spun tubes at 300 g for 5 minutes. |
| 4 | Prepared Aqua Live/Dead stain. Dilute 1:200 in PBS. 25 μL 4 per sample and FMO control tube is needed. 1:200 = _____ μL Aqua + _____ mL PBS |
| 5 | Aspirated or decanted supernatant from step 3. |
| 6 | Added 25 μL of Aqua L/D to each sample tube. Resuspended cells by dragging along rack. Incubated 15 min., dark, room temperature. |
| 7 | Without washing, added 50 μL of appropriate Ab cocktail to each tube. |
| 8 | Incubated tubes for 15 minutes at room temperature. |
| 9 | Added 3 mLs of FACS Wash buffer |
| 10 | Spun at 330 g for 5 min at 4° C. |
| 11 | Resuspended tubes by dragging along an empty tube rack. |
| 12 | Added 100 μL 1% PFA/PBS solution at 4° C. |
| 13 | Stored samples at 4° C. in dark for up to 72 hours. |
| 14 | Ran samples on Flow Cytometer |

TABLE 16

Differentiation Panel 1 (DF1):

| Target | Format | Clone | Supplier | Catalog Number | Titre |
|---|---|---|---|---|---|
| TCRab | PE/Cy7 | IP26 | BioLegend | 306720 | 3 |
| CD57* | PerCP-Cy5.5 | HNK-1 | BioLegend | 359622 | 2 |
| CD28* | PE | CD28.2 | BioLegend | 302908 | 2 |
| CD4 | FITC | OKT4 | eBioscience | 11-0048-42 | 2 |
| CD27* | APC-H7 | M-T271 | BD Biosciences | 560222 | 3 |
| CD56 | APC | N901 | Beckman Coulter | IM2474U | 3 |
| CD8a | PB | RPA-T8 | BioLegend | 301033 | 2 |
| FACS Buffer | | | | | 33 |

TABLE 17

Differentiation Panel 2 (DF2):

| Target | Format | Clone | Supplier | Catalog Number | Titre |
|---|---|---|---|---|---|
| CD45RA* | PE-Cy7 | HI100 | BD Biosciences | 560675 | 1 |
| CD8a | PerCP/Cy5.5 | RPA-T8 | BioLegend | 301032 | 2 |
| CCR7* | PE | 150503 | BD Biosciences | 560765 | 5 |
| CD4 | FITC | OKT4 | eBioscience | 11-0048-42 | 2 |
| CD3 | APC/Cy7 | HIT3a | BioLegend | 300318 | 2 |
| CD38* | APC | HB-7 | BioLegend | 356606 | 1 |
| HLA-DR | PB | L243 | BioLegend | 307633 | 2 |
| FACS Buffer | | | | | 35 |

*Denotes FMO (Fluorescence Minus One) control should be made.

TABLE 18

T cell Activation Panel 1 (Tact1)

| Target | Format | Clone | Supplier | Catalog Number | Titre |
|---|---|---|---|---|---|
| CD137* | PE/Cy7 | 4B4-1 | BioLegend | 309818 | 2 |
| CD8a | PerCP/Cy5.5 | RPA-T8 | BioLegend | 301032 | 2 |
| Lag3* | PE | 3DS223H | eBioscience | 12-2239-42 | 5 |
| CD4 | FITC | OKT4 | BioLegend | 317408 | 2 |
| CD3 | APC/Cy7 | HIT3a | BioLegend | 300318 | 1 |
| PD1* | APC | EH12.2H7 | BioLegend | 329908 | 2 |
| Tim-3* | BV421 | F38-2E2 | BioLegend | 345008 | 2 |
| FACS Buffer | | | | | 34 |

TABLE 19

T cell Activation Panel 2 (Tact2)

| Target | Format | Clone | Supplier | Catalog Number | Titre |
|---|---|---|---|---|---|
| CD69* | PE-Cy7 | FN50 | BD Biosciences | 557745 | 3 |
| CD8a | PerCP/Cy5.5 | RPA-T8 | BioLegend | 301032 | 2 |
| TIGIT* | PE | MBSA43 | eBioscience | 12-9500-42 | 3 |
| CD4 | FITC | OKT4 | BioLegend | 317408 | 2 |
| CD3 | APC/Cy7 | HIT3a | BioLegend | 300318 | 2 |
| KLRG1* | Ax647 | SA231A2 | BioLegend | 367704 | 1 |
| CD154* | BV421 | TRAP1 | BD Biosciences | 563886 | 3 |
| FACS Buffer | | | | | 34 |

*Denotes FMO (Fluorescence Minus One) control should be made.

Compensation Controls
1. Added one drop of BD Comp beads to 11 tubes.
2. Labeled tubes 1 through 7 with the chromophores from DF1
3. Labeled tubes 8 through ten with APCy7, BV421, and Ax647.
4. Tube 11 was for unlabeled beads.
5. Added 5 μL of Antibody to each tube.
6. Incubated 10 to 30 minutes in dark, room temperature.
7. Washed with 3 mLs FACS Buffer
8. Resuspended with 500 uL 1% PFA.
9. Added one drop of BD Comp negative bead to each tube.
10. Stored at 4° C. in dark. Could be used for one week.

Aqua Control:
1. Added one drop of Arc positive control to tube labelled Aqua.
2. Added 34 of thawed aqua solution to tube.
3. Repeated steps 6-10 as above. Except used the negative Arc bead for step 9.

TABLE 20

Setup.

| Tube | Target | Format | Titre |
|---|---|---|---|
| 1 | TCRab | PE/Cy7 | 5 |
| 2 | CD57 | PerCP-Cy5.5 | 5 |
| 3 | CD28 | PE | 5 |
| 4 | CD4 | FITC | 5 |
| 5 | CD27 | APC-H7 | 5 |
| 6 | CD56 | APC | 5 |
| 7 | CD8a | PB | 5 |
| 8 | CD3 | APC/Cy7 | 5 |
| 9 | Tim-3 | BV421 | 5 |
| 10 | KLRG1 | Ax647 | 5 |
| 11 | Unlabeled | n/a | n/a |

Example 9: Remarkably Stable Tumor-Infiltrating Lymphocytes (TIL) for Infusion Phenotype Following Cryopreservation Abstract Background:

This Example discusses the development of cancer immunotherapies based on tumor-infiltrating lymphocytes (TIL) with the ultimate goal of developing therapeutic populations of TILs. Cryopreservation of TILs allows the final cell product to be shipped in a safe manner with fewer temporal constraints (Axelsson S, Faresjo M, Hedman M, Ludvigsson J, Casas R: Cryopreserved peripheral blood mononuclear cells are suitable for the assessment of immunological markers in type 1 diabetic children. Cryobiology 2008, 57:201-8.)

Here, fresh versus frozen/thawed TIL samples were evaluated for the expression of individual phenotypic markers to assess whether phenotypic changes occur with cryopreserved TILs. (See, for example, Sadeghi A, Ullenhag G, Wagenius G, Totterman T H, Eriksson F: Rapid expansion of T cells: Effects of culture and cryopreservation and importance of short-term cell recovery. Acta Oncol. 2013, 52:978-86)

Results:

No significant differences in CD4, CD8, NK, TCRαβ expression, or memory markers comparing fresh versus thawed TIL were observed. The activation status of TIL as defined by HLA-DR, CD38, and CD69 expression was maintained while regulatory molecules LAG-3 and TIM-3 demonstrated a slight decrease in expression. In addition, the viability of both the fresh and thawed product was greater than 86%.

Methods:

PreREP TILs were obtained by culturing melanoma tumor fragments in IL-2 (6000 IU/ml).

Rapid Expansion Protocol (REP) cells were initiated using irradiated allogeneic PBMC feeder cells with OKT3 and IL-2 in a GREX-100 flask for 11-14 days.

Cultured cells were cryopreserved in 5% DMSO.

Flow cytometric evaluation of fresh and thawed TIL following rest for 1 to 2 hours in IL-2 was performed using four panels consisting of lineage, differentiation, activation, and regulatory markers.

Conclusion:

Cryopreservation did not affect the measured phenotypic characteristics of TIL, with the exception of modest changes in some regulatory molecules. We are investigating the possibility of using cryopreserved TIL in a clinical setting.

Example 10: Memory Cell Subsets in Fresh Versus ReREP TIL populations

Figure 8:
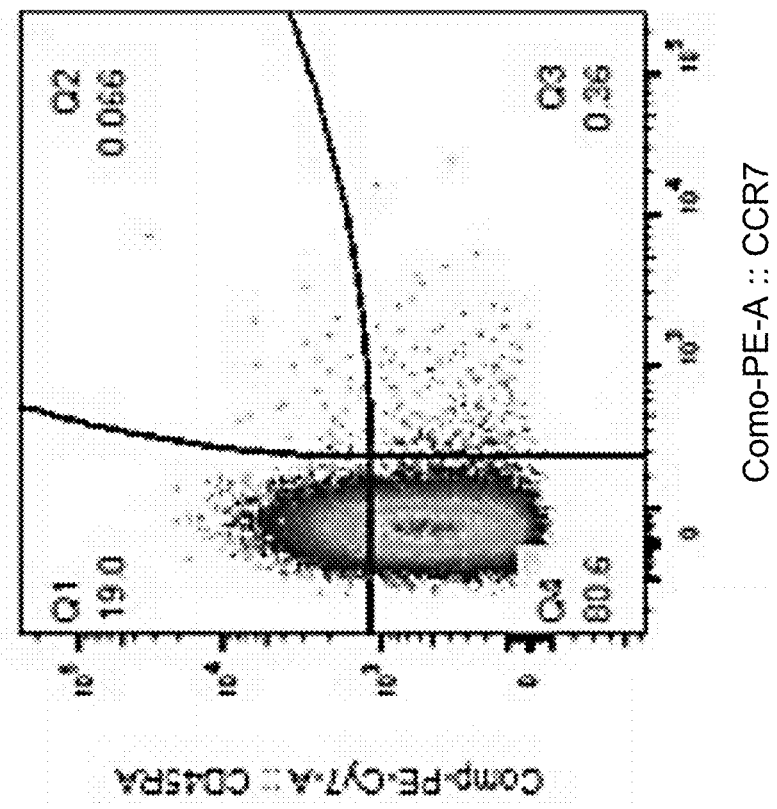
FIG. 8: Scatter plot showing phenotypic characterization of reREP TILs. Q1 shows 19.0% CD45RA$^+$/CCR7$^-$; Q2 shows 0.066% CD45RA$^+$/CCR7$^+$; Q4 shows 80.6% CD45RA$^-$/CCR7$^-$; and Q3 shows 0.36% CD45RA$^-$/CCR7$^+$.

In previous experiments, no central memory subset was seen with fresh TIL populations (see, FIG. 8). However, after the ReREP nearly 60% central memory cells, as provided in Table 22 below.

Figure 9:
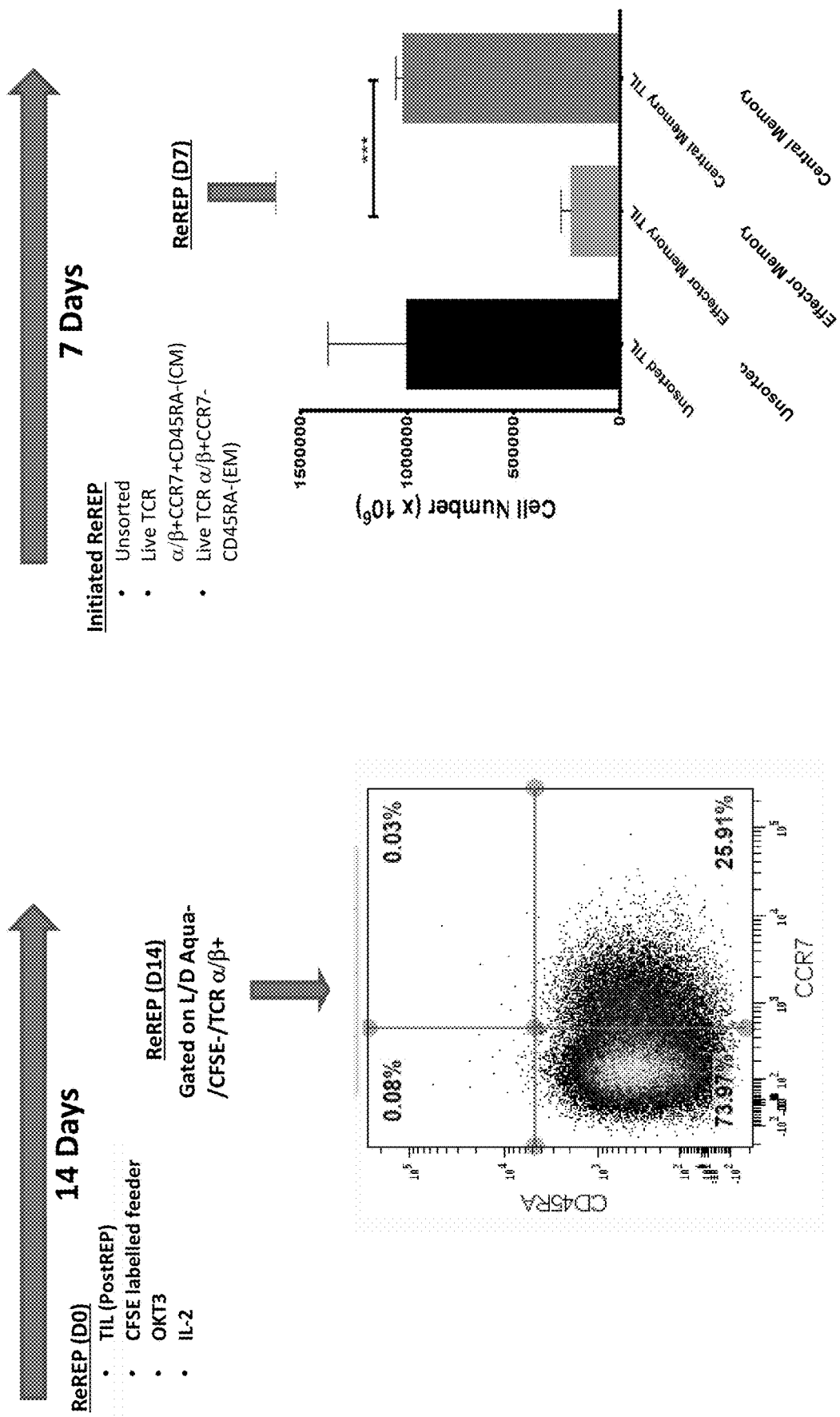
FIG. 9: Diagram and data showing the phenotypic characterization of reREP TILs, during the first and second expansion phases 0.08% CD45RA$^+$/CCR7$^-$; 0.03% CD45RA$^+$/CCR7$^+$; 73.97% CD45RA$^-$/CCR7$^-$; and 25.91% CD45RA$^-$/CCR7$^+$ at Day 14, after the first expansion but prior to the second expansion. Proliferation of CM or EM TIL in the repeat ReREP. Central Memory (CM) TIL and Effector Memory (EM) TIL were tested for the proliferation capacity using repeat ReREP. Briefly, 1.3×10$^6$ Post REP TIL were co-culture with 1.3×10$^7$ PBMC feeders (CFSE labelled), OKT3 (30 ng/nl) and rhIL-2 (3000 IU/ml), culture was incubated for 14 days. On Day 14, central memory TIL and effector memory TIL were gated for L/D Aqua−/CFSE−/TCRα/β+/CD45RA−/CCR7+ and L/D Aqua−/CFSE−/TCRα/β+/CD45RA−/CCR7− population respectively and flow cytometry sorted. Purity of the cell population was 97%. 1×10$^4$ flow sorted CM or EM or unsorted TIL were then cultured 1×10$^6$ PBMC feeders, OKT3 (30 ng/nl) and IL-2 (3000 IU/ml) in triplicates for 7 days. Cell were counted and recorded. Central memory TIL were more proliferative when compared to Effector memory TIL. We are repeating this experiment with more post REP TIL lines.
Figure 10:
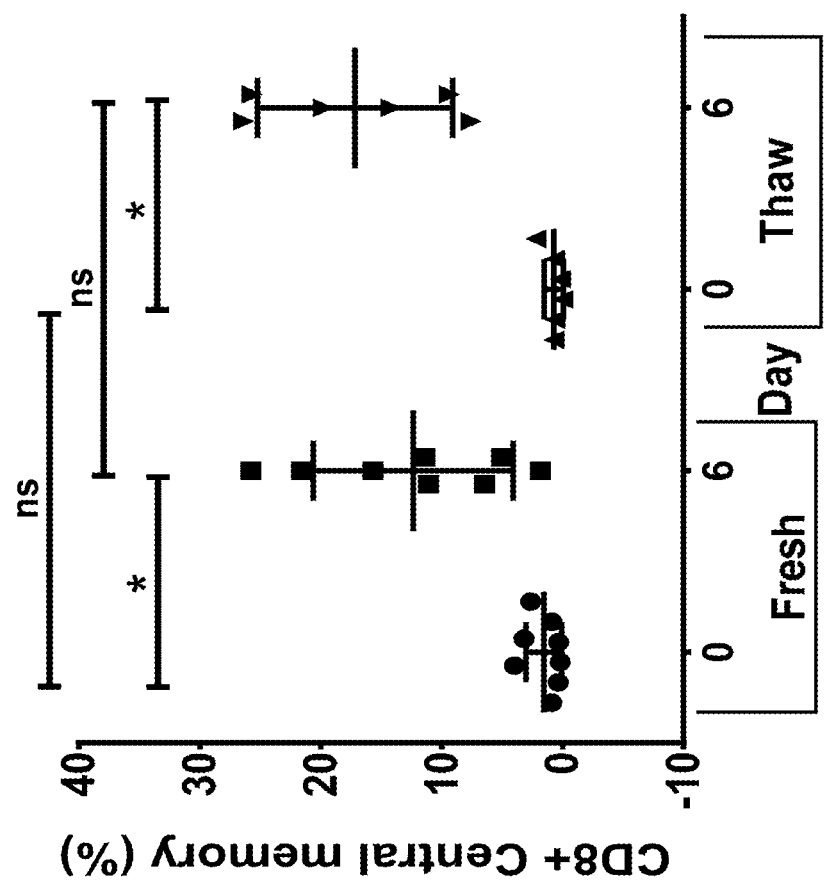
FIGS. 10A and 10B: Phenotypic characterization of TILs during ReREP. Cells were gated on Aqua−/TCR α/β+/CD4+ or CD8+ to show Central Memory TILs (CD45RA$^-$ CCR7$^+$) or Effector Memory TILs (CD45RA$^-$CCR$^-$) memory phenotype. Student "t" was used to calculate statistical significance. *p<0.05, ns non-significant.

Based on the raw numbers, the rested cells had a slightly higher CD4 population than the not rested. Overall the CD8 percentage was high as expected. It's roughly a 60/40 split for CM (central memory—Q3)/EM (effector memory—Q4) among the CD8s. The CD8+CD28+ expression looks interesting. The rested cells have a higher amount. See also, FIGS. 9 and 10A-10B. See, also FIG. 15.

Figure 12:
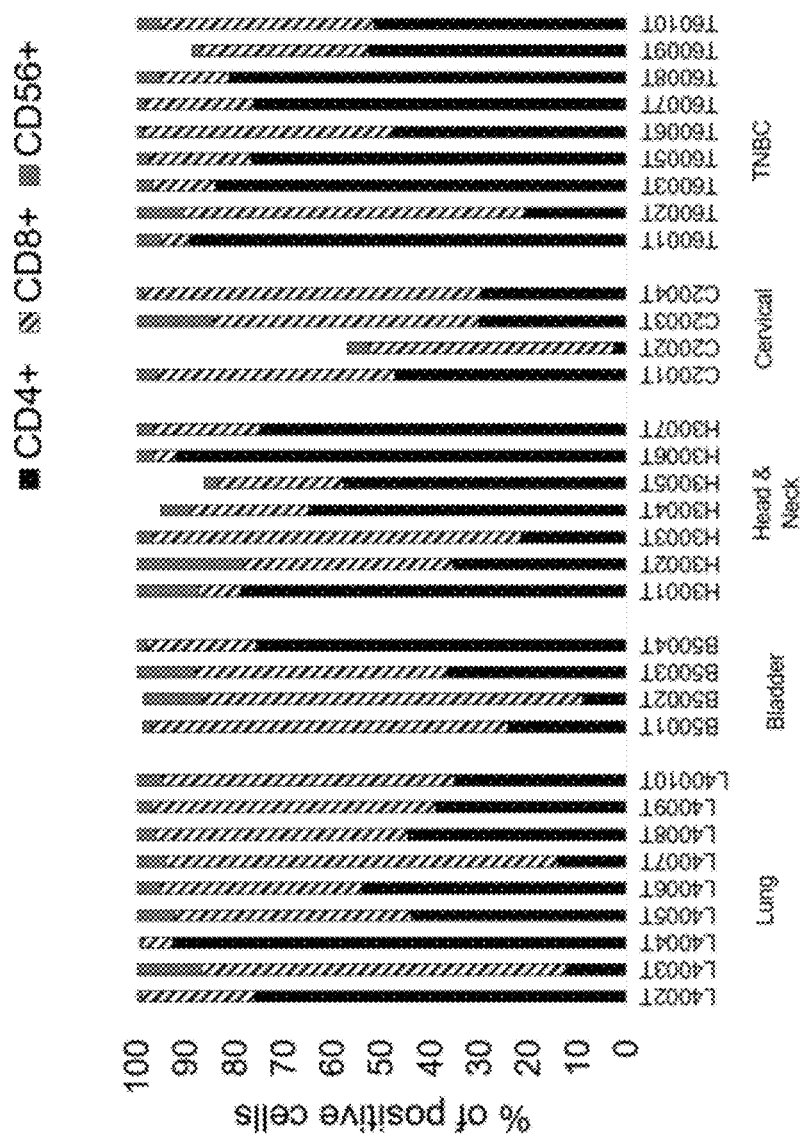
FIG. 12: Successful expansion of TILs from non-melanoma tumors. Data shows the distribution of TIL (CD4+/CD8+) in non-melanoma tumors.
Figure 13:
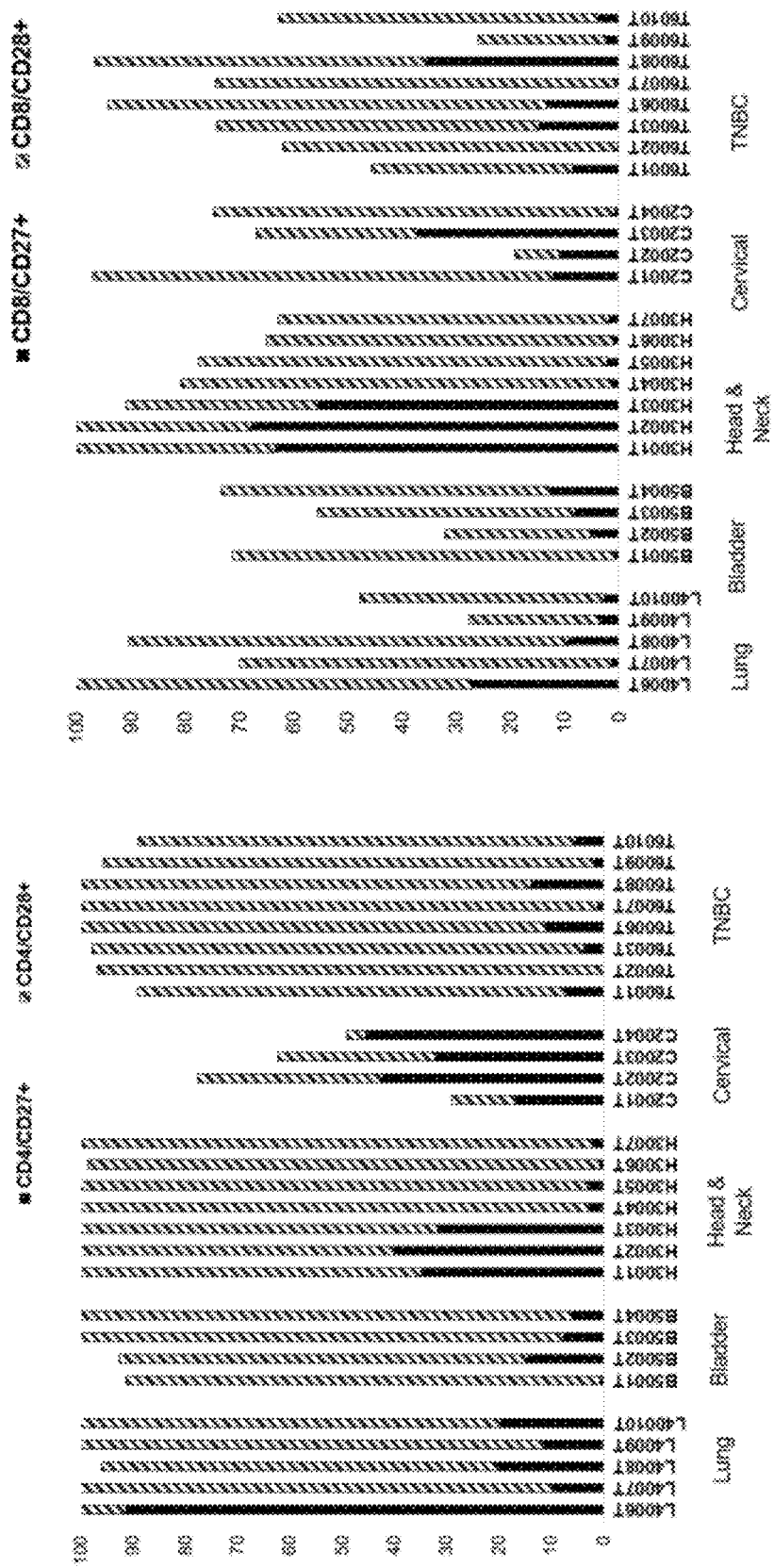
FIG. 13: Non-melanoma TILs expressed CD27 and CD38, consistent with young TILs.
Figure 14:
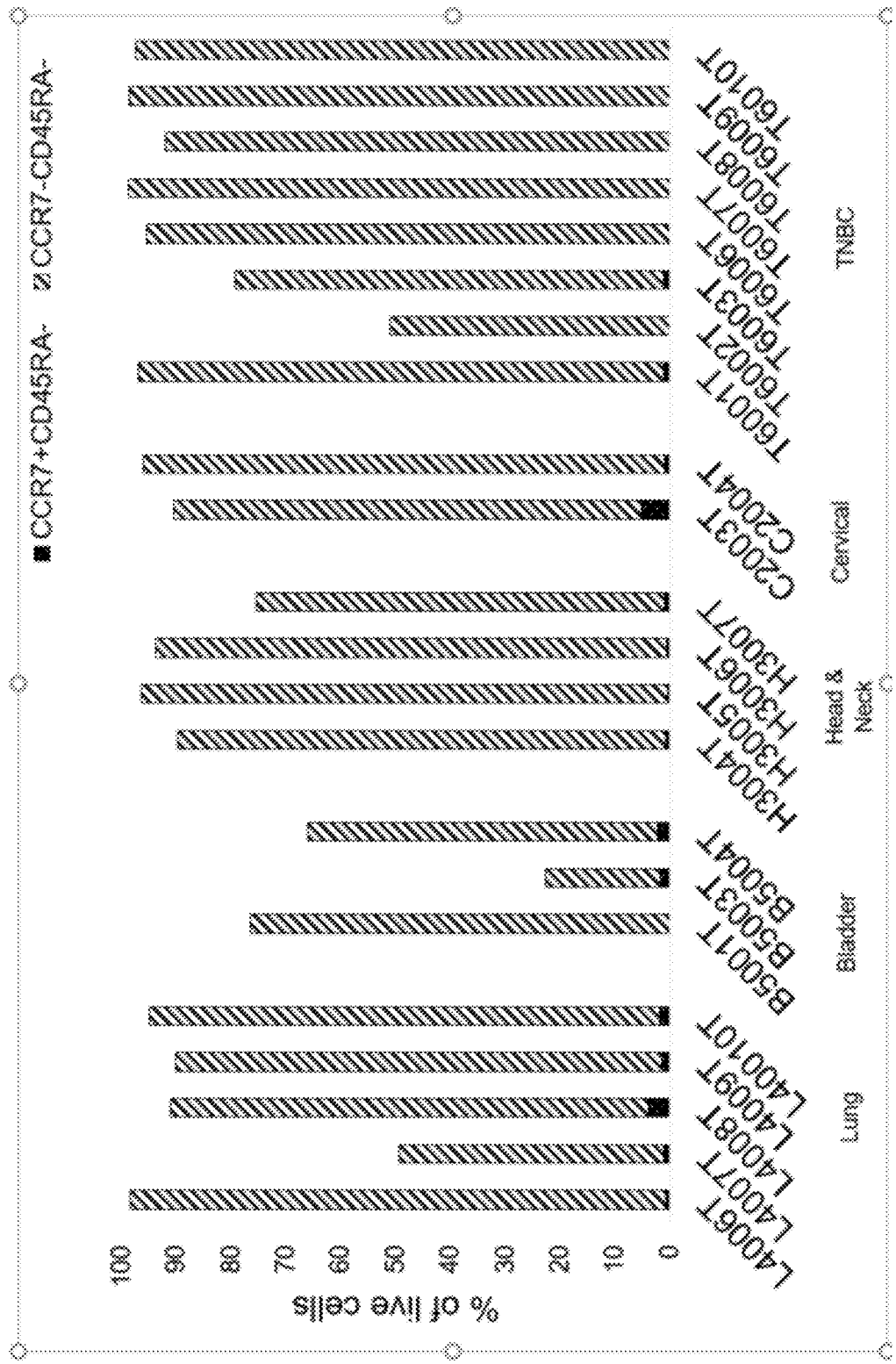
FIG. 14: Activated TILs skew towards effector memory population.

Example 11: Administration of Autologous Tumor Infiltrating Lymphocytes (TILS) in Melanoma Patients Administration of autologous tumor infiltrating lymphocytes (TILs) in melanoma patients has shown an overall response of 55% at NCI, 38% at Moffitt Cancer Center, 48% at MD Anderson Cancer Center, and 40% in Sheba at the Ella Cancer Institute, Israel. The durable responses observed in melanoma patients using ACT may permit broader application to other solid tumors. As shown herein, the feasibility of growing TILs and developing TIL therapies for other solid tumors is demonstrated. The example provides data showing "Successful expansion and characterization of tumor infiltrating lymphocytes (TILs) from non-melanoma tumors.", see, FIGS. 12-14.

Phenotypic characterization of TILs from bladder, cervical, and lung cancer were greater than 60-70% CD8+ T-cells whereas TILs from head and demonstrated variable distribution of CD8+ and CD4+ T-cells. TILs propagated from TNBC were greater than 80% CD4+ T-cells. Regardless of the tumors, most cultures had less than 20% CD56+NK cells.

TILs were prepared by:
a. Washing an obtained tumor in HBSS;
b. Dicing the tumor into fragments (e.g., 2-3 mm3 fragments);
c. Placing the tumor fragments in G-REX 10 cell culture flasks with medium containing serum and IL-2;
d. Exchanging media on day 7 and every 4-5 days from day 11 until day 21; and
e. Assessing cell count, viability, and phenotyping followed by cryopreservation for future purposes including, but not limited to, future delivery to patients for the treatment of tumors, as described herein.

As demonstrated herein, TILs were grown from lung, bladder, head and neck, cervical, and TNBC patient tumors.

Moreover, as demonstrated herein, lung, bladder, and cervical tumors showed greater proportion of CD8+ TILs. Head and neck and TNBC tumors were mostly CD4+ TILs. In addition, further characterization of CD4+ and CD8+ TILs demonstrated effector memory phenotypic cells that were also CD27+ and CD28+.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

The invention claimed is:

1. A cryopreserved tumor infiltrating lymphocyte (TIL) composition comprising a therapeutic population of TILs, wherein the cryopreserved TIL composition is produced by the method comprising:
   (a) performing a first expansion by (i) thawing a cryopreserved tumor digest comprising a first population of TILs from a tumor that was resected from a subject, digested after the resection, and cryopreserved after the digestion, and (ii) culturing the first population of TILs in a cell culture medium comprising IL-2 to produce a second population of TILs, wherein the tumor digest was prepared by incubating a sample of the tumor that was resected from the subject in an enzymatic media;
   (b) performing a second expansion by supplementing the cell culture medium of the second population of TILs with additional IL-2, OKT-3, and antigen presenting cells (APCs), to produce a third population of TILs, wherein the third population of TILs is a therapeutic population of TILs, and wherein the second expansion is performed for about 7 to 14 days in order to obtain the therapeutic population of TILs;
   (c) harvesting the therapeutic population of TILs obtained from step (b);
   (d) admixing the harvested therapeutic population of TILs from step (c) with a cryopreservation media to form an admixture; and
   (e) cryopreserving the admixture from step (d) using a cryopreservation process to produce a cryopreserved TIL composition.

2. The cryopreserved TIL composition according to claim 1, wherein the cryopreservation media comprises a cryopreservant.

3. The cryopreserved TIL composition according to claim 2, wherein the cryopreservant is DMSO.

4. The cryopreserved TIL composition according to claim 3, wherein the cryopreservation media comprises 5% DMSO.

5. The cryopreserved TIL composition according to claim 1, wherein the method further comprises disrupting the tumor sample mechanically so as to dissociate the tumor sample.

6. The cryopreserved TIL composition according to claim 5, wherein the method further comprises purifying the disassociated tumor sample using a density gradient separation.

7. The cryopreserved TIL composition according to claim 1, wherein the enzymatic media comprises DNase.

8. The cryopreserved TIL composition according to claim 7, wherein the enzymatic media comprises 30 units/mL of DNase.

9. The cryopreserved TIL composition according to claim 1, wherein the enzymatic media comprises collagenase.

10. The cryopreserved TIL composition according to claim 9, wherein the enzymatic media comprises 1.0 mg/mL of collagenase.

11. The cryopreserved TIL composition according to claim 1, wherein the cell culture medium is CTS Optimizer.

12. The cryopreserved TIL composition according to claim 1, wherein the APCs comprise peripheral blood mononuclear cells (PBMCs).

13. The cryopreserved TIL composition according to claim 1, wherein the first expansion is performed within from about 3 to 11 days.

14. The cryopreserved TIL composition according to claim 1, wherein steps (a) through (e) are performed within about 24 days.

15. The cryopreserved TIL composition according to claim 1, wherein step (a) further comprises adding the thawed tumor digest into a closed system prior to culturing the first population of TILs.

16. The cryopreserved TIL composition according to claim 1, wherein the transition from step (a) to step (b), the transition from step (b) to step (c), or the transition from step (c) to step (d) occurs without opening the system.

17. The cryopreserved TIL composition according to claim 1, wherein the transition from step (a) to step (b) occurs without opening the system.

18. The cryopreserved TIL composition according to claim 1, wherein the transition from step (b) to step (c) occurs without opening the system.

19. The cryopreserved TIL composition according to claim 1, wherein the transition from step (c) to step (d) occurs without opening the system.

20. The cryopreserved TIL composition according to claim 1, wherein step (a) further comprises adding the thawed tumor digest into a closed system prior to culturing the first population of TILs, wherein the transition from step (a) to step (b) occurs without opening the system, wherein the transition from step (b) to step (c) occurs without opening the system, and wherein the transition from step (c) to step (d) occurs without opening the system.

* * * * *